US012797496B2

(12) United States Patent
Taghipour

(10) Patent No.: US 12,797,496 B2
(45) Date of Patent: Nov. 17, 2026

(54) UV-LED PHOTOREACTORS WITH CONTROLLED RADIATION AND HYDRODYNAMICS AND METHODS FOR FABRICATION AND USE OF SAME

(71) Applicant: THE UNIVERSITY OF BRITISH COLUMBIA, Vancouver (CA)

(72) Inventor: Fariborz Taghipour, Burnaby (CA)

(73) Assignee: THE UNIVERSITY OF BRITISH COLUMBIA, Vancouver (CA)

(*) Notice: Subject to any disclaimer, the term of this patent is extended or adjusted under 35 U.S.C. 154(b) by 328 days.

(21) Appl. No.: 16/632,203

(22) PCT Filed: Jul. 19, 2018

(86) PCT No.: PCT/CA2018/050879
§ 371 (c)(1),
(2) Date: Jan. 17, 2020

(87) PCT Pub. No.: WO2019/014770
PCT Pub. Date: Jan. 24, 2019

(65) Prior Publication Data

US 2020/0230270 A1 Jul. 23, 2020

Related U.S. Application Data

(60) Provisional application No. 62/534,637, filed on Jul. 19, 2017.

(51) Int. Cl.

*A61L 2/10* (2026.01)
*A61L 2/26* (2006.01)

(Continued)

(52) U.S. Cl.

CPC .................. *A61L 2/10* (2013.01); *A61L 2/26* (2013.01); *A61L 9/20* (2013.01); *C02F 1/325* (2013.01);

(Continued)

(58) Field of Classification Search

CPC ..... A61L 2/10; A61L 2/26; A61L 9/20; A61L 2202/11; A61L 2202/122; A61L 2209/12;

(Continued)

(56) References Cited

U.S. PATENT DOCUMENTS

| | | | | |
|---|---|---|---|---|
| 6,342,188 B1 * | 1/2002 | Pearcey | C02F 1/325 204/671 |
| 9,540,252 B1 | 1/2017 | Collins et al. | |

(Continued)

FOREIGN PATENT DOCUMENTS

| | | |
|---|---|---|
| CN | 101341095 A | 1/2009 |
| EP | 2 948 412 | 12/2015 |

(Continued)

OTHER PUBLICATIONS

Extended European Search Report, dated Feb. 22, 2021 by the European Patent Office (EPO), for Application No. 18835521.8.

(Continued)

*Primary Examiner* — Regina M Yoo
(74) *Attorney, Agent, or Firm* — Greenblum & Bernstein, P.L.C.

(57) ABSTRACT

One aspect described herein is a fluid treatment apparatus. The apparatus may comprise a body extending along a flow path between a first end and a second end opposite of the first end along the flow path, the first end comprising an inlet along the flow path, the second end comprising an outlet along the flow path; a flow channel extending inside the body along the flow path to direct a fluid from the inlet to the outlet; and a solid-state radiation source mountable in a cavity of the flow channel to emit radiation into the flow channel along the flow path, the solid-state radiation source comprising a thermally conductive portion positioned to be contacted by the fluid when the fluid is flowing from the inlet to the outlet and the solid-state radiation source is mounted (Continued)

in the cavity. Related apparatus, devices, and methods also are described.

36 Claims, 23 Drawing Sheets

(51) Int. Cl.
*A61L 9/20* (2006.01)
*C02F 1/32* (2023.01)

(52) U.S. Cl.
CPC ...... *A61L 2202/11* (2013.01); *A61L 2202/122* (2013.01); *A61L 2209/12* (2013.01); *C02F 2201/3222* (2013.01); *C02F 2201/3227* (2013.01); *C02F 2201/3228* (2013.01); *C02F 2303/04* (2013.01)

(58) Field of Classification Search
CPC .............. C02F 1/325; C02F 2201/3222; C02F 2201/3227; C02F 2201/3228; C02F 2303/04; B01J 2219/00164; B01J 2219/0877; B01J 2219/0892; B01J 19/244; B01J 19/123
See application file for complete search history.

(56) References Cited

U.S. PATENT DOCUMENTS

| | | | | |
|---|---|---|---|---|
| 9,630,859 | B2 † | 4/2017 | Chen | |
| 9,938,165 | B2 | 4/2018 | Taghipour | |
| 10,294,124 | B2 † | 5/2019 | Khan | |
| 10,376,608 | B1 | 8/2019 | Collins et al. | |
| 10,377,643 | B1 | 8/2019 | Collins et al. | |
| 11,452,792 | B2 * | 9/2022 | Kim | A61L 9/205 |
| 2012/0262921 | A1 * | 10/2012 | Boomgaarden | F21K 9/235 362/249.02 |
| 2015/0060693 | A1 | 3/2015 | Lee et al. | |
| 2015/0062909 | A1 | 3/2015 | Progl et al. | |
| 2015/0114912 | A1 * | 4/2015 | Taghipour | C02F 1/725 210/748.14 |
| 2015/0314024 | A1 | 11/2015 | Khan et al. | |
| 2015/0336810 | A1 | 11/2015 | Smetona et al. | |
| 2015/0359922 | A1 * | 12/2015 | Kim | A61L 9/20 422/121 |
| 2017/0072078 | A1 | 3/2017 | Lee et al. | |
| 2017/0217791 | A1 | 8/2017 | McNulty | |
| 2018/0201521 | A1 | 7/2018 | Taghipour | |
| 2018/0333510 | A1 | 11/2018 | Lee et al. | |
| 2018/0346349 | A1 | 12/2018 | Smetona et al. | |
| 2020/0138991 | A1 | 5/2020 | Lee et al. | |

FOREIGN PATENT DOCUMENTS

| | | | | |
|---|---|---|---|---|
| WO | 2007/029244 | A2 | 3/2007 | |
| WO | 2016/016603 | A1 | 2/2016 | |
| WO | 2017/055093 | A1 | 4/2017 | |
| WO | WO-2017124190 | A1 * | 7/2017 | B01J 19/123 |
| WO | WO-2017124191 | A1 * | 7/2017 | C02F 1/325 |

OTHER PUBLICATIONS

Chinese Office Action (including English Language Translation), dated Jul. 7, 2021, in related Chinese Patent Application No. 201880059220.8.
Chinese Office Action, dated Jul. 7, 2021, in related Chinese Patent Application No. 201880059220.8.
Second Chinese Office Action (including English Language Translation), dated Mar. 30, 2022, in related Chinese Patent Application No. 201880059220.8.
International Search Report, mailed Oct. 2, 2018, in International Application No. PCT/CA2018/050879.
Third Chinese Office Action (including English Language Translation), dated Aug. 24, 2022, in related Chinese Patent Application No. 201880059220.8.

* cited by examiner
† cited by third party

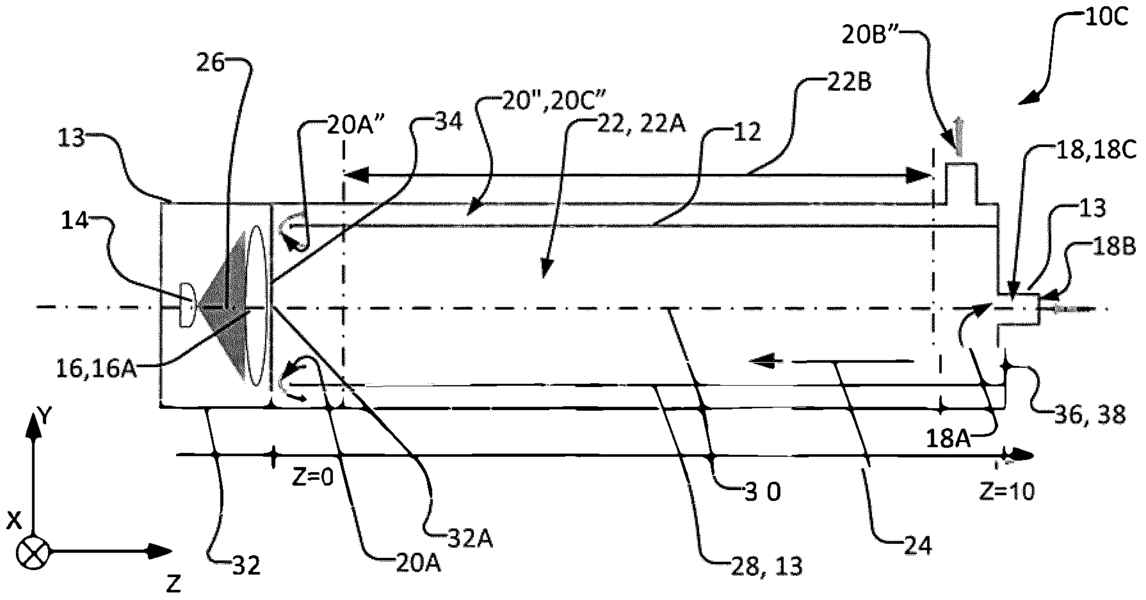
FIGURE 1C
FIGURE 1C
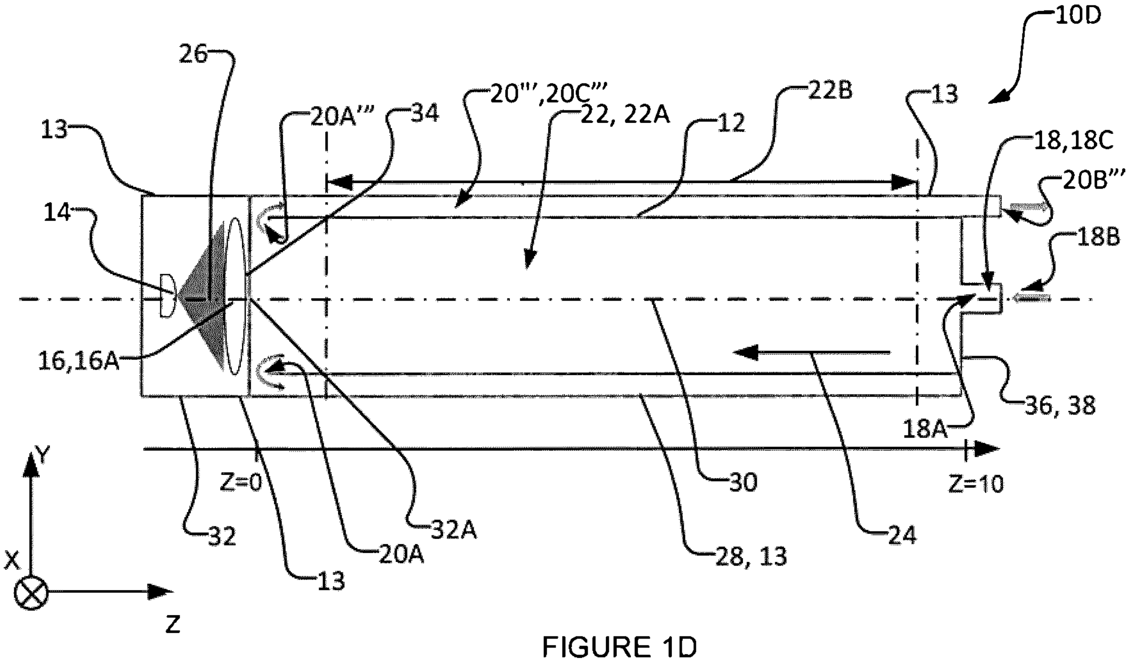
FIGURE 1D

UV-LED PHOTOREACTORS WITH CONTROLLED RADIATION AND HYDRODYNAMICS AND METHODS FOR FABRICATION AND USE OF SAME

TECHNICAL FIELD

The present invention relates to ultraviolet (UV) photoreactors, and more particularly, to a UV reactor operating with one or more ultraviolet light emitting diodes (UV-LEDs). Particular embodiments provide methods and apparatus for enhancing dose uniformity delivered to fluids moving through UV-LED photoreactors.

BACKGROUND

Ultraviolet (UV) reactors—reactors that administer UV radiation—are applied to many photoreactions, photocatalytic reactions, and photo-initiated reactions. One application for UV reactors is for water and air purification. In particular, UV reactors have emerged in recent years as one of the most promising technologies for water treatment. Prior art UV reactor systems typically use low- and medium-pressure mercury lamps to generate UV radiation.

Light emitting diodes (LEDs) typically emit radiation of such narrow bandwidth that radiation emitted by LEDs may be considered (for many applications) to be monochromatic (i.e. of a single wavelength). With recent advances in LED technology, LEDs may be designed to generate UV radiation at different wavelengths, which include wavelengths for DNA absorption as well as wavelengths that can be used for photocatalyst activation.

UV-LED reactors may generally be used for irradiating fluids, with applications such as water disinfection. However, in a typical UV-LED reactor, there is considerable variation of the radiant power distribution, resulting in uneven radiant fluence rate distribution, which may be quite significant in some cases. Fluence rate (in $W/m^2$) is the radiant flux (power) passing from all directions through an infinitesimally small sphere of cross-sectional area dA, divided by dA. Further, there is typically variation in the fluid velocity distribution, causing a residence time distribution of fluid as the fluid travels through the reactor. Either of these two phenomena of fluence rate distribution and velocity distribution, or a combination of these two phenomena, may result in a considerably wide range of UV dose distribution delivered to fluid elements, as they pass through the reactor. The variation in UV fluence rate distribution and velocity distribution (the velocity distribution being related to residence time distribution) may cause part of the fluid to traverse a UV reactor without receiving sufficient UV dose (a product of UV fluence rate and residence time), which is a known issue in the field of UV reactors and may be referred to as "short-circuiting". Short-circuiting can have a significantly unfavorable impact on the performance of a UV reactor.

There is a general desire to increase or enhance dose uniformity delivered to fluid as it passes through a UV reactor.

The foregoing examples of the related art and limitations related thereto are intended to be illustrative and not exclusive. Other limitations of the related art will become apparent to those of skill in the art upon a reading of the specification and a study of the drawings.

SUMMARY

The following aspects are described and illustrated in conjunction with systems, tools and methods which are meant to be exemplary and illustrative, not limiting in scope. In some aspects, one or more of the above-described problems have been reduced or eliminated, while other aspects are directed to other improvements.

One aspect of the invention provides a UV-LED reactor with control of both the fluidic and optical environments. The UV-LED reactor may advantageously provide radiation dose having a high degree of uniformity (relative to prior art UV reactors) to a fluid flow at a small footprint and may advantageously provide for a more efficient and compact UV-LED reactor than at least some prior art reactors. The UV-LED reactor may be incorporated into devices for various UV photoreaction applications, including, for example, UV-based water treatment and/or the like (as explained in further detail below).

One aspect of the present disclosure provides an ultraviolet (UV) reactor comprising a fluid conduit defined at least in part by an outer conduit-defining wall for permitting a fluid flow therethrough; a solid-state UV emitter (e.g. ultraviolet light emitting diode or UV-LED); and a radiation-focusing element comprising one or more lenses. The fluid conduit may comprise a fluid inlet and a fluid outlet and a longitudinally extending fluid flow channel located between the inlet and the outlet. The fluid flow channel may extend in a longitudinal direction for permitting the fluid flow in a longitudinal direction through a bore of the fluid flow channel. The fluid flow channel may have a central channel axis that extends in the longitudinal direction through centroids of transverse cross-sections of the bore in at least a longitudinally central portion of the bore. The one or more lenses may be positioned in a radiation path of radiation emitted from the solid-state UV emitter for directing radiation from the solid-state UV emitter to impinge in the fluid flow channel and to thereby provide a radiation fluence rate profile within a bore of the fluid flow channel. The one or more lenses may be configured to provide the radiation fluence rate profile wherein, when the solid-state UV emitter is emitting radiation, for cross-sections of the bore of the fluid flow channel located relatively close to the solid-state UV emitter (e.g. for a first cross-section), the radiation fluence rate profile is relatively high at locations that are relatively far from a central channel axis (i.e. a central axis of the bore of the fluid flow channel or at least the longitudinally central portion of the bore of the fluid flow channel) and relatively low at locations nearer to the central channel axis and wherein, for cross-sections of the bore of the fluid flow channel located relatively distal from the solid-state UV emitter (e.g. for a second cross-section located more distal from the solid-state UV emitter than the first cross-section), the radiation fluence rate profile is relatively low at locations that are relatively far from the central channel axis and relatively high at locations nearer to the central channel axis.

Another aspect of this disclosure is an ultraviolet (UV) reactor comprising: a fluid conduit defined at least in part by an outer conduit-defining wall for permitting a fluid flow therethrough; a solid-state UV emitter (e.g. ultraviolet light emitting diode or UV-LED); and a radiation-focusing element comprising one or more lenses; wherein the fluid conduit comprises a fluid inlet, a fluid outlet and a longitudinally extending fluid flow channel located between the inlet and the outlet, the fluid flow channel extending in a longitudinal direction for permitting the fluid flow in a longitudinal direction through a bore of the fluid flow channel; wherein the one or more lenses are positioned in a radiation path of radiation emitted from the solid-state UV emitter for directing radiation from the solid-state UV emitter to impinge in the fluid flow channel and to thereby provide a radiation fluence rate profile within a bore of the fluid flow channel; and wherein the solid-state UV emitter having a central optical axis in the radiation path of the UV emitter that extends in the longitudinal direction from centroid of emission region of the solid-state UV emitter through centroids of one or more optical lenses, and when the solid-state UV emitter is emitting radiation: for locations in the radiation path of the solid-state UV emitter that are relatively close to the solid-state UV emitter, the radiation fluence rate profile is relatively high at locations that are relatively far from the central optical axis and relatively low at locations nearer to the central optical axis; and for locations in the radiation path of the solid-state UV emitter that are relatively distal from the solid-state UV emitter the radiation fluence rate profile is relatively low at locations that are relatively far from the central optical axis and relatively high at locations nearer to the central optical axis.

The solid-state UV emitter may comprise a plurality of solid-state emitters. The one or more lenses may be configured, by one or more of selection of the one or more lenses from among a variety of lens types, shape of the one or more lenses (e.g. thickness of the lenses and curvature of the lens surfaces), position of the one or more lenses and indices of refraction of the one or more lenses, to provide the radiation fluence rate profile having these characteristics. In some aspects, the lens(es) may comprise a converging lens optically adjacent to the UV emitter and a collimating lens at some suitable distance away from the converging lens. In some aspects, the lens(es) may comprise a converging lens located to receive radiation from the UV emitter and a collimating lens, where the collimating lens may be positioned at a distance less than its focal length (e.g. by a differential distance Δ) from the focal point of radiation emitted from the converging lens. In some aspects, the lens(es) may comprise a half-ball lens which receives radiation from the UV emitter and a plano-convex lens which receives radiation from the half-ball lens, with both of their planar sides facing the UV emitter and with both of their optical axes co-axial with the central channel axis. In some aspects, there is an air space between the plano-convex lens and the fluid in the bore of the fluid flow channel. In some aspects, there is an air space and a UV-transparent (e.g. quartz) window between the plano-convex lens and the fluid in the bore of the fluid flow channel.

In some aspects, the plano-convex lens may be positioned at a distance f', which is less than its inherent focal length f1, from the focal point of radiation emitted from the half-ball lens. The spacing (f') of the plano-convex lens relative to the focal point of the half-ball lens may be less than the inherent focal length (f1) of the plano-convex lens by a differential distance (A). In some aspects, this differential distance Δ is in a range of 10%-35% of the focal length f1 of the plano-convex lens. In some aspects, this differential distance Δ is in a range of 15%-30% of the focal length (f1) of the plano-convex lens. In some aspects, this this differential distance Δ is in a range of 20%-30% of the focal length (f1) of the plano-convex lens. The lens(es) may comprise any suitable combination of biconvex, biconcave, plano-convex, plano-concave, meniscus, or half-ball lens(es). The lenses may comprise a first lens (located closer to the UV emitter) and a second lens (located relatively far from the UV emitter). Radiation emitted from the first lens may have a focal point and the second lens may have an inherent focal length (f1), but the second lens may not be located at a distance (f1) from the focal point of the first lens. Instead, the second lens may be located at a distance (f') from the focal point of the first lens, where f' is less than f1 by a differential distance Δ. In some aspects, this differential distance Δ is in a range of 10%-35% of the focal length f1 of the second lens. In some aspects, this differential distance Δ is in a range of 15%-30% of the focal length f1 of second lens. In some aspects, this this differential distance Δ is in a range of 20%-30% of the focal length f1 of second lens.

The bore-defining wall may be shaped to define the bore of the fluid-flow channel to have a cylindrical shape over at least a longitudinally central portion of the fluid flow channel, the longitudinally central portion spaced apart from the fluid inlet and the fluid outlet. The cylindrical shape may comprise a cylinder with circular cross-section or a cylinder with some other (e.g. rectangular or some other polygonal) cross-section. The principal optical axis of the solid-state UV emitter (e.g. the principal optical axis of the LED), the optical axes of the one or more lenses and the central channel axis may be co-linear or co-axial. The fluid inlet may comprise one or more inlet apertures, where the fluid inlet opens into the fluid flow channel, one or more connecting apertures, through which UV reactor may be connected to an external fluid system which provides fluid to the reactor and one or more inlet conduits which may extend between the inlet apertures and the connecting apertures. Similarly, fluid outlet may comprise one or more outlet apertures, where the fluid outlet opens into the fluid flow channel, one or more connecting apertures, through which the UV reactor may be connected to an external output fluid system to which fluid flows from the reactor and one or more outlet conduits which may extend between the outlet apertures and the connecting apertures.

The solid-state UV emitter and the radiation-focusing element may be housed in a suitable housing which may comprise a UV-transparent component, such as a quartz window, for separating the electronics and optics from the fluid flow.

In some aspects, the solid-state UV emitter may be located relatively proximate to the fluid outlet and relatively distal from the fluid inlet, with the principal optical axis of the solid-state emitter being oriented generally antiparallel to the longitudinal fluid flow direction. The fluid conduit may comprise a cross-sectional wall at one end thereof, the cross-sectional wall may define an inlet aperture for the fluid inlet (where the fluid inlet opens into the fluid flow channel) or may otherwise support the fluid inlet. The inlet aperture and/or the fluid inlet may be centrally located in the cross-sectional wall. The central channel axis may project through the inlet aperture and/or the fluid inlet. A cross-section of inlet aperture and/or the fluid inlet may be circularly symmetric about a point that is located on the central channel axis. With the inlet aperture and/or fluid inlet exhibiting these properties, for cross-sections of the bore of the fluid flow channel located relatively distal from the solid-state UV emitter or close to the inlet aperture, the fluid velocity is relatively low at locations that are relatively far from the central channel axis and relatively high at locations relatively close to the central channel axis. The solid-state UV emitter may be supported in the housing such that the principal optical axis of the solid-state UV emitter is at least generally aligned with the central channel axis. In some aspects, the housing may itself be supported (e.g. by one or more brackets) such that the principal optical axis of the solid-state UV emitter is at least generally aligned with the central channel axis. The one or more brackets may extend from the outer conduit-defining wall of the fluid conduit to the housing. The one or more brackets may extend across the outlet conduit(s) of fluid outlet. An outlet aperture for the fluid outlet may be defined by a combination of the outer conduit-defining wall (possibly including the bore-defining wall), the housing and/or the one or more brackets (where present) or the fluid outlet may otherwise be supported by a combination of the outer conduit-defining wall (possibly including the bore-defining wall), the housing and/or the one or more brackets (where present). In some aspects, the outlet conduit of the fluid outlet may have generally annular cross-sections at locations between the outlet aperture(s) and the connecting aperture(s) wherein these cross-sections may be defined by the outer conduit-defining wall and the housing (except in regions where this annular shape is interrupted by the one or more brackets). This (generally annularly shaped cross-sections for the outlet conduit) is not necessary. With these configurations, the outlet aperture(s) may be located at location(s) that are spaced transversely apart from the central channel axis (e.g. as transversely far away as may be permitted by the bore of the fluid flow channel or by the fluid conduit generally). Consequently, with the outlet aperture and/or fluid outlet exhibiting these properties, for cross-sections of the bore of the fluid flow channel located relatively close to the solid-state UV emitter or close to the outlet aperture(s), the fluid velocity is relatively high at at least some locations relatively far from the central channel axis (e.g. at locations directly upstream from or adjacent to the outlet aperture(s)) and relatively low at locations relatively close to the central channel axis.

In some aspects, the solid-state UV emitter may be located relatively proximate to the fluid inlet and relatively distal from the fluid outlet, with the principal optical axis of the solid-state emitter being oriented generally parallel to the longitudinal fluid flow direction. The fluid conduit may comprise a cross-sectional wall at one end thereof, the cross-sectional wall may define an outlet aperture for the fluid outlet (where the fluid outlet opens into the fluid flow channel) or may otherwise support the fluid outlet. The outlet aperture and/or the fluid outlet may be centrally located in the cross-sectional wall. The central channel axis may project through the outlet aperture and/or the fluid outlet. A cross-section of outlet aperture and/or the fluid outlet may be circularly symmetric about a point that is located on the central channel axis. With the outlet aperture and/or fluid outlet exhibiting these properties, for cross-sections of the bore of the fluid flow channel located relatively close to the outlet aperture, the fluid velocity is relatively low at locations that are relatively far from the central channel axis and relatively high at locations relatively close to the central channel axis. The solid-state UV emitter may be supported in the housing such that the principal optical axis of the solid-state UV emitter is at least generally aligned with the central channel axis. In some aspects, the housing itself may itself be supported (e.g. by one or more brackets 40) such that the principal optical axis of the solid-state UV emitter is at least generally aligned with the central channel axis. The one or more brackets may extend from the outer conduit-defining wall of the fluid conduit to the housing. The one or more brackets may extend across the inlet conduit(s) of the fluid inlet. An inlet aperture for the fluid inlet may be defined by a combination of the outer conduit-defining wall (possibly including the bore-defining wall), the housing and/or the one or more brackets (where present) or the fluid inlet may otherwise be supported by a combination of the outer conduit-defining wall (possibly including the bore-defining wall), the housing and/or the one or more brackets (where present). In some aspects, the inlet conduit of the fluid inlet may have generally annular cross-sections at locations between the inlet aperture(s) and the connecting aperture(s) wherein these cross-sections may be defined by the outer conduit-defining wall and the housing (except in regions where this annular shape is interrupted by the one or more brackets). This (generally annularly shaped cross-sections for the inlet conduit) is not necessary. With these configurations, the inlet aperture(s) may be located at location(s) that are spaced transversely apart from the central channel axis (e.g. as transversely far away as may be permitted by the bore of the fluid flow channel or by the fluid conduit generally). Consequently, with the inlet aperture and/or fluid inlet exhibiting these properties, for cross-sections of the bore of the fluid flow channel located relatively close to the solid-state UV emitter or close to the inlet aperture(s), the fluid velocity is relatively high at at least some locations relatively far from the central channel axis (e.g. at locations directly downstream from or adjacent to the inlet aperture(s)) and relatively low at locations relatively close to the central channel axis.

The UV reactor may comprise one or more flow modifiers (e.g. static mixers or other types of flow modifiers) which may be located in the fluid flow channel. The flow modifiers may be located relatively proximate to the fluid inlet and may be shaped to use a momentum of the fluid flow to direct the fluid flow In some aspects, a flat or curved-shaped baffle or ring may be positioned in the path of the portion of the fluid heading toward regions of low radiation fluence rate to redirect the flow course or reduce flow velocity in the directions toward the regions of low radiation fluence rates, for at least part of the fluid flow. Such flow modifiers may thereby cause, over a portion of the fluid flow channel, relatively low fluid velocities in regions of the fluid flow channel where there are relatively low radiation fluence rates and/or generate flow mixing between the regions of the fluid flow channel where there are relatively low and relatively high radiation fluence rates. Where the inlet aperture and/or the fluid inlet is centrally located in the cross-sectional wall, the one or more flow modifiers may be located in a region of the fluid flow channel where there is fluid flow expansion (e.g. from the inlet with a cross section smaller than that of the longitudinally central portion) and may use the flow momentum, which is a result of relatively high velocity at the inlet or the regions of the fluid flow channel near the inlet. In these regions, a flat or curved shape baffle or ring may be positioned in the path of the portion of the fluid heading toward the regions of low radiation fluence rate to redirect the flow course or reduce flow velocity in the directions toward the regions of low radiation fluence rates, for at least part of the fluid flow. Such flow modifiers may thereby cause, over a portion of the fluid flow channel, relatively low fluid velocities in the regions of the fluid flow channel where there are relatively low radiation fluence rates and/or generate flow mixing between the regions of the fluid flow channel where there are relatively low and relatively high radiation fluence rates. A flow modifier in the form of a static mixer may result in the formation of a vortex or vortices in the fluid flow. For example, counter-rotating vortices in the fluid flow channel may be generated, as a result of positioning a delta wing shaped mixer and/or a twisted tape shaped mixer in the path of the fluid flow.

The flow modifiers may comprise one or more static mixers which may in turn comprise one or a combination several delta wing shaped mixers and/or twisted tape shaped mixers adjacent to each other. The delta wing shaped mixers and/or twisted tap shaped mixers may be connected to each other at some parts; for example, at the base or vertex. The generation of a vortex or vortices, in particular counter-rotating vortices, over a portion of the fluid flow channel may provide mixing of the fluid flow and may cause the same part of the fluid to travel in the regions of both higher and lower radiation fluence rates. In some aspects, one or more flow modifiers may be applied to prevent the fluid from flowing at high velocities in the regions of the fluid flow channel having low fluence rates or to redirect the flow from these regions of the fluid flow channel having low fluence rates to the regions of the fluid flow channel having higher fluence rates. For example, if the fluence rates in some regions of the fluid flow channel near the bore-defining wall are low, a ring which projects from the bore-defining wall toward the central channel axis can be provided to redirect the fluid flow toward the central channel axis and to enhance mixing. In some aspects, one or more flow modifiers may be placed at regions of the fluid flow channel where there are low radiation fluence rates, for example near the conduit-defining wall (e.g. near the bore-defining wall) at some parts of the conduit 12, or in the fluid inlet. Configuring flow modifiers (e.g. static mixers) in regions of the fluid flow channel having low fluence rates may result in minimizing the impact of the flow modifier on blocking UV radiation. In some aspects, flow modifiers may be made of UV reflective materials. In some aspects, flow modifiers can be made of UV transparent materials.

The UV reactor may comprise a second solid-state UV emitter; and a second radiation-focusing element comprising one or more secondary lenses. The one or more secondary lenses may be positioned in a second radiation path of radiation emitted from the second solid-state UV emitter for directing radiation from the second solid-state UV emitter to impinge on the fluid flowing in the fluid flow channel and to thereby provide a second radiation fluence rate profile within the bore of the fluid flow channel. The one or more secondary lenses may be configured to provide the second radiation fluence rate profile wherein, for secondary cross-sections of the bore of the fluid flow channel located relatively close to the second solid-state UV emitter (e.g. for a first secondary cross-section), the second radiation fluence rate profile is relatively high at locations that are relatively far from the central channel axis and relatively low at locations nearer to the central channel axis and wherein, for secondary cross-sections of the bore of the fluid flow channel located relatively distal from the second solid-state UV emitter (e.g. for a second secondary cross-section located more distal from the second solid-state UV emitter than the first secondary cross-section), the second radiation fluence rate profile is relatively low at locations that are relatively far from the central channel axis and relatively high at locations that are nearer to the central channel axis. A principal optical axis of the second solid-state UV emitter may be anti-parallel to the principal optical axis of the (first) solid-state UV emitter. The principal optical axis of the (first) solid-state UV emitter (e.g. the principal optical axis of the first LED), the principal optical axis of the second solid-state UV emitter (e.g. the principal optical axis of the second LED), the optical axes of the one or more lenses, the optical axes of the one or more secondary lenses and a central axis of at least the longitudinally central portion of the fluid flow channel may be co-linear or co-axial. The second solid-state UV emitter, the second radiation focusing element and the one or more secondary lenses may comprise any of the features of the solid-state emitter, the radiation focusing element and the one or more lenses.

In some aspects, the fluid outlet may comprise a fluid outlet conduit which may be defined in part by or otherwise in direct or indirect thermal contact with the housing, which in turn may be in direct or indirect (e.g. via a printed circuit board (PCB)) thermal contact with the solid-state UV emitter (i.e. on transverse side(s) of the housing or portions thereof and a side of the solid-state UV emitter opposing the principal optical axis of the solid-state UV emitter or a portion thereof) for removing heat from the solid-state UV emitter and transferring such heat to the fluid. In some aspects, the fluid outlet may comprise a fluid outlet conduit which is otherwise in direct or indirect (e.g. via a printed circuit board (PCB)) thermal contact with the solid-state UV emitter for removing heat from the solid-state UV emitter and transferring such heat to the fluid. In some aspects, a printed circuit board (PCB) on which the UV emitter is mounted may provide a wall of the housing and/or the outlet conduit or a portion thereof so that the fluid is in direct thermal contact with the PCB on which the UV emitter is mounted. This heat removal may be particularly effective because of the high degree of mixing as a result of flow contraction and sudden change in the fluid velocity when the fluid flow is directed from the bore of the fluid flow channel into the relatively narrow fluid outlet. In some aspects, the fluid inlet may comprise a fluid inlet conduit which may be defined in part by or otherwise in direct or indirect thermal contact with the housing, which in turn may be in direct or indirect (e.g. via a printed circuit board (PCB)) thermal contact with the solid-state UV emitter (i.e. on transverse side(s) of the housing or portions thereof and/or on a side of the solid-state UV emitter opposing the principal optical axis of the solid-state UV emitter or a portion thereof) for removing heat from the solid-state UV emitter and transferring such heat to the fluid. In some aspects, the fluid inlet may comprise a fluid inlet conduit which is otherwise in direct or indirect (e.g. via a printed circuit board (PCB)) thermal contact with the solid-state UV emitter for removing heat from the solid-state UV emitter and transferring such heat to the fluid. In some aspects, a printed circuit board (PCB) on which the UV emitter is mounted may provide a wall of the housing and/or the inlet conduit or a portion thereof so that the fluid is in direct thermal contact with the PCB on which the UV emitter is mounted. This heat removal may be particularly effective because of the high degree of mixing as a result of the flow expansion and sudden change in fluid velocity that occurs when the fluid flow is directed from the narrow fluid inlet into the relatively side bore of the fluid flow channel. This heat transfer (from the surrounding wall of the housing or portions thereof) may be particularly effective as a result of heat being removed from many surfaces of the housing and the corresponding surface area. Also, by controlling the cross-section of the inlet/outlet conduit, higher fluid velocities can be achieved near the housing walls to further enhance heat transfer.

In some aspects, the reactor may comprise an array of longitudinally extending fluid flow channels, any number of which may comprise properties similar to the longitudinally extending fluid flow channel described herein. In some aspects, each such fluid flow channel can be irradiated by one or more corresponding solid-state UV emitters through a corresponding radiation-focusing element. The corresponding solid-state UV emitters and/or the corresponding radiation-focusing elements may be positioned at longitudinal ends of their corresponding longitudinally-extending fluid flow channels so that a direction of irradiation is generally parallel to and opposing the direction of the fluid flow, while providing corresponding radiation fluence rate profiles having the features described herein. Specifically, for cross-sections of the bore of each fluid flow channel located relatively close to the solid-state UV emitter, the radiation fluence rate profile is relatively high at locations further from the central channel axis of the fluid flow channel and relatively low at locations nearer to the central channel axis and wherein, for cross-sections of the bore of each fluid flow channel located relatively distal from the solid-state UV emitter, the radiation fluence rate profile is relatively low at locations further from the central channel axis of the fluid flow channel and relatively high at locations nearer to the central channel axis.

The reactor may comprise a plurality of UV-LEDs that emit different UV wavelengths. The reactor may comprise a photocatalyst supported on a structure in the reactor. The reactor may comprise a chemical reagent that is added to the reactor. The UV-LED may be turned on and off automatically by an external signal.

Another aspect of this disclosure is a method for using an ultraviolet (UV) reactor for irradiating a fluid travelling through the reactor with UV radiation to thereby treat the fluid. The method comprises providing a UV reactor comprising a fluid conduit defined at least in part by an outer conduit-defining wall for permitting a fluid flow therethrough; a solid-state UV emitter (e.g. ultraviolet light emitting diode or UV-LED); and a radiation-focusing element comprising one or more lenses. The method comprises introducing the fluid into a longitudinally extending fluid flow channel via a fluid inlet, allowing the fluid to flow through the longitudinally extending fluid flow channel in a longitudinal direction and removing the fluid from the fluid flow channel via a fluid outlet, the fluid outlet located at a longitudinally opposite end of the fluid flow channel from the inlet. The method comprises directing radiation from the solid-state UV emitter through the one or more lenses and thereby causing the radiation to impinge on the fluid flowing in the fluid flow channel and to thereby provide a radiation fluence rate profile within a bore of the fluid flow channel. The one or more lenses may be configured to provide the radiation fluence rate profile wherein, for cross-sections of the bore of the fluid flow channel located relatively close to the solid-state UV emitter (e.g. for a first cross-section), the radiation fluence rate profile is relatively high at locations that are relatively far from a central channel axis (i.e. a central axis of the bore of the fluid flow channel or at least the longitudinally central portion of the bore of the fluid flow channel) and relatively low at locations that are relatively close to the central channel axis and wherein, for cross-sections of the bore of the fluid flow channel located relatively distal from the solid-state UV emitter (e.g. for a second cross-section located more distal from the solid-state UV emitter than the first cross-section), the radiation fluence rate profile is relatively low at locations that are relatively far from the central channel axis and relatively high at locations that are nearer to the central channel axis.

The method may comprise using any of the features of the UV-reactors described herein.

Another aspect of this disclosure is an ultraviolet (UV) reactor for irradiating a flow of fluid with UV radiation, the UV reactor comprising: a fluid conduit defined at least in part by an outer conduit-defining wall for permitting a fluid flow therethrough; a first solid-state UV emitter (e.g. ultraviolet light emitting diode or UV-LED); a first radiation-focusing element comprising one or more first lenses; a second solid-state UV emitter; and a second radiation-focusing element comprising one or more second lenses. The fluid conduit comprises a fluid inlet, a fluid outlet and a longitudinally extending fluid flow channel located between the inlet and the outlet, the fluid flow channel extending in a longitudinal direction for permitting the fluid flow in a longitudinal direction through a bore of the fluid flow channel and the fluid flow channel having a central channel axis that extends in the longitudinal direction through centroids of transverse cross-sections of the bore in at least a longitudinally central portion of the bore. The one or more first lenses are positioned in a radiation path of first radiation emitted from the first solid-state UV emitter for directing the first radiation from the first solid-state UV emitter to impinge on the fluid flowing in the fluid flow channel from an outlet end of the fluid flow channel in a direction generally opposed to the longitudinal direction of fluid flow. The one or more second lenses are positioned in a radiation path of second radiation emitted from the second solid-state UV emitter for directing the second radiation from the second solid-state UV emitter to impinge on the fluid flowing in the fluid flow channel from an inlet end of the fluid flow channel in a direction generally aligned with and in the same direction as the longitudinal direction of fluid flow. The reactor comprises: a first housing for supporting the first solid-state UV emitter such that a principal optical axis of the first solid-state UV emitter is at least generally co-axial with the central channel axis and wherein an outlet aperture for the fluid outlet, where the fluid outlet opens into the bore of the fluid flow channel, is defined by a combination of the outer conduit-defining wall and the first housing; and a second housing for supporting the second solid-state UV emitter such that a principal optical axis of the second solid-state UV emitter is at least generally co-axial with the central channel axis and wherein an inlet aperture for the fluid inlet, where the fluid inlet opens into the bore of the fluid flow channel, is defined by a combination of the outer conduit-defining wall and the second housing.

The UV reactor may comprise any of the features of the UV reactors described herein.

Another aspect of this disclosure is a method for using an ultraviolet (UV) reactor for irradiating a fluid travelling through the reactor with UV radiation to thereby treat the fluid. The method comprises: providing a UV reactor comprising a fluid conduit defined at least in part by an outer conduit-defining wall for permitting a fluid flow therethrough; a first solid-state UV emitter (e.g. ultraviolet light emitting diode or UV-LED); a first radiation-focusing element comprising one or more first lenses; a second solid-state UV emitter; and a second radiation-focusing element comprising one or more second lenses; introducing the fluid into a bore of a longitudinally extending fluid flow channel via a fluid inlet, allowing the fluid to flow through the longitudinally extending fluid flow channel in a longitudinal direction and removing the fluid from the fluid flow channel via a fluid outlet, the fluid outlet located at a longitudinally opposite end of the fluid flow channel from the inlet, wherein the fluid flow channel has a central channel axis that extends in the longitudinal direction through centroids of transverse cross-sections of the bore in at least a longitudinally central portion of the bore; directing first radiation from the first solid-state UV emitter through the one or more first lenses and thereby causing the first radiation to impinge on the fluid flowing in the fluid flow channel from an outlet end of the fluid flow channel in a direction generally opposed to the longitudinal direction of fluid flow; directing second radiation from the second solid-state UV emitter through the one or more secondary lenses and thereby causing the second radiation to impinge on the fluid flowing in the fluid flow channel from an inlet end of the fluid flow channel in a direction generally aligned with and in the same direction as the longitudinal direction of fluid flow; supporting the first solid-state UV emitter in a first housing such that a principal optical axis of the first solid-state UV emitter is at least generally co-axial with the central channel axis and wherein an outlet aperture for the fluid outlet, where the fluid outlet opens into the bore of the fluid flow channel, is defined by a combination of the outer conduit-defining wall and the first housing; and. supporting the second solid-state UV emitter in a second housing such that a principal optical axis of the second solid-state UV emitter is at least generally co-axial with the central channel axis and wherein an inlet aperture for the fluid inlet, where the fluid inlet opens into the bore of the fluid flow channel, is defined by a combination of the outer conduit-defining wall and the second housing.

The method may comprise installing the UV reactor in an existing fluid flow conduit that extends in a first direction. Installing the UV reactor in the existing fluid flow conduit may comprise: removing a section of the existing conduit from the existing conduit to expose an upstream portion of the existing conduit and a downstream portion of the existing conduit, the upstream portion and downstream portion generally aligned with one another in the first direction; connecting the fluid inlet of the UV reactor to an end of the upstream portion of the existing conduit; and connecting the fluid outlet of the UV reactor to an end of the downstream portion of the existing conduit. Connecting the fluid inlet of the UV reactor to the end of the upstream portion of the existing conduit and connecting the fluid outlet of the UV reactor to the end of the downstream portion of the existing conduit may together comprise aligning the longitudinal direction of fluid flow with the first direction.

The method may comprise using any of the features of the UV-reactors described herein.

Another aspect of this disclosure is and ultraviolet (UV) reactor for irradiating a flow of fluid with UV radiation. The reactor comprises: a fluid conduit defined at least in part by an outer conduit-defining wall for permitting a fluid flow therethrough; a solid-state UV emitter (e.g. ultraviolet light emitting diode or UV-LED); and a radiation-focusing element comprising one or more lenses. The fluid conduit comprises a fluid inlet, a fluid outlet and a longitudinally extending fluid flow channel located between the inlet and the outlet. The fluid flow channel extends in a longitudinal direction for permitting the fluid flow in a longitudinal direction through a bore of the fluid flow channel. The fluid flow channel has a central channel axis that extends in the longitudinal direction through centroids of transverse cross-sections of the bore in at least a longitudinally central portion of the bore. The one or more lenses are positioned in a radiation path of radiation emitted from the solid-state UV emitter for directing radiation from the solid-state UV emitter to impinge on the fluid flowing in the fluid flow channel and to thereby provide a radiation fluence rate profile within the bore of the fluid flow channel. The one or more lenses may comprise a half-ball lens positioned to receive radiation from the UV emitter and a plano-convex lens or a Fresnel lens positioned to receive radiation from the half-ball lens. The half-ball lens and plano-convex lens or Fresnel lens may have their planar sides facing the UV emitter. The solid-state UV emitter, the half-ball lens and the plano-convex lens or the Fresnel lens may have their optical axes parallel with, and in some cases co-axial with, the central channel axis.

The plano-convex lens may be positioned at a distance f', which is less than its inherent focal length f1, from a focal point of radiation emitted from the half-ball lens. A distance/spacing f' of the plano-convex lens relative to the focal point of the half-ball lens may be less than the inherent focal length f1 of the plano-convex lens by a differential distance Δ. The differential distance Δ may be in a range of 10%-35% of the focal length f1 of the plano-convex lens. The differential distance Δ may be in a range of 15%-30% of the focal length f1 of the plano-convex lens. The differential distance Δ may be in a range of 20%-30% of the focal length f1 of the plano-convex lens.

The UV reactor may comprise a second solid-state UV emitter having a secondary principal optical axis that is oriented anti-parallel to the principal optical axis of the solid-state UV emitter; and a second radiation-focusing element comprising one or more secondary lenses positioned in a second radiation path of radiation emitted from the second solid-state UV emitter for directing radiation from the second solid-state UV emitter to impinge on the fluid flowing in the fluid flow channel and to thereby provide a second radiation fluence rate profile within the bore of the fluid flow channel. The one or more secondary lenses may comprise a secondary half-ball lens positioned to receive radiation from the second UV emitter and a secondary plano-convex lens positioned to receive radiation from the secondary half-ball lens. Both the secondary half-ball lens and secondary plano-convex lens may have their planar sides facing the second UV emitter. The second solid state UV emitter, the secondary half-ball lens and the secondary plano-convex lens may have their optical axes parallel with, and in some cases co-axial with, the central channel axis. The secondary plano-convex lens may be positioned at a second distance f2', which is less than its inherent focal length f2, from a focal point of radiation emitted from the secondary half-ball lens. The second spacing/distance f2' of the secondary plano-convex lens relative to the focal point of the secondary half-ball lens may be less than the inherent focal length f2 of the second plano-convex lens by a second differential distance Δ2. The second differential distance Δ2 may be in a range of 10%-35% of the focal length f2 of the secondary plano-convex lens. The second differential distance Δ2 may be in a range of 15%-30% of the focal length f2 of the secondary plano-convex lens. The second differential distance Δ2 may be in a range of 20%-30% of the focal length f2 of the secondary plano-convex lens.

The UV reactor may comprise any of the features of the UV reactors described herein.

Another aspect of this disclosure is a method for using an ultraviolet (UV) reactor for irradiating a fluid travelling through the reactor with UV radiation to thereby treat the fluid. The method comprises: providing a UV reactor comprising a fluid conduit defined at least in part by an outer conduit-defining wall for permitting a fluid flow therethrough, a solid-state UV emitter (e.g. ultraviolet light emitting diode or UV-LED), and a radiation-focusing element comprising one or more lenses; introducing the fluid into a bore of a longitudinally extending fluid flow channel via a fluid inlet, allowing the fluid to flow through the longitudinally extending fluid flow channel in a longitudinal direction and removing the fluid from the fluid flow channel via a fluid outlet, the fluid outlet located at a longitudinally opposite end of the fluid flow channel from the inlet, wherein the fluid flow channel has a central channel axis that extends in the longitudinal direction through centroids of transverse cross-sections of the bore in at least a longitudinally central portion of the bore; directing radiation from the solid-state UV emitter through the one or more lenses and thereby causing the radiation to impinge on the fluid flowing in the fluid flow channel and to thereby provide a radiation fluence rate profile within the bore of the fluid flow channel; wherein the one or more lenses comprise a half-ball lens and a plano-convex lens and the method comprises: positioning the half-ball lens to receive radiation from the UV emitter, positioning the plano-convex lens to receive radiation from the half-ball lens, orienting both the half-ball lens and plano-convex lens to have their planar sides facing the UV emitter and aligning the solid state UV emitter, the half-ball lens and the plano-convex lens to have their optical axes parallel with, and in some cases co-axial with, the central channel axis.

The method may comprise using any of the features of the UV-reactors described herein.

Another aspect of this disclosure is a method for using the UV reactor of any of the other claims herein by installing the UV reactor in an existing fluid flow conduit that extends in a first direction. Installing the UV reactor in the existing fluid flow conduit comprises: removing a section of the existing conduit from the existing conduit to expose an upstream portion of the existing conduit and a downstream portion of the existing conduit, the upstream portion and downstream portion generally aligned with one another in the first direction; connecting the fluid inlet of the UV reactor to an end of the upstream portion of the existing conduit; and connecting the fluid outlet of the UV reactor to an end of the downstream portion of the existing conduit; wherein connecting the fluid inlet of the UV reactor to the end of the upstream portion of the existing conduit and connecting the fluid outlet of the UV reactor to the end of the downstream portion of the existing conduit together comprise aligning the longitudinal direction of fluid flow with the first direction.

Another aspect of this disclosure is a fluid treatment apparatus comprising: a body extending along a flow path between a first end and a second end opposite of the first end along the flow path, the first end comprising an inlet along the flow path, the second end comprising an outlet along the flow path; a flow channel extending inside the body along the flow path to direct a fluid from the inlet to the outlet; and a solid-state radiation source mountable in a cavity of the flow channel to emit radiation into the flow channel along the flow path, the solid-state radiation source comprising a thermally conductive portion positioned to be contacted by the fluid when the fluid is flowing from the inlet to the outlet and the solid-state radiation source is mounted in the cavity.

The solid-state radiation source may include a solid-state UV emitter. The apparatus may further comprise a one or more lenses positionable to refract the radiation from the solid-state radiation source. For example, the one or more lenses may be configured to correlate intensities of the radiation at a location in the flow channel with velocities of the fluid at the location in the flow channel when the fluid is flowing from the inlet to the outlet and the solid-state radiation source is mounted in the cavity. The cavity may be defined by interior surfaces of the flow channel that are configured to cause the fluid to flow around the solid-state radiation source and in contact with the thermally conductive portion of the solid-state radiation source when the fluid is flowing from the inlet to the outlet and the solid-state radiation source is mounted in the cavity. For example, the interior surfaces of the cavity may be engageable with exterior surfaces of the solid-state radiation source to maintain a position of the solid-state radiation source relative to the flow channel when the fluid is flowing from the inlet to the outlet and the solid-state radiation source is mounted in the cavity.

The apparatus may further comprise a mounting structure extending between the interior surfaces of the cavity and the exterior surfaces of the optical unit to maintain the position of the solid-state radiation source. For example, the mounting structure may extend along the flow path and include portions that are spaced apart peripherally about the flow path to define a plurality of flow channels extending along the flow path and in contact with the thermally conductive portion when the solid-state radiation source is positioned in the cavity. Each flow path may modify a velocity of the fluid flowing therethrough. In some aspects, the exterior surfaces of the solid-state radiation source may include exterior surfaces of the thermally conductive portion of the solid-state radiation source; and the mounting structure may not extend to the thermally conductive portion of the solid-state radiation source when the solid-state radiation source is positioned in the cavity to prevent heat transfer between the thermally conductive portion of the solid-state radiation source, the body, and the fluid when the fluid flows from the inlet to the outlet. Alternatively, the exterior surfaces of the solid-state radiation source may include exterior surfaces of the thermally conductive portion of the solid-state radiation source; and the mounting structure may extend to the exterior surfaces of the thermally conductive portion to permit heat transfer between the thermally conductive portion of the solid-state radiation source, the body, and the fluid when the fluid flows from the inlet to the outlet. For example, one or more of the mounting structure, the interior surfaces of the cavity, and/or the thermally conductive portion of the solid-state radiation source may include a metallic material.

In some aspects, the solid-state radiation source may be contained in an optical unit comprising the thermally conductive portion and one or more lenses positionable to refract the radiation from the solid-state radiation source and/or the optical unit may be removably mountable in the cavity. For example, the apparatus may further comprise a mounting structure extending between the interior surfaces of the cavity and the exterior surfaces of the optical unit to maintain a position of the optical unit relative to the flow channel when the fluid is flowing from the inlet to the outlet and the optical unit is mounted in the cavity. The thermally conductive portion of the optical unit may be spaced apart from the interior surfaces of the cavity when the optical unit is mounted in the cavity. For example, the body may comprise a socket, and the socket may comprise: a first end portion; a second end portion; and a coupler engageable with the first end portion and the second end portion to define the cavity. The optical unit may be removably positionable in the cavity when the ring is engaged with the socket. For example, the optical unit may be removably mountable and/or positionable in the second end portion of the socket and/or the inlet and the outlet may be mounted in-line with a pipe.

In some aspects, the cavity may be a first cavity, the solid-state radiation source may be a first solid-state radiation source, the radiation may be a first radiation, the flow channel may define a second cavity, and the apparatus may further comprise: a second solid-state radiation source mountable in the second cavity to emit a second radiation into the flow channel along the flow path, the second solid-state radiation source comprising a thermally conductive portion positioned to be contacted by the fluid when the fluid is flowing from the inlet to the outlet and the second solid-state radiation source is mounted in the second cavity. In some aspects, the first solid-state radiation source is mounted in the first cavity and the second solid-state radiation source is positioned in the second cavity, the first solid-state radiation source is positioned to emit the first radiation along the flow path in a first direction, the second solid-state radiation source is positioned to emit the second radiation along the flow path in a second direction, and the first direction is different from the second direction.

In some aspects, the one or more lenses may comprise: a converging lens positioned to receive radiation from the solid-state radiation source; and a collimating lens positioned to receive radiation refracted by the converging lens. For example, the collimating lens may be positioned at a distance that is less than its focal length from a focal point of the radiation refracted by the converging lens. For example, a difference between the distance of the collimating lens from the focal point of the radiation refracted by the converging lens and the focal length of the collimating lens may be approximately equal to 10%-35% of the focal length of the collimating lens. As a further example, a differential distance Δ=f−f' between the position f' of the collimating lens relative to the focal point and the focal length f1 of the collimating lens relative to the focal point may be in a range of 10%-35% of the focal length f1.

In other examples, the converging lens may be integrated with the solid-state radiation source. The one or more lenses comprise one or more of a lens with at least a partially convex face lens, a dome lens, a plano-convex lens, and a Fresnel lens. As a further example, the solid-state radiation source comprises a plurality of solid-state radiation sources and the thermally conductive portion is either common to or individualized for the plurality of solid-state radiation sources.

Another aspect of this disclosure is a method comprising: directing a fluid from an inlet through a flow channel of a reactor extending along a flow axis; exposing the fluid to UV radiation emitted from an optical unit into the flow channel, the optical unit positioned in a cavity of the flow channel comprising a solid-state radiation source for emitting UV radiation and at least one thermally conductive portion thermally coupled to the solid-state radiation source; causing the fluid to flow at least partially around the optical unit to an outlet such that the at least one thermally conductive portion of the optical unit is thermally coupled with the fluid; and cooling the optical unit with the fluid.

The method may comprise causing the solid-state radiation source to emit the UV radiation and wherein the solid-state radiation source is a solid-state UV emitter; and/or refracting the emitted UV radiation with at least one lens in the optical unit. For example, refracting the UV radiation may comprise passing the UV radiation through at least one lens in the optical unit configured to match an intensity of the radiation at a location in the flow channel with a velocity of the fluid at the location in the flow channel. Cooling the optical unit may comprise transferring heat from the optical unit through the at least one thermally conductive portion of the optical unit to the fluid in thermal contact with the surface. For example, the reactor may be at least partially comprised of a thermally conductive material and cooling the optical unit may comprise transferring heat from the optical unit through the thermally conductive portion of the optical unit to the reactor through a mounting structure comprised of a thermally conductive material thermally coupled with the thermally conductive portion.

In some aspects, the reactor may be comprised of a thermally non-conductive material and cooling the optical unit comprises only of transferring heat from the optical unit through the at least one thermally conductive portion of the optical unit to the fluid in thermal contact with the surface. Causing the fluid to flow at least partially around the optical unit may comprise causing the fluid to flow around the surface of the optical unit. The method may further comprise: causing the fluid to flow with a velocity that is positively correlated with an intensity of UV radiation emitted from the optical unit. For example, causing the fluid to flow at least partially around the optical unit may comprise causing the fluid to flow at least partially around a removable optical unit and/or causing the fluid to flow at least partially around a unitary optical unit.

As a further example, the method may further comprise: receiving the fluid from a first pipe coaxial with the flow axis attached to the inlet before directing the fluid through the flow channel; and passing the fluid to a second pipe coaxial with the flow axis attached to the outlet after cooling the optical unit with the fluid. For example, the optical unit may be a first optical unit, and the method may further comprise: causing the fluid to flow from the inlet at least partially around a second optical unit, the second optical unit comprising at least one thermally conductive portion, such that the at least one thermally conductive portion of the second optical unit is thermally coupled with the fluid before directing the fluid through the flow channel; exposing the fluid to UV radiation emitted from the second optical unit into the flow channel, the second optical unit comprising a second solid-state radiation source for emitting UV radiation, the second solid-state radiation source being thermally coupled to the at least one thermally conductive portion of the second optical unit; and cooling the second optical unit with the fluid.

Another aspect of this disclosure is an optical unit comprising: a housing comprising a cavity; a PCB attached to a first end of the housing at a first end of the cavity; a solid-state radiation source in the cavity that is attached to the PCB and thermally coupled to a thermally conductive portion of the PCB; a first lens in the cavity that is positioned adjacent to the solid-state radiation source to refract radiation emitted by the solid-state radiation source; a second lens in the cavity that is spaced apart from the first lens and positioned to refract the radiation emitted by the solid-state radiation source and refracted by the first lens; and a UV transparent component attached to a second end of the housing at a second end of the cavity.

In some aspects, the optical unit may be removably mountable in a cavity of a fluid conduit so that fluid flowing in the fluid conduit flows around the unit. For example, fluid flowing in the fluid conduit may flow around the optical unit and be thermally coupled to the at least one heat conductive portion of the exterior surface of the housing of the optical unit. The optical unit is removably mounted to the cavity of the fluid conduit through one or more structures extending from interior surfaces of the cavity engaged with exterior surfaces of the optical unit. For example, the exterior surfaces of the optical unit may be defined by exterior surfaces of a non-thermally conductive portion of the optical unit, and the one or more structures extend to the exterior surfaces of the non-thermally conductive portion, prevent heat transfer between the thermally conductive portion of the optical unit and the body, and permit heat transfer between the thermally conductive portion and fluid. As a further example, the solid-state radiation source may comprise a plurality of solid-state radiation sources and the thermally conductive portion may be either common to or individualized for the plurality of solid-state radiation sources.

In addition to the exemplary aspects described above, further aspects will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIGS. 1A-1D illustrate cross-sectional views of UV reactors according to particular example embodiments.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Embodiments of this disclosure are directed to embodiments of UV-LED reactors that provide enhanced dose uniformity by controlling both the fluidic and optical environments. Some embodiments are described with reference to particular radiation sources, fluids, and radiation types. For example, the radiation source may be a solid-state radiation source such as UV-LED, the fluid may be water, and the radiation may include a UV radiation. Unless claimed, these examples are provided for convenience and not intended to limit the present disclosure. Accordingly, any structural embodiments described in this disclosure may be utilized with any analogous radiation sources, fluids, and/or radiation types.

Numerous axes are described herein, including an exemplary Z-axis. Wherever used, the term "transverse" means: lying, or being across; set crosswise; or made at right angles to the Z-axis and comprises perpendicular and non-perpendicular arrangements. The term "longitudinal" may be used to describe relative components and features. For example, longitudinal may refer to an object having a first dimension or length along the Z-axis that is longer in relation to a second dimension or width along the Z-axis. These terms are provided for convenience and do not limit this disclosure unless claimed.

As used herein, the terms "comprises," "comprising," or any other variation thereof, are intended to cover a non-exclusive inclusion, such that an apparatus, method, or element thereof comprising a list of elements does not include only those elements, but may include other elements not expressly listed or inherent the apparatus or method. Unless stated otherwise, the term "exemplary" is used in the sense of "example," rather than "ideal." Various terms of approximation may be used in this disclosure, including "approximately" and "generally." Approximately means within plus or minus 10% of a stated number.

Figure 1A:
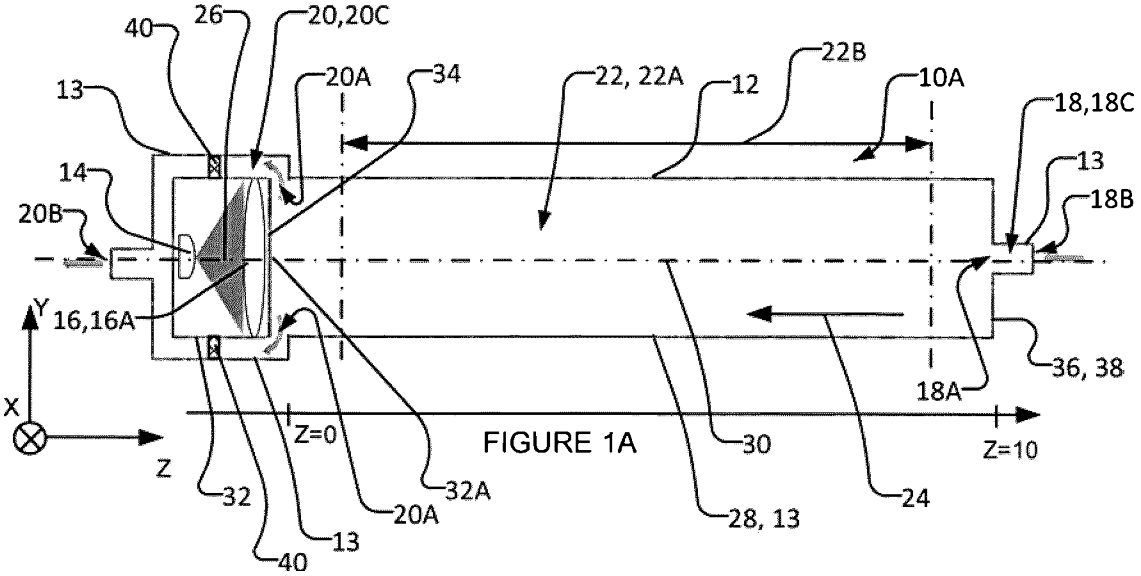

FIG. 1A is a cross-sectional view of an exemplary UV reactor 10A according to a particular embodiment. Reactor 10A may comprise a fluid conduit 12 defined at least in part by an outer conduit-defining wall 13 for permitting a fluid flow therethrough, a solid-state UV emitter 14 (e.g. a UV-LED), and a radiation focusing element 16 comprising one or more lenses 16A. With the exception of the optical components (e.g. UV emitter 14 and lenses 16A), reactor 10A may be fabricated from stainless steel, suitable polymers, plastic, glass, quartz, combinations of these materials and/or other suitable material(s). As shown, fluid conduit 12 may comprise a fluid inlet 18, a fluid outlet 20, and a longitudinally extending fluid flow channel 22 located between inlet 18 and outlet 20.

In the illustrated embodiment, the longitudinal direction is shown as being aligned with the Z-axis; and a fluid may generally flow through fluid flow channel 22 in a longitudinal direction shown by arrow 24. For example, the fluid may flow in longitudinal direction 24 through a bore 22A of fluid flow channel 22; and fluid flow channel 22 may have a central channel axis 30 that extends in longitudinal direction 24 through centroids of transverse cross-sections of bore 22A in at least a longitudinally central portion 22B of bore 22A. Fluid inlet 18 may comprise one or more inlet apertures 18A, where fluid inlet 18 opens into fluid flow channel 22, one or more connecting apertures 18B, through which UV reactor 10A may be connected to an external fluid system (not shown) which provides fluid to reactor 10A and one or more inlet conduits 18C which may extend between inlet aperture(s) 18A and connecting aperture(s) 18B. Similarly, fluid outlet 20 may comprise one or more inlet apertures 20A, where fluid outlet 20 opens into fluid flow channel 22, one or more connecting apertures 20B, through which UV reactor 10A may be connected to an external output fluid system (not shown) to which fluid flows from reactor 10A and one or more outlet conduits 20C which may extend between outlet aperture(s) 20A and connecting aperture(s) 20B.

Lens(es) 16A may be positioned in a radiation path of radiation 26 emitted from UV emitter 14 for directing radiation 26 from UV emitter 14 to impinge on the fluid flowing in fluid flow channel 22 and to thereby provide a radiation fluence rate profile (not shown in FIG. 1A) within a bore 22A of fluid flow channel 22 defined by bore-defining surface 28.

Lens(es) 16A may be configured to provide a radiation fluence rate profile wherein, for cross-sections of bore 22A of fluid flow channel 22 located relatively close to UV emitter 14 (e.g. relatively close to Z=0 in the illustrated view), the radiation fluence rate profile is relatively high at locations relatively far from a central channel axis 30 of bore 22A of fluid flow channel 22 and relatively low for locations nearer to central channel axis 30. Central channel axis 30 may comprise a central axis (e.g. an axis of cylindrical symmetry) of bore 22A of fluid flow channel 22 or at least a longitudinally central portion 22B of bore 22A of fluid flow channel 22. Lens(es) 16A may be further configured to provide a radiation fluence rate profile wherein, for cross-sections of the bore 22A of the fluid flow channel 22 located relatively distal from UV emitter 14 (e.g. relatively close to Z=10 in the illustrated view), the radiation fluence rate profile is relatively low at locations relatively far from central channel axis 30 and relatively high at locations nearer to central channel axis 30.

Figure 2A:
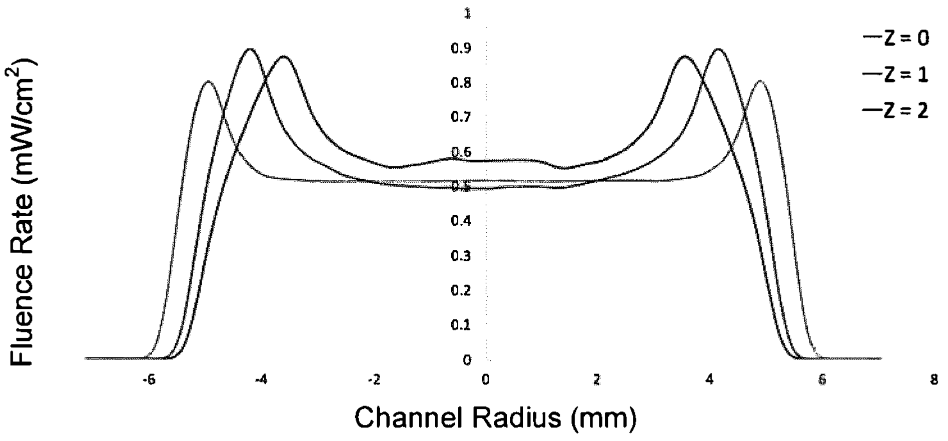
FIGS. 2A, 2B and 2C show radiation fluence rate profiles for cross-sections of the bore of the fluid flow channel of the FIG. 1A reactor.
Figure 2B:
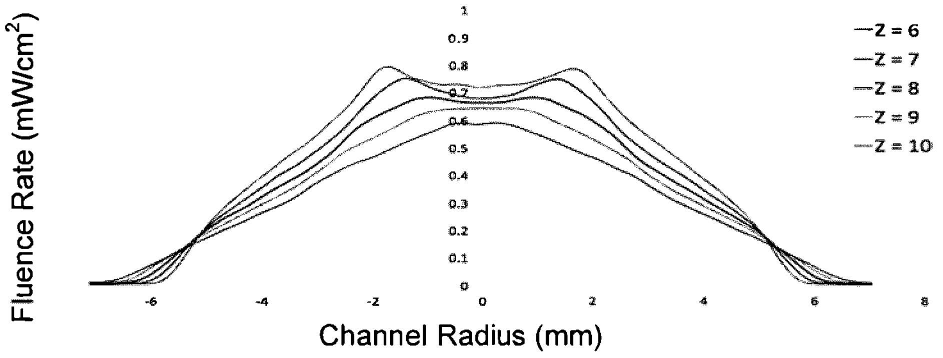
Figure 2C:
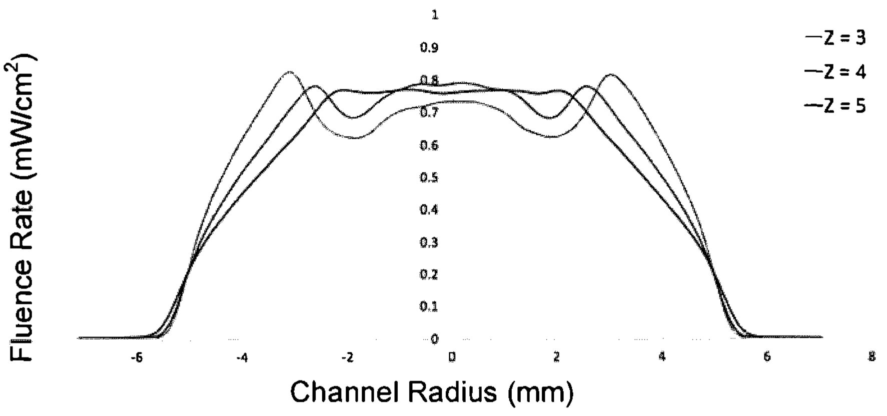
Figure 2D:
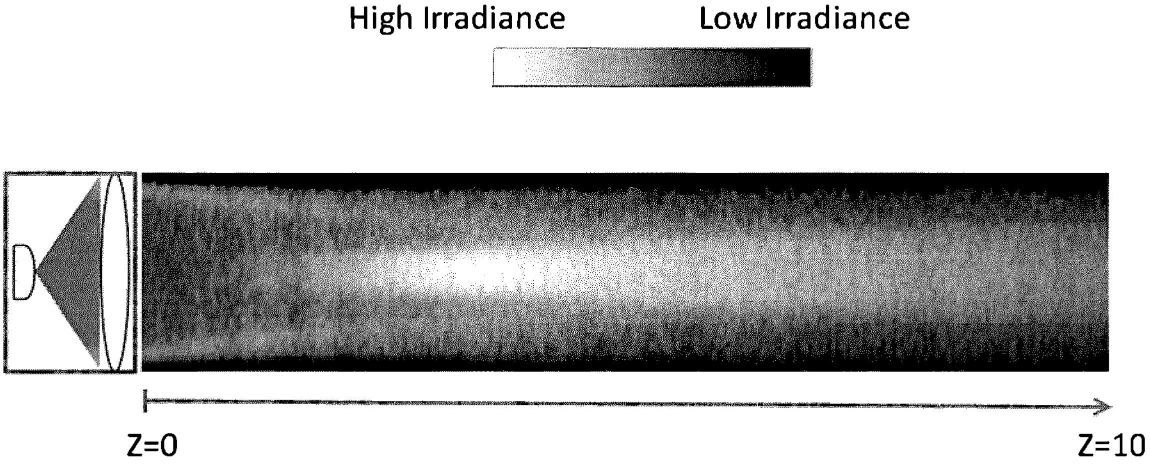
FIG. 2D shows a radiation fluence plot for the entire longitudinal direction of the FIG. 1A reactor.

Exemplary properties of the radiation fluence rate profile are shown in FIGS. 2A-2D. FIGS. 2A-2C show radiation fluence rate profiles for various cross-sections of the bore 22A of fluid flow channel 22 of the FIG. 1A reactor 10A at various locations (e.g. at various Z-values) along central channel axis 30. FIG. 2D shows a rendering of the fluence rate profile over the entire longitudinal direction of fluid flow channel 22 of the FIG. 1A reactor 10A with lighter regions representing higher fluence rate and darker regions representing lower fluence rate. The Y-axes of the plots of FIGS. 2A-2C represent radiation fluence rate (in $mW/cm^2$). The X-axes of the plots of FIGS. 2A-2C represent radial distances from central channel axis 30 (e.g. along the X-axis shown in FIG. 1A or along any other suitable radial direction in the case where bore 22A is circular in cross-section). The origins of the X-axis of the plots of FIGS. 2A-2C represent locations on central channel axis 30; and larger values of X on the plots of FIGS. 2A-2C represent locations that are relatively far from central channel axis 30.

FIG. 2A shows fluence rate profiles for cross sections (Z=0, Z=1, Z=2) which are relatively close to UV emitter 14. It can be seen from FIG. 2A that for each of these cross-sections, the fluence rates are relatively high at locations relatively far from central channel axis 30 and relatively low at central channel axis 30. For example, FIG. 2B shows fluence rate profiles for cross sections (Z=6, 7, 8, 9, 10) which are relatively distal from UV emitter 14. It can be seen from FIG. 2B that for each of these cross-sections, the fluence rates are relatively low at locations that are relatively far (e.g. $|x|>2$) from central channel axis 30, and relatively high at locations closer (e.g. $|x|<2$) to central channel axis 30. For the FIG. 2B plots corresponding to Z=9 and Z=10, the fluence rates are relatively low at all locations that are relatively far from central channel axis 30, and relatively high at central channel axis 30. FIG. 2C shows fluence rate profiles for centrally located cross-sections (Z=3, Z=4, Z=5) and shows that the cross-sections of bore 22A are provided with relatively high fluence rates even in these central cross-sections. FIG. 2D shows a rendering of the fluence rate profile over the entire longitudinal direction of fluid flow channel 22 of the FIG. 1A reactor 10A with lighter regions representing higher fluence rate (higher irradiance) and darker regions representing lower fluence rate (lower irradiance).

Lens(es) 16A may be configured to provide fluence rate profiles having the above-discussed characteristics by one or more of: a selection of the one or more lenses from among a variety of lens types; a shape of the one or more lenses, such as a thickness of the lenses and/or curvature of the optical surfaces of the lenses; a position of the one or more lenses; and an indices of refraction of the one or more lenses to provide the radiation fluence rate profile having these characteristics. Radiation-focusing element 16 may comprise a focusing lens 16A or a combination of two or more focusing lenses 16A disposed proximate to UV emitter 14. Focusing lens(es) 16A may comprise any combination of a converging lens, a diverging lens, and any other type of lens. In some embodiments, focusing lens(es) 16A may comprise a converging lens optically adjacent to UV emitter 14 and a collimating lens at some suitable distance away from the converging lens. In some embodiments, lens(es) 16A may comprise a converging lens located to receive radiation 26 from UV emitter 14 and a collimating lens, where the collimating lens may be positioned at a distance less than its focal length (e.g. by a differential distance Δ) from the focal point of radiation emitted from the converging lens.

Figure 12A:
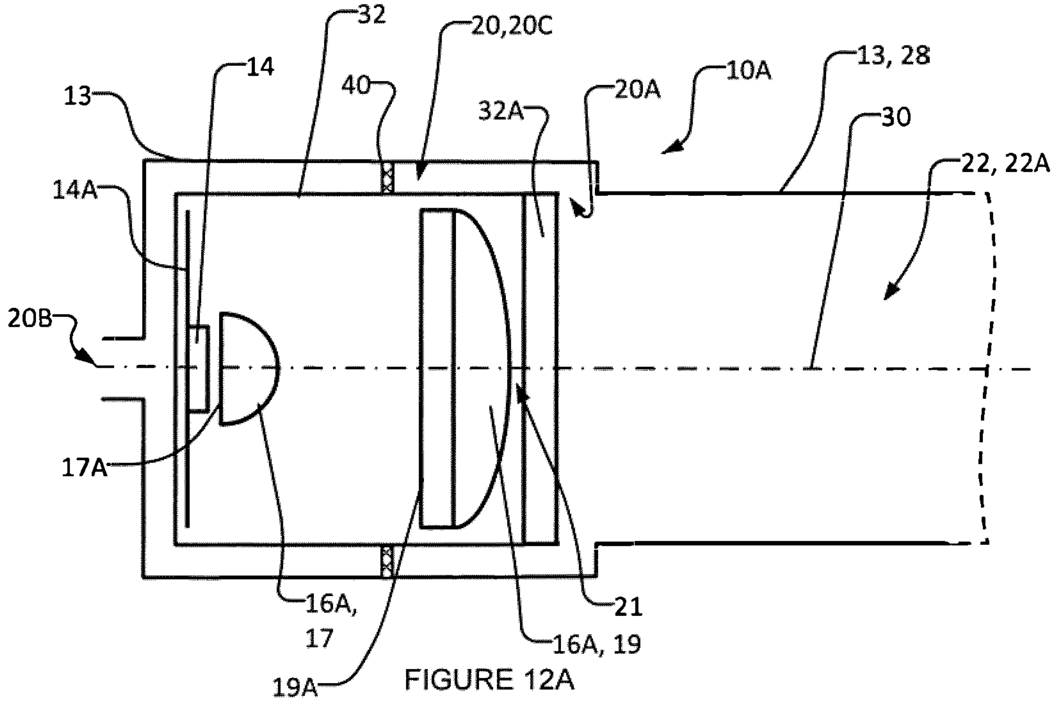
FIG. 12A is a schematic illustration of one end of the FIG. 1A reactor according to a particular embodiment showing its housing, solid state UV emitter and lens(es).

In some embodiments, lens(es) 16A may comprise a half-ball lens and a plano-convex lens. FIG. 12A is a schematic illustration of one end of reactor 10A according to a particular embodiment showing housing 32, solid state UV emitter 14 and lens(es) 16A in more detail. As shown in the FIG. 12A, for example, solid state UV emitter 14 may be mounted on a circuit board 14A along with suitable electronics (not shown) for providing power to UV emitter 14. In this example, lenses 16A may comprise: a half-ball lens 17 that is shaped and/or located to receive radiation from UV emitter 14; and a plano-convex lens 19 that is shaped and/or located to receive radiation from half-ball lens 17. Both of lenses 17, 19 may have their respective planar sides 17A, 19A facing UV emitter 14; and both of lenses 17, 19 may have their optical axes co-axial with central channel axis 30 as shown in FIG. 12A.

In some embodiments, there is an air space 21 between plano-convex lens 19 and the fluid in bore 22A of fluid flow channel 22 (e.g. within housing 32). In some embodiments, there is an air space 21 and a UV-transparent (e.g. quartz) window 32A between plano-convex lens 19 and the fluid in bore 22A of fluid flow channel 22. In some embodiments, plano-convex lens 19 may be positioned at a distance f', which is less than its focal length f1, from the focal point 23 of radiation emitted from half-ball lens 17. This is illustrated schematically in Figured 12B for a particular embodiment, in which the radiation emitted from half-ball lens 17 has a focal point 23 and plano-convex lens 19 has an inherent focal length f1, but plano-convex lens 19 is not located at a distance f1 from focal point 23. Instead, in the illustrated embodiment, plano-convex lens 19 is located at a distance f' from focal point 23, where f' is less than f1 by a differential distance Δ. In some embodiments, this differential distance Δ is in a range of 10%-35% of the focal length f1 of plano-convex lens 19. In some embodiments, this differential distance Δ is in a range of 15%-30% of the focal length f1 of plano-convex lens 19. In some embodiments, this this differential distance Δ is in a range of 20%-30% of the focal length f1 of plano-convex lens 19.

Figure 12B:
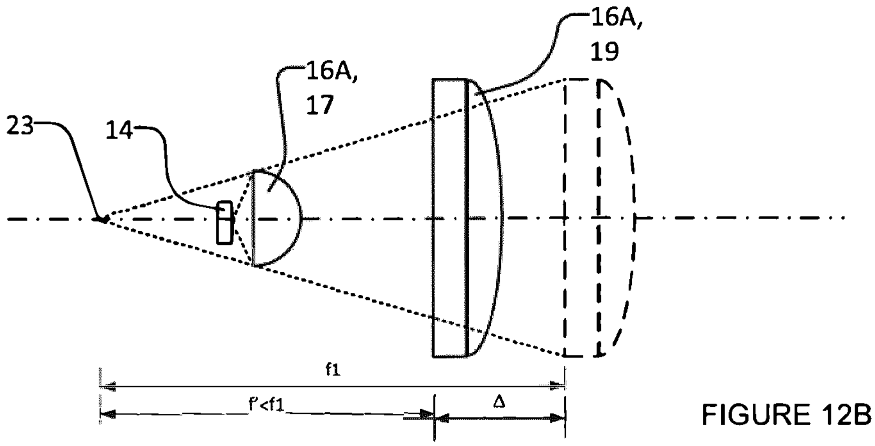
FIG. 12B is a schematic illustration depicting characteristics of the lens positioning according to a particular embodiment.
Figure 3A:
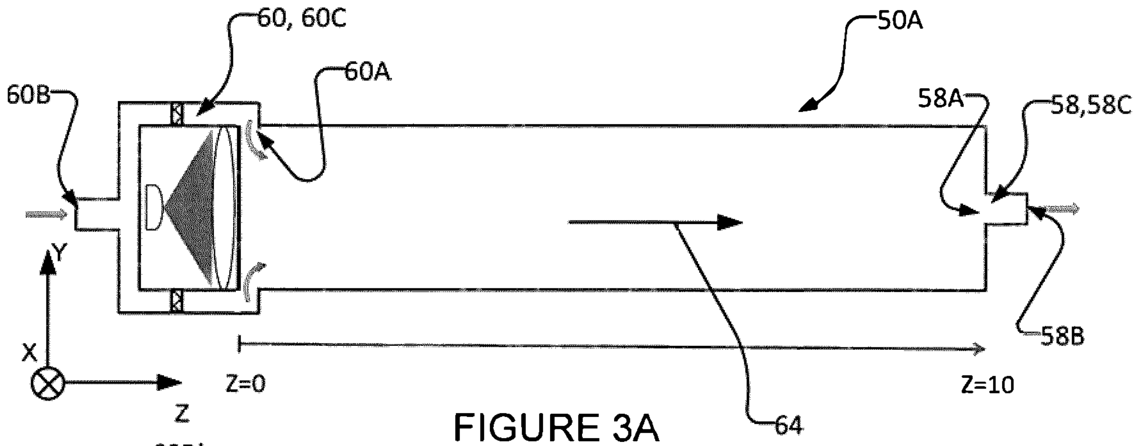
FIGS. 3A-3D illustrate cross-sectional views of UV reactors according to particular example embodiments.
Figure 3B:
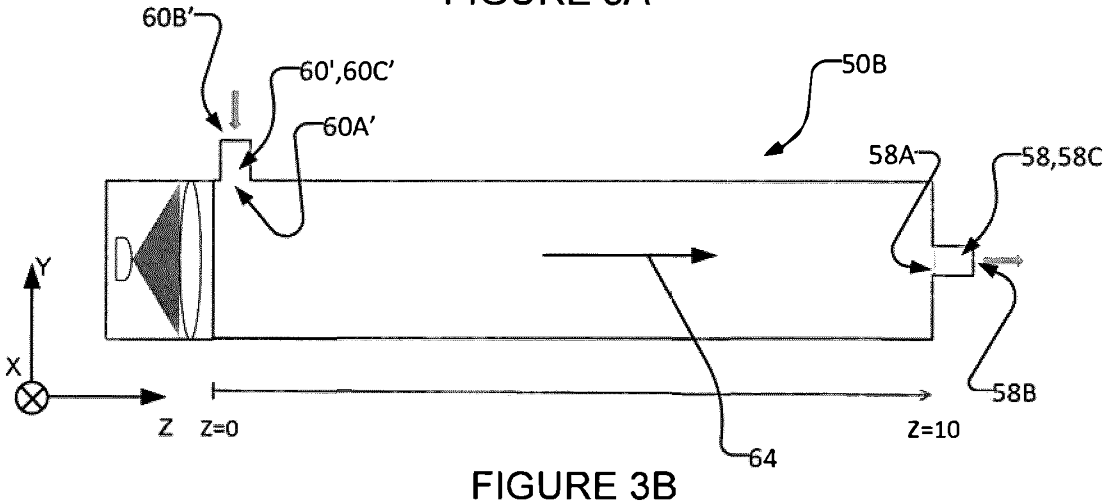
Figure 3C:
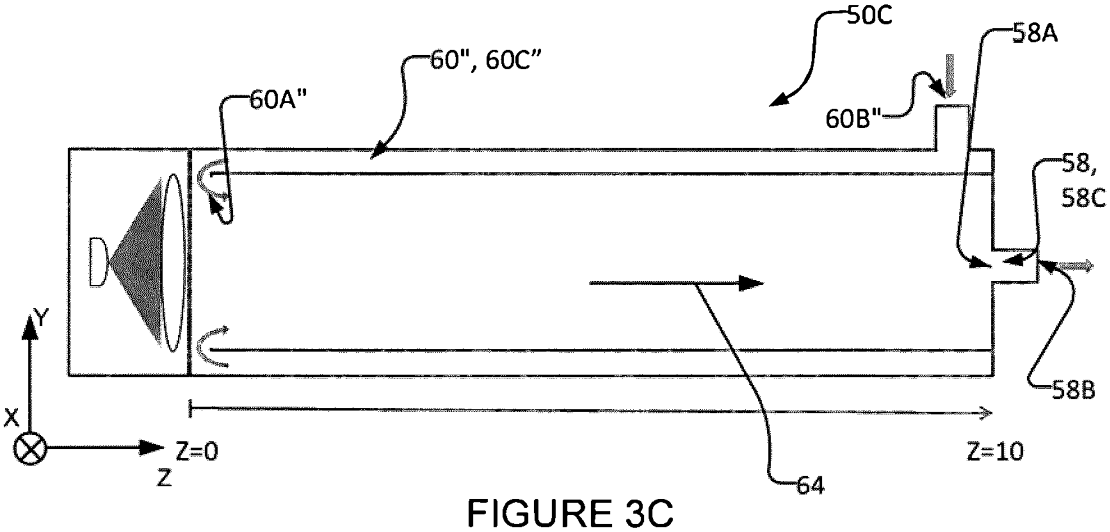
Figure 3D:
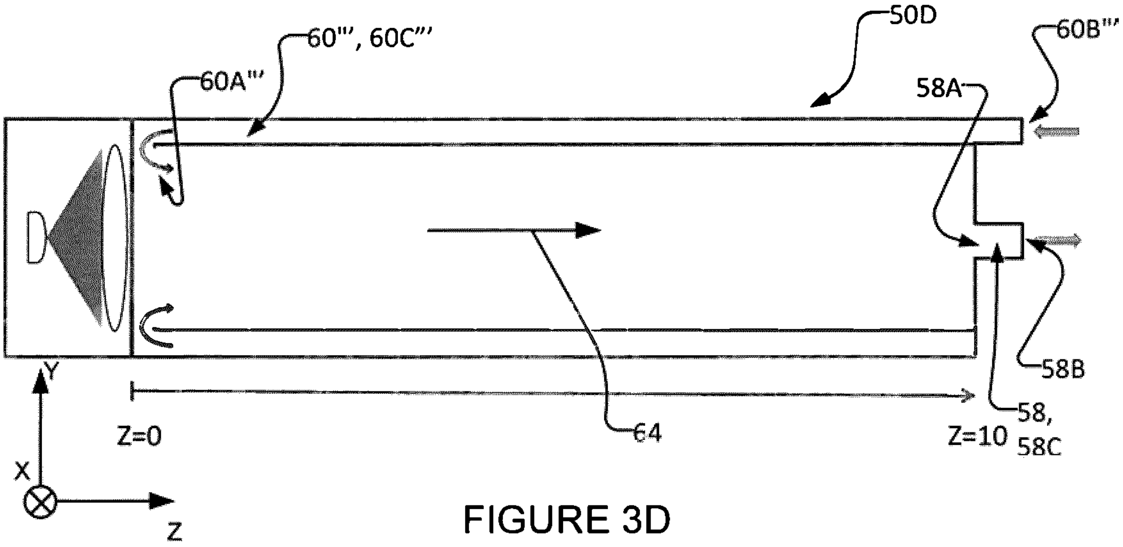

The features of housing 32, solid state UV emitter 14, and lenses 17, 19 of the embodiments of FIGS. 12A and 12B may be used for any of the housings, emitters and/or lenses of any of the reactors described herein. In general, lenses 16A are not limited to the particular lenses shown in FIGS. 12A and 12B. For example, lens(es) 16A may comprise any suitable combination of biconvex, biconcave, plano-convex, plano-concave, meniscus, or half-ball lens(es). Lenses 16A may comprise a first lens (located closer to UV emitter 14) and a second lens (located relatively far from UV emitter 14). For example, radiation emitted from the first lens may have a focal point 23 and the second lens may have an inherent focal length ft but the second lens may not be located at a distance f1 from the focal point of the first lens. Instead, the second lens may be located at a distance f' from the focal point of the first lens, where f' is less than f1 by a differential distance Δ. In some embodiments, this differential distance Δ is in a range of 10%-35% of the focal length f1 of the second lens. In some embodiments, this differential distance Δ is in a range of 15%-30% of the focal length f1 of the second lens. In some embodiments, this this differential distance Δ is in a range of 20%-30% of the focal length f1 of the second lens.

Bore-defining wall 28 may be shaped to define bore 22A to have a cylindrical shape over at least a longitudinally central portion 22B of fluid flow channel 22. Longitudinally central portion 22B may be spaced apart from fluid inlet 18 and fluid outlet 20. The cylindrical shape may comprise a cylinder with circular cross-section or a cylinder with some other (e.g. rectangular or other polygonal) cross-section. In some embodiments, the principal optical axis of UV emitter 14, the optical axes of lens(es) 16A and central channel axis 30 may be co-linear or co-axial.

In some embodiments, UV emitter 14 may be housed in a housing 32 that may comprise a UV transparent component 32A (e.g. a quartz window) to transmit radiation from housing 32 into fluid flow channel 22. For example, lens(es) 16A also may be housed in housing 32, although this is not necessary.

In some embodiments, UV emitter 14 may be located relatively proximate to fluid outlet 20 (e.g. at the outlet end 34 of bore 22A); and relatively distal from fluid inlet 18, with the principal optical axis of UV emitter 14 being oriented generally antiparallel to longitudinal fluid flow direction 24. Fluid conduit 12 may comprise a cross-sectional wall 36 at one end (e.g., an inlet end) 38 of bore 22A. Cross-sectional wall 36 may define inlet aperture 18A of fluid inlet 18 or may otherwise support fluid inlet 18. In some embodiments, cross-sectional wall 36 may be reflective, although this is not necessary. Inlet aperture 18A and/or fluid inlet 18 may be centrally located in cross-sectional wall 36. Central channel axis 30 may project through inlet aperture 18A and/or fluid inlet 18. A cross-section of inlet aperture 18A and/or fluid inlet 18 may be circularly symmetric about a point that is located on central channel axis 30. With inlet aperture 18A and/or fluid inlet 18 exhibiting these properties, for cross-sections of bore 22A of fluid flow channel 22 located relatively close to inlet aperture 18A (and in the case of the illustrated embodiment, relatively distal from emitter 14), the fluid velocity will be relatively low at locations that are relatively far from central channel axis 30 and relatively high at locations relatively close to central channel axis 30.

In some embodiments, UV emitter 14 may be supported by one or more brackets 40 which support UV emitter 14 (and/or housing 32) such that: the principal optical axis of UV emitter 14 may be at least generally aligned with central channel axis 30; and the fluid may still flow through fluid outlet 20. Brackets 40 may extend from outer conduit-defining wall 13 of fluid conduit 12 to housing 32. In some embodiments, brackets 40 may be fabricated from perforated materials that permit fluid flow therethrough; comprise one or more annular rings of perforated material; and/or additionally or alternatively be transversely (e.g. circumferentially) spaced apart from one another.

In some embodiments, an outlet aperture 20A of fluid outlet 20 may be defined by a combination of outer conduit-defining wall 13 (e.g., bore-defining wall 28) and housing 32. Brackets 40 also may define a portion of outlet aperture(s) 20A. Fluid outlet 20 may be supported by any combination of: outer conduit-defining wall 13 (possibly including bore-defining wall 28); housing 32; and/or brackets 40. Outlet conduit 20C of fluid outlet 20 may have generally annular cross-sections at locations between outlet aperture(s) 20A and connecting aperture(s) 20C. These annular cross-sections may be defined by outer conduit-defining wall 13 and housing 32, except in regions where this annular shape is interrupted by brackets 40.

With this exemplary configuration, outlet aperture(s) 20A and/or fluid outlet 20 may be located at locations that are spaced transversely apart from central channel axis 30 (i.e. toward the cross-sectional edge(s) of fluid conduit 12). In some embodiments, these locations of outlet aperture(s) 20A and/or fluid outlet 20 may be as transversely far away from central channel axis 30 as may be permitted by bore 22A of fluid flow channel 22 or by fluid conduit 12 generally. Consequently, with outlet aperture(s) 20A and/or fluid outlet 20 exhibiting these properties, for cross-sections of the bore 22A of fluid flow channel 22 located relatively close to UV emitter 14 or close to outlet aperture(s) 20A, the fluid velocity may be: relatively high at some locations relatively far from central channel axis 30 (e.g. at locations directly upstream from or adjacent to outlet aperture(s) 20A); and relatively low at some locations relatively close to central channel axis 30.

Figure 4A:
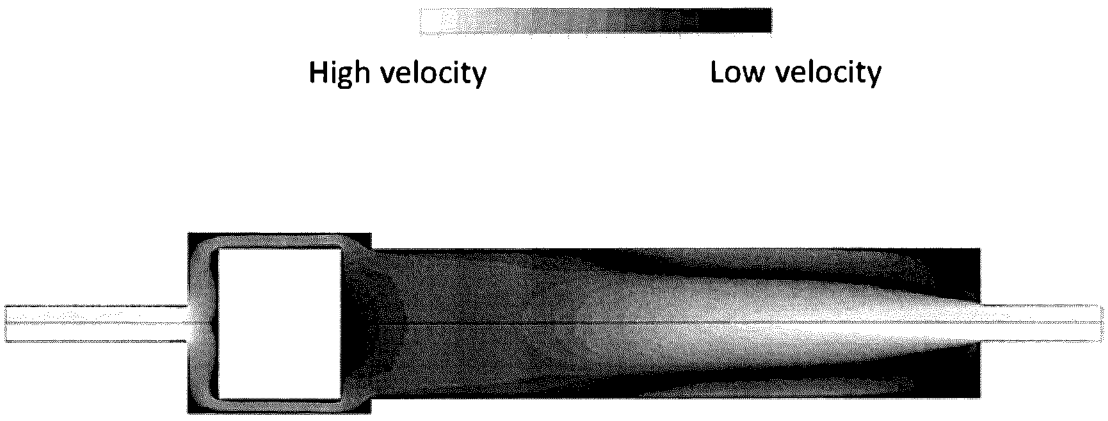
FIGS. 4A-4C show various simulation plots of the fluid velocity distribution for the reactor of FIG. 1A.
Figure 4B:
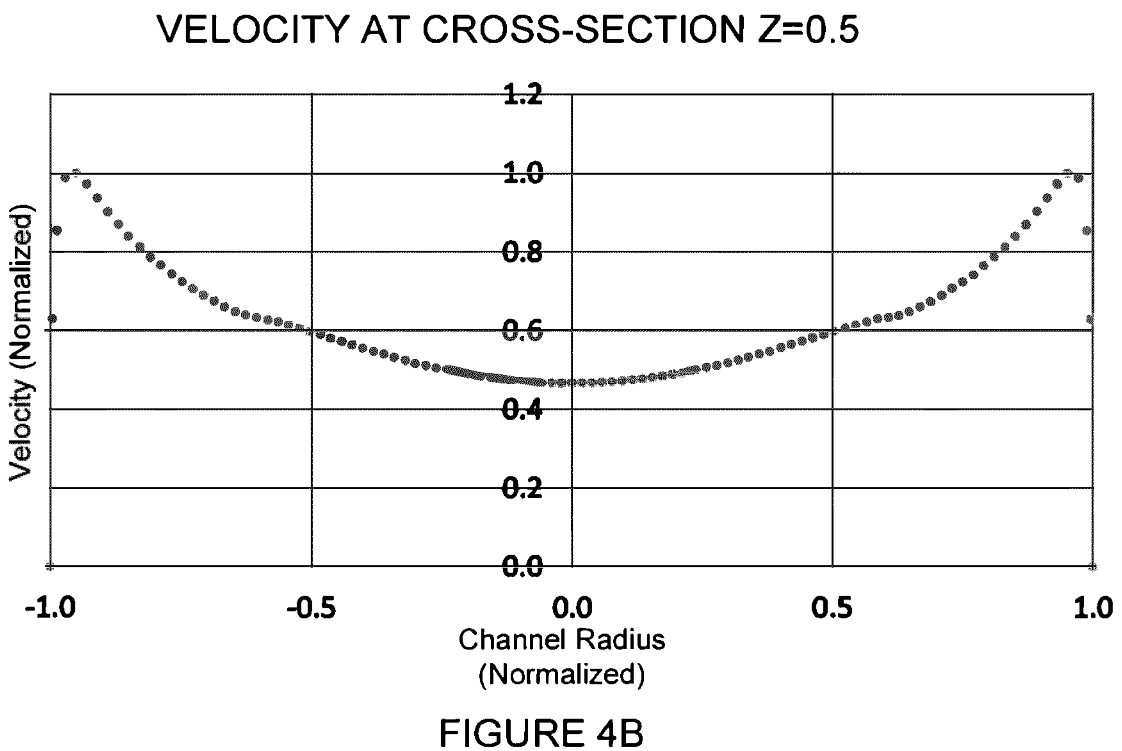
Figure 4C:
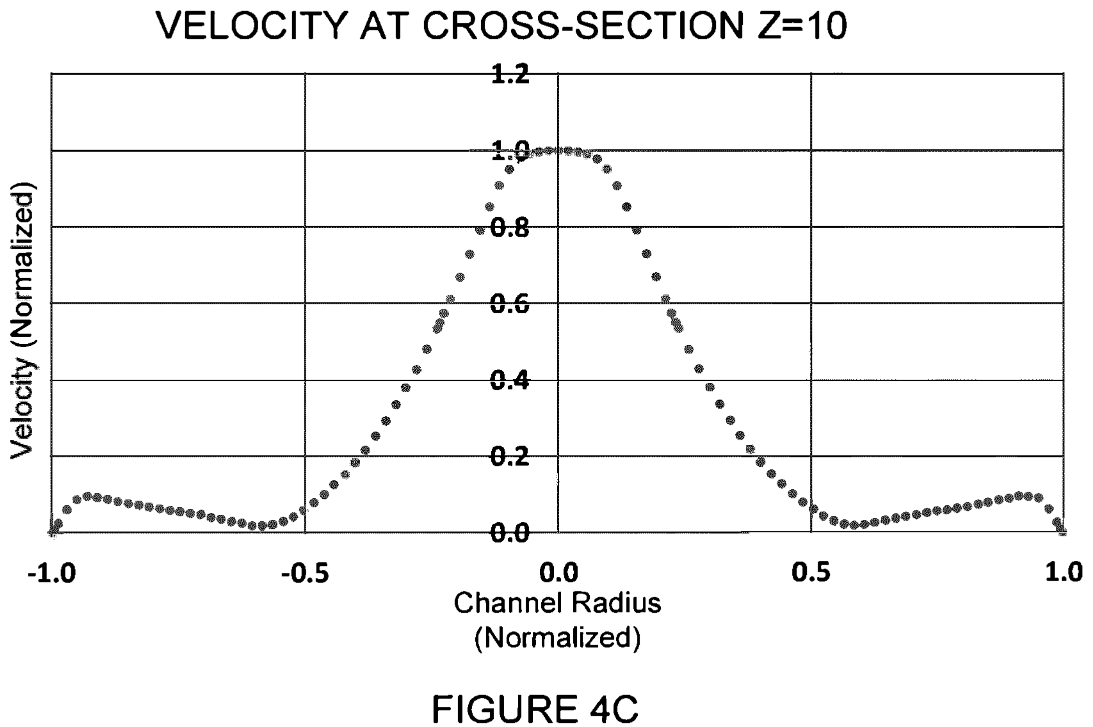

Exemplary properties of the fluid velocity profile of reactor 10A of the FIG. 1A embodiment are shown in FIGS. 4A-4C. FIG. 4A is a fluid velocity mapping showing fluid velocities for different regions of reactor 10A with relatively high local fluid velocities having lighter colors and relatively low local fluid velocities having darker colors. FIG. 4B shows a plot of fluid velocity versus distance from central channel axis 30 at the cross-section corresponding to Z=0.5 (i.e. relatively close to UV emitter 14) and FIG. 4C shows a plot of fluid velocity versus distance from central channel axis 30 at the cross-section corresponding to Z=10 (i.e. relatively distal from UV emitter 14). In the plots of FIGS. 4B and 4C, central channel axis 30 corresponds to the origins of the X-axes. FIGS. 4A-4C show that for reactor 10A of the FIG. 1A embodiment, for cross-sections closer to UV emitter 14 (low Z values in the illustrated embodiment (e.g. FIG. 4B)), the fluid velocity may be higher at some locations relatively far from central channel axis 30 and lower at some locations nearer to central channel axis 30; and that, for cross-sections distal from UV emitter 14 (high Z values in the illustrated embodiment (e.g. FIG. 4C)), the fluid velocity may be lower at locations spaced transversely apart from central channel axis 30 and higher at locations nearer to central channel axis 30.

For reactor 10A, fluid inlet 18 may be located transversely near to central channel axis 30, and fluid outlet 20 may be located toward the transverse cross-sectional edge(s) of fluid conduit 12. Accordingly, the combined effect for UV reactor 10A may be that: (1) for cross-sections of bore 22A of fluid flow channel 22 located relatively close to fluid inlet 18, the fluid velocity may be relatively low at locations that are relatively far from central channel axis 30 and relatively high at locations relatively close to central channel axis 30; and (2) for cross-sections of the bore 22A of fluid flow channel 22 located relatively close to fluid outlet 20, the fluid velocity may be relatively high at some locations relatively far from central channel axis 30 (e.g. at locations directly upstream from or adjacent to outlet aperture(s) 20A) and relatively low at some locations relatively close to central channel axis 30.

As discussed above, UV emitter 14 and lens(es) 16A of reactor 10A may be located at the outlet end 34 of fluid conduit 12 and configured to direct radiation in a general direction that is antiparallel to and/or opposite of the fluid flow direction through fluid conduit 12. Further, lens(es) 16A of UV reactor 10A may be configured such that: (1) for cross-sections of the bore 22A of the fluid flow channel 22 located relatively distal from UV emitter 14 or relatively close to fluid inlet 18, the radiation fluence rate profile may be relatively low at locations relatively far from central channel axis 30 and relatively high at locations nearer to central channel axis 30; and (2) for cross-sections of the bore 22A of fluid flow channel 22 located relatively close to UV emitter 14 or close to fluid outlet 20, the radiation fluence rate profile may be relatively high at locations relatively far from central channel axis 30 and relatively low at locations nearer to central channel axis 30. Thus, the radiation fluence rate in reactor 10A may be relatively high in regions where the fluid velocity is relatively high; and relatively low in regions where the fluid velocity is relatively low. Accordingly, the UV fluence (UV dose), which is a function of UV fluence rate and residence time (inverse of velocity), imparted on the fluid as it traverses bore 22A of fluid flow channel 22 of reactor 10A may be relatively uniform.

In some embodiments, fluid outlet conduit 20C may be shaped so that it is defined in part by housing 32 or otherwise in direct or indirect thermal contact with housing 32, which in turn may be in direct or indirect (e.g. via a printed circuit board (PCB) 14A (FIG. 12A)) thermal contact with UV emitter 14 (i.e. on transverse side(s) of housing 32 or portions thereof and/or on a side of UV emitter 14 opposing the principal optical axis of the solid-state UV emitter or a portion thereof) for removing heat from UV emitter 14 and transferring such heat to the fluid that is removed from reactor 10A. In some embodiments, a printed circuit board (PCB) 14A (FIG. 12A) on which UV emitter 14 may be mounted to provide a wall of housing 32 and/or outlet conduit 20C or a portion thereof so that the fluid may be in direct thermal contact with PCB 14A on which UV emitter 14 is mounted. This heat removal may be particularly effective because of the high degree of mixing as a result of flow contraction and sudden change in the fluid velocity when the fluid flow is directed from bore 22A of fluid flow channel 22 into the relatively narrow fluid outlet 20. This heat transfer (from the surrounding wall of housing 32) may be particularly effective as a result of heat being removed from many surfaces of housing 32 and the corresponding surface area. Also, by controlling the cross-section of the outlet conduit 20C, higher fluid velocities may be achieved near the walls of housing 32 to further enhance heat transfer.

Figure 1B:
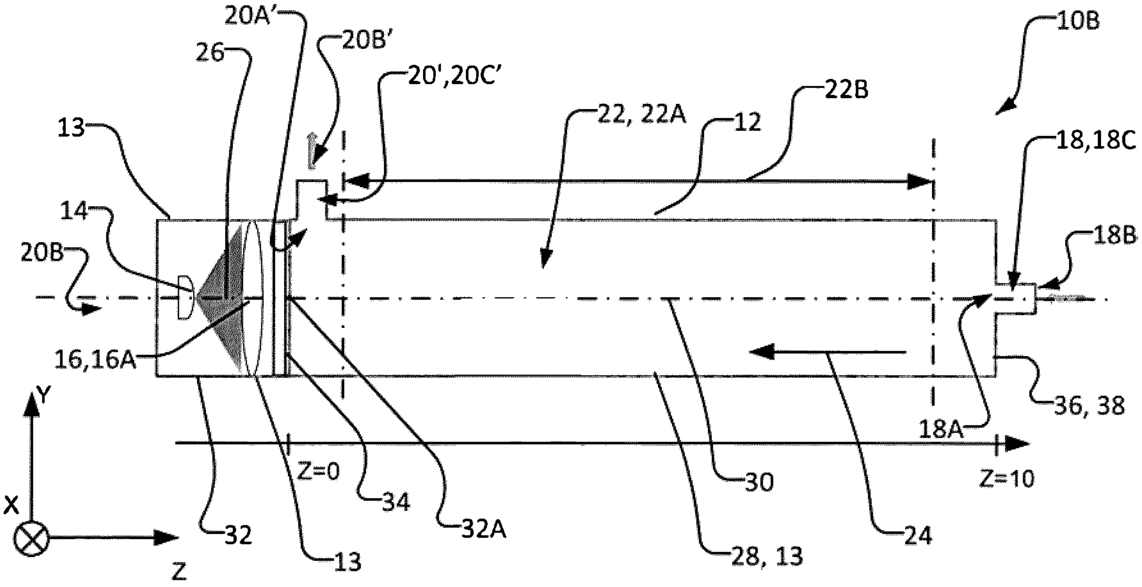

FIG. 1B illustrates a cross-sectional view of a UV reactor 10B according to another particular example embodiment. Reactor 10B is similar to reactor 10A in many respects and similar features of reactor 10B are referred to with similar reference numerals to those of reactor 10A. Reactor 10B differs from reactor 10A primarily in that reactor 10B has a fluid outlet 20' that is located and shaped differently from outlet 20 of reactor 10A. As can be seen from FIG. 1B, reactor 10B may include a fluid outlet 20' that extends generally transversely (i.e. orthogonal to the longitudinal fluid flow direction 24) from fluid flow channel 22. Fluid outlet 20' may comprise an outlet aperture 20A' that is located at an outlet end 34 of reactor 10B; and is defined either by bore-defining wall 28 of fluid flow conduit 22, or by a combination of bore-defining wall 28 and housing 32. While not shown in the illustrated embodiment, reactor 10B may comprise a plurality of fluid outlets 20', extending from fluid flow channel 22 in different and spaced apart in transverse (e.g. circumferential) directions. Each of these fluid outlets 20' may be similar to fluid outlet 20' shown and described herein. As is the case, with fluid outlet 20 of reactor 10A, fluid outlet 20' and/or outlet aperture 20A' may be spaced transversely apart from central channel axis 30 (i.e. toward the cross-sectional edge(s) of fluid conduit 12). In some embodiments, these locations of outlet aperture(s) 20A' and/or fluid outlet 20' may be as transversely far away from central channel axis 30 as may be permitted by bore 22A of fluid flow channel 22 or by fluid conduit 12 generally.

Figure 5A:
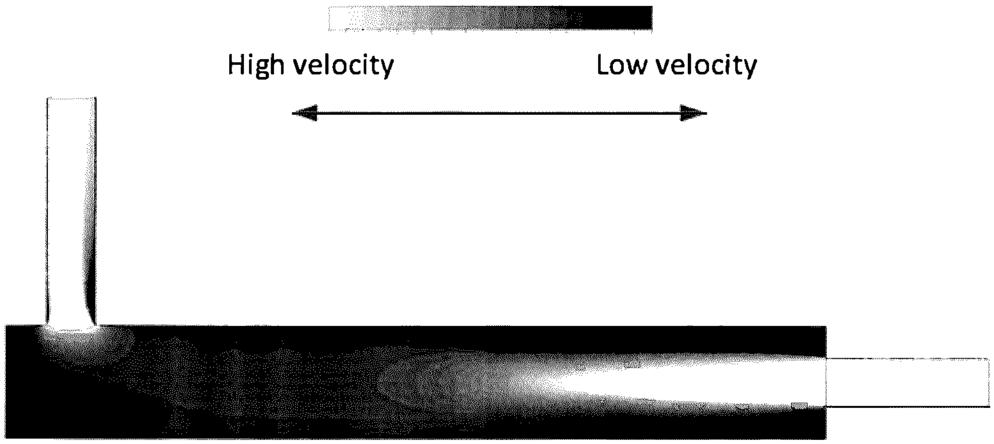
FIGS. 5A-5C show various simulation plots of the fluid velocity distribution for the reactor of FIG. 1B.
Figure 5B:
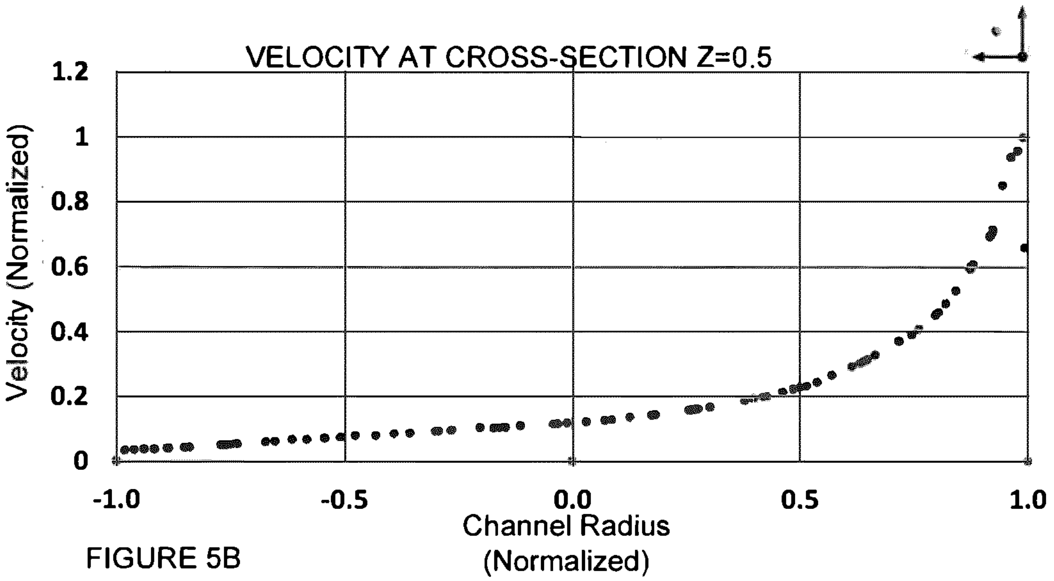
Figure 5C:
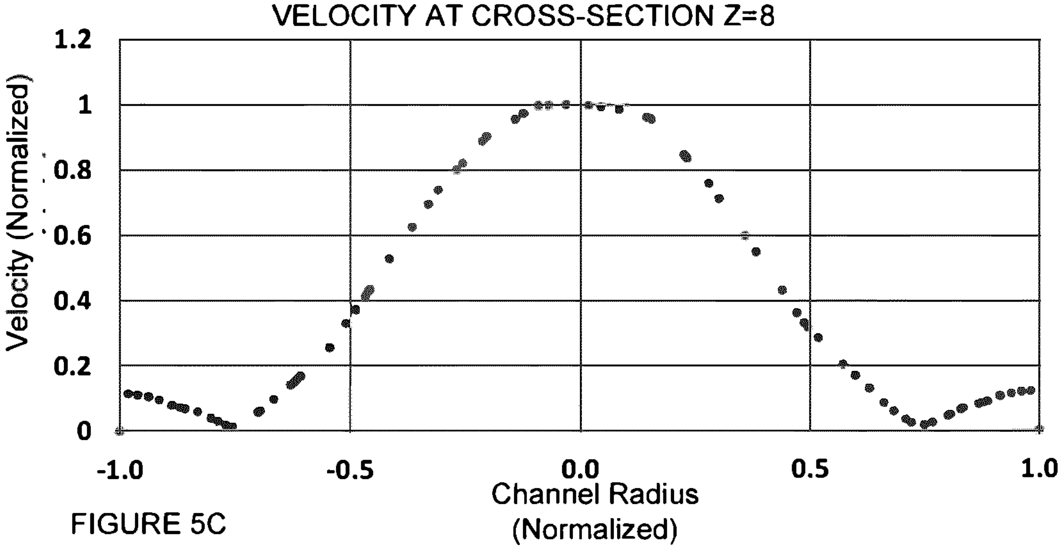

With outlet aperture(s) 20A' and/or fluid outlet 20' exhibiting these properties, reactor 10B may exhibit the same properties of reactor 10A that, for cross-sections of the bore 22A of fluid flow channel 22 located relatively close to UV emitter 14 or close to outlet aperture(s) 20A', the fluid velocity may be relatively high at some locations relatively far from central channel axis 30 (e.g. at locations directly upstream from or adjacent to outlet apertures 20A') and relatively low at some locations relatively close to central channel axis 30. In other respects, reactor 10B may have features similar to those of reactor 10A described herein. FIGS. 5A-5C show simulation plots analogous to those of FIGS. 4A-4C for reactor 10B, except that FIG. 5C is taken at z=8 (as opposed to Z=10 for FIG. 4C). FIGS. 5A-5C show that, for cross-sections closer to UV emitter 14 (low Z values in the illustrated embodiment (e.g. FIG. 5B)), the fluid velocity may be higher at some locations relatively far from central channel axis 30 (e.g. at locations directly upstream from or adjacent to outlet apertures 20A'), and lower at some locations nearer to central channel axis 30; and that, for cross-sections distal from UV emitter 14 (high Z values in the illustrated embodiment (e.g. FIG. 5C)), the fluid velocity may be lower at locations spaced transversely apart from central channel axis 30 and higher at locations nearer to central channel axis 30.

FIG. 1C illustrates a cross-sectional view of a UV reactor 10C according to another particular example embodiment. Reactor 10C is similar to reactor 10A in many respects and similar features of reactor 10C are referred to with similar reference numerals to those of reactor 10A. Reactor 10C differs from reactor 10A primarily in that reactor 10C has a fluid outlet 20" that is located and shaped differently from outlet 20 of reactor 10A. As can be seen from FIG. 1C, reactor 10C may include a fluid outlet 20" that causes fluid to exit transversely from bore 22A of fluid flow channel 22 and then may have an outlet conduit 20C" that extends back in the longitudinal direction in a direction generally antiparallel to the longitudinal fluid flow direction 24 for some distance before extending transversely to its connecting aperture 20B'. Fluid outlet 20" may comprise an outlet aperture 20A" that is located at an outlet end 34 of reactor 10B and may be defined either by bore-defining wall 28 of fluid flow conduit 22 or by a combination of bore-defining wall 28 and housing 32. While not shown in the illustrated embodiment, reactor 10C may comprise a plurality of fluid outlets 20", extending from fluid flow channel 22 in different and spaced apart in transverse (e.g. circumferential) directions. Each of these fluid outlets 20" may be similar to fluid outlet 20" shown and described herein. As is the case, with fluid outlet 20 of reactor 10A, fluid outlet 20" and/or outlet aperture 20A" may be spaced transversely apart from central channel axis 30 (i.e. toward the cross-sectional edge(s) of fluid conduit 12). In some embodiments, these locations of outlet aperture(s) 20A" and/or fluid outlet 20" may be as transversely far away from central channel axis 30 as may be permitted by bore 22A of fluid flow channel 22 or by fluid conduit 12 generally.

Figure 6A:
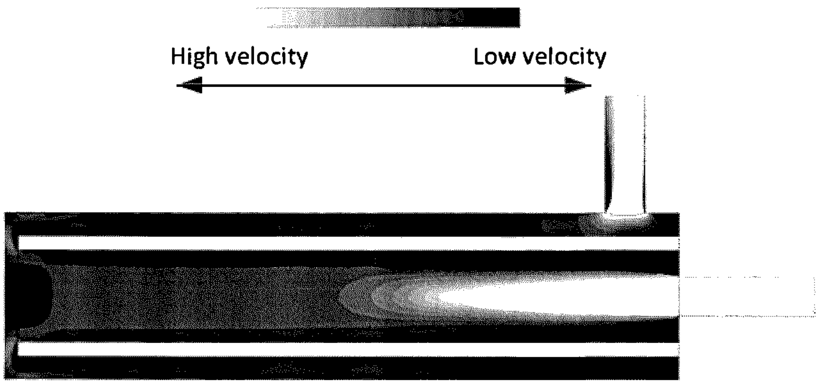
FIGS. 6A-6C show various simulation plots of the fluid velocity distribution for the reactor of FIG. 1C.
Figure 6B:
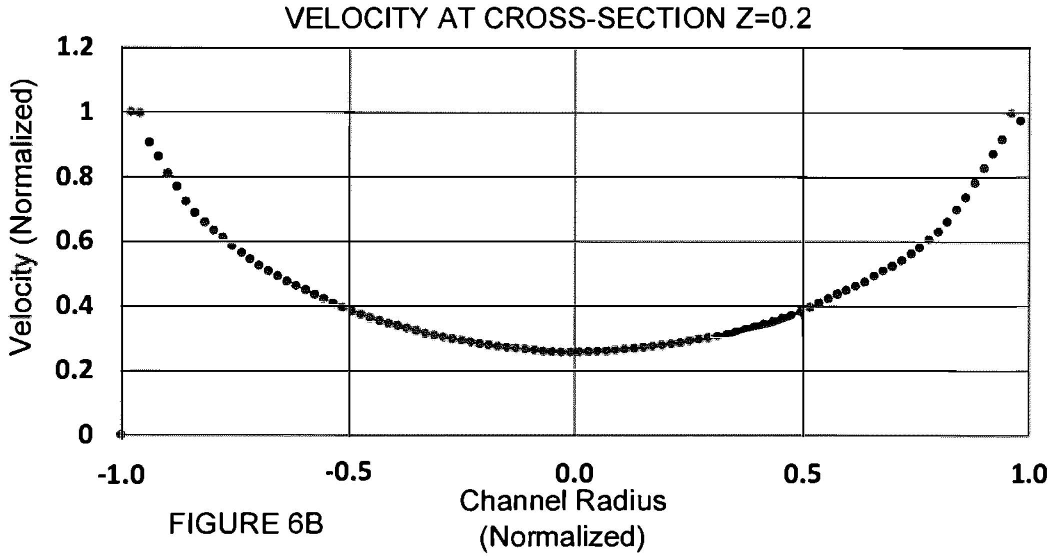
Figure 6C:
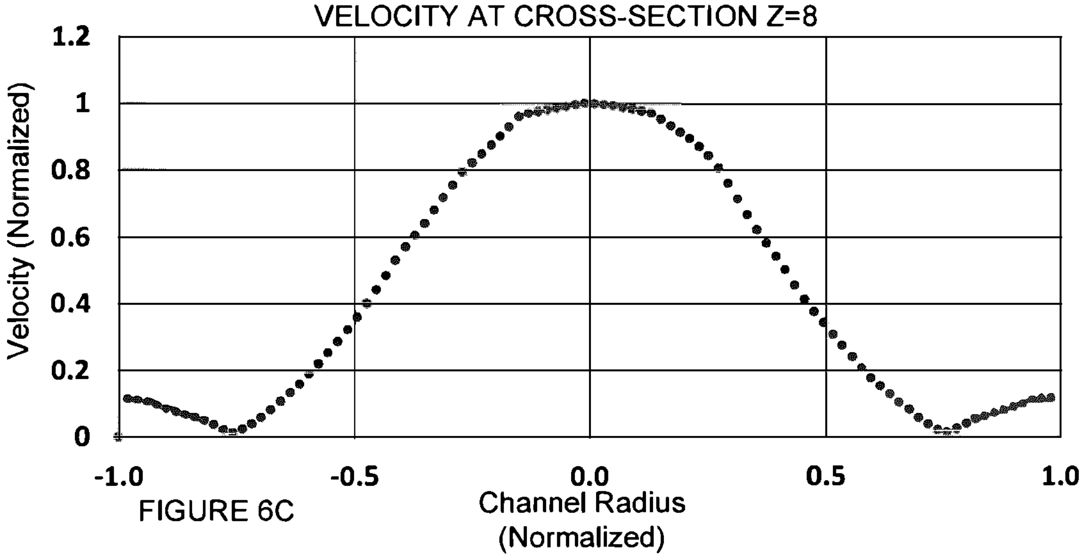

With outlet aperture(s) 20A" and/or fluid outlet 20" exhibiting these properties, reactor 10C may exhibit the same properties of reactor 10A that for cross-sections of the bore 22A of fluid flow channel 22 located relatively close to UV emitter 14 or close to outlet aperture(s) 20A", the fluid velocity may be relatively high at some locations relatively far from central channel axis 30 (e.g. at locations directly upstream from or adjacent to outlet apertures 20A") and relatively low at locations relatively close to central channel axis 30. In other respects, reactor 10C may have features similar to those of reactor 10A described herein. FIGS. 6A-6C show plots analogous to those of FIGS. 4A-4C for reactor 10C, except that FIG. 6B is taken at z=0.2 (as opposed to Z=0.5 for FIG. 4B) and FIG. 6C is taken at z=8 (as opposed to z=10 for FIG. 4C). FIGS. 6A-6C show that, for cross-sections closer to UV emitter 14 (low Z values in the illustrated embodiment (e.g. FIG. 6B)), the fluid velocity may be higher at some locations relatively far from central channel axis 30 and lower at locations nearer to central channel axis 30 and that, for cross-sections distal from UV emitter 14 (high Z values in the illustrated embodiment (e.g. FIG. 6C)), the fluid velocity may be lower at locations spaced transversely apart from central channel axis 30 and is higher at locations nearer to central channel axis 30.

FIG. 1D illustrates a cross-sectional view of a UV reactor 10D according to another particular example embodiment. Reactor 10D is similar to reactor 10C in many respects and similar features of reactor 10D are referred to with similar reference numerals to those of reactor 10C. Reactor 10D differs from reactor 10C only in the shape of its outlet conduit 20C'" at locations away from its outlet aperture 20A'". Specifically, outlet conduit 20C'" of reactor 10D does not extend transversely to reach its connecting aperture 20B'" and instead extends longitudinally (anti-parallel to the flow direction) to reach its connecting aperture 20B'". In general, at locations away from their outlet apertures, the outlet conduits of fluid outlets of any of the reactors described herein may have any suitable shape. In other respects, reactor 10D may have features similar to those of reactor 10C described herein.

FIGS. 3A-3D illustrate cross-sectional views of UV reactors 50A, 50B, 50C, 50D according to particular example embodiments. Reactors 50A, 50B, 50C, 50D of FIGS. 3A-3D are respectively similar to reactors 10A, 10B, 10C, 10D of FIGS. 1A-1D, except that the direction of flow is reversed (e.g. longitudinal flow direction 24 is reversed to become longitudinal flow direction 64) and fluid inlets 18, 18', 18", 18'" of reactors 10A, 10B, 10C, 10D become (and have the features of) fluid outlets 58, 58', 58", 58'" of reactors 50A, 50B, 50C, 50D and fluid outlets 20, 20', 20", 20'" of reactors 10A, 10B, 10C, 10D become (and have the features of) fluid inlets 60, 60', 60", 60'" of reactors 50A, 50B, 50C, 50D. Other features of reactors 50A, 50B, 50C, 50D have similar features to the features of reactors 10A, 10B, 10C, 10D and may be referred to herein using similar reference numerals to those used for reactors 10A, 10B, 10C, 10D (not all of which are expressly shown in the FIGS. 3A-3D illustrations).

In the embodiments of FIGS. 3A-3D, UV emitter 14 may be located relatively proximate to fluid inlet 60, 60', 60", 60'" (referred to hereinafter collectively and individually as fluid inlet 60) at the inlet end of bore 22A) and relatively distal from fluid outlet 58, 58', 58", 58'" (referred to hereinafter collectively and individually as fluid outlet 58), with the principal optical axis of UV emitter 14 being oriented generally parallel to, and in the same direction as, longitudinal fluid flow direction 64. Fluid conduit 12 may comprise a cross-sectional wall 36 at one end thereof. The cross-sectional wall 36 may define an outlet aperture 58A for fluid outlet 58 (where fluid outlet 58 opens into fluid flow channel 22) or may otherwise support fluid outlet 58. Outlet aperture 58A and/or fluid outlet 58 may be centrally located in cross-sectional wall 36. Central channel axis 30 may project through outlet aperture 58A and/or fluid outlet 58. A cross-section of outlet aperture 58A and/or fluid outlet 58 may be circularly symmetric about a point that is located on central channel axis 30. With outlet aperture 58A and/or fluid outlet 58 exhibiting these properties, for cross-sections of the bore 22A of fluid flow channel 22 located relatively distal from UV emitter 14 or close to outlet aperture 58, the fluid velocity may be relatively low at locations that are relatively far from central channel axis 30 and relatively high at locations relatively close to central channel axis 30.

The solid-state UV emitter 14 may be supported in housing 32 such that the principal optical axis of solid-state UV emitter 14 is at least generally aligned with central channel axis 30. In some embodiments (e.g. in reactor 50A of FIG. 3A), housing 32 itself may itself be supported (e.g. by one or more brackets 40) such that the principal optical axis of solid-state UV emitter 14 is at least generally aligned with central channel axis 30 and such that fluid can still flow through fluid inlet 60. The one or more brackets 40 may extend from outer conduit-defining wall 13 of the fluid conduit 12 to housing 32. The one or more brackets 40 may extend across the inlet conduit(s) 60C of the fluid inlet 60. In some embodiments, brackets 40 may be fabricated from perforated materials that permit fluid flow therethrough. In some embodiments, brackets 40 may comprise one or more annular rings of perforated material. An inlet aperture 60A, 60A', 60A", 60A'" for the fluid inlet 60, 60', 60", 60'" may be defined by a combination of outer conduit-defining wall 13 (possibly including bore-defining wall 28), housing 32 and/or the one or more brackets 40 (where present) or fluid inlet 60, 60', 60", 60'" may otherwise be supported by a combination of outer conduit-defining wall 13 (possibly including bore-defining wall 28), housing 32 and/or the one or more brackets 40 (where present). In some embodiments, the inlet conduit 60C of fluid inlet 60 of the FIG. 3A reactor 50A may have generally annular cross-sections at locations between inlet aperture(s) 60A and connecting aperture(s) 60B wherein these cross-sections may be defined by outer conduit-defining wall 13 and housing 32 (except in regions where this annular shape is interrupted by the one or more brackets 40). This (generally annularly shaped cross-sections for inlet conduit 60, 60', 60", 60'") may not be necessary. With these configurations, inlet aperture(s) 60A, 60A', 60A", 60A"' may be located at location(s) that are spaced transversely apart from central channel axis 30 (e.g. as transversely far away as may be permitted by the bore 22A of fluid flow channel 22 or by fluid conduit 12 generally). Consequently, with inlet aperture 60A, 60A', 60A", 60A"' and/or fluid inlet 60, 60', 60", 60"' exhibiting these properties, for cross-sections of the bore 22A of fluid flow channel 22 located relatively close to UV emitter 14 or close to inlet aperture(s) 60A, 60A', 60A", 60A"', the fluid velocity may be relatively high at some locations relatively far from central channel axis 30 (e.g. at locations directly downstream from or adjacent to inlet apertures 60A, 60A', 60A", 60A"') and relatively low at locations relatively close to central channel axis 30.

Thus when shaped with fluid outlet 58 located transversely near to central channel axis 30 and with fluid inlet 60, 60', 60", 60"' located toward the transverse cross-sectional edge(s) of fluid conduit 12, the combined effect for UV reactors 50A, 50B, 50C, 50D may be that: (1) for cross-sections of bore 22A of fluid flow channel 22 located relatively close to fluid outlet 58, the fluid velocity may be relatively low at locations that are relatively far from central channel axis 30 and relatively high at locations relatively close to central channel axis 30; and (2) for cross-sections of the bore 22A of fluid flow channel 22 located relatively close to fluid inlet 60, 60', 60", 60"', the fluid velocity may be relatively high at some locations relatively far from central channel axis 30 (e.g. at locations directly downstream from or adjacent to inlet apertures 60A, 60A', 60A", 60A"') and relatively low at locations relatively close to central channel axis 30. UV emitter 14 and lens(es) 16A of reactors 50A, 50B, 50C, 50D are located at the inlet end of fluid conduit 12 for directing radiation in a general direction that is parallel to the fluid flow direction 64 through fluid conduit 12. Further, lens(es) 16A of UV reactors 50A, 50B, 50C, 50D may be configured such that: (1) for cross-sections of the bore 22A of the fluid flow channel 22 located relatively distal from UV emitter 14 or relatively close to fluid outlet 58, the radiation fluence rate profile may be relatively low at locations relatively far from central channel axis 30 and relatively high at locations nearer to central channel axis 30; and (2) for cross-sections of the bore 22A of fluid flow channel 22 located relatively close to UV emitter 14 or close to fluid inlet 60, 60', 60", 60"', the radiation fluence rate profile may be relatively high at locations relatively far from central channel axis 30 and relatively low for locations nearer to central channel axis 30. Thus, the radiation fluence rate in reactors 50A, 50B, 50C, 50D may be relatively high in regions where the fluid velocity is relatively high and the radiation fluence rate in reactors 50A, 50B, 50C, 50D may be relatively low in regions where the fluid velocity is relatively low. Accordingly, the UV fluence (UV dose, which is a function of UV fluence rate and residence time (inverse of velocity) imparted on the fluid as it traverses bore 22A of fluid flow channel 22 of reactors 50A, 50B, 50C, 50D may be relatively uniform.

Figure 7A:
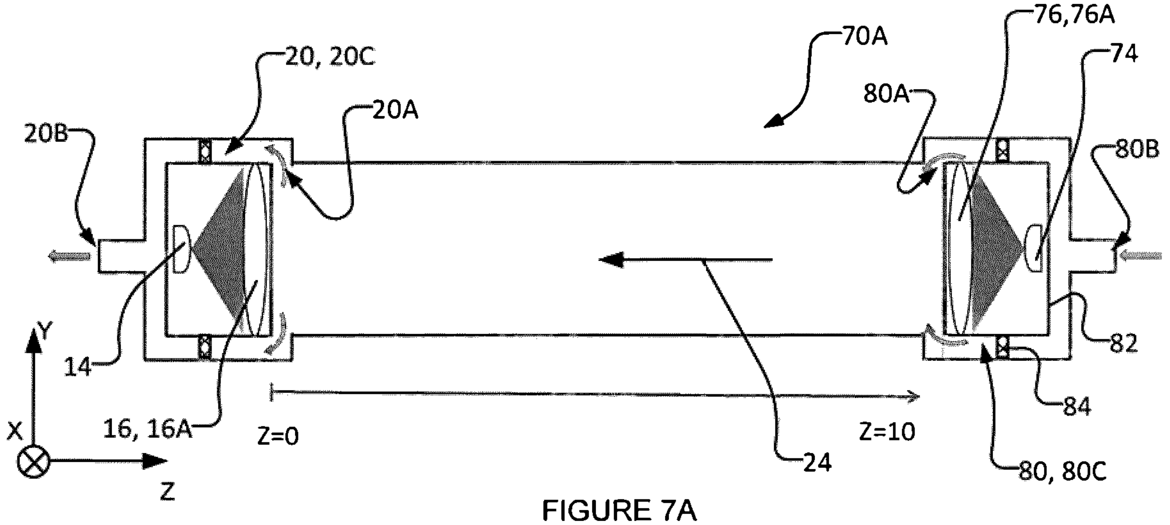
FIGS. 7A and 7B illustrate cross-sectional views of UV reactors according to particular example embodiments.

FIG. 7A illustrates a cross-sectional view of a reactor 70A according to another embodiment. Reactor 70A is similar to reactor 10A (FIG. 1A) and reactor 50A (FIG. 3A) in many respects and similar features of reactor 70A are referred to with similar reference numerals to those of reactors 10A and 50A, not all of which are expressly shown in the drawings. Reactor 70A differs from reactor 10A in that reactor 70A incorporates a second solid-state UV emitter 74; and a second radiation-focusing element 76 comprising one or more secondary lenses 76A which may be substantially similar to (but oriented in an antiparallel direction to) UV emitter 14 and lens(es) 16A. A principal optical axis of second UV emitter 74 may be anti-parallel to the principal optical axis of first UV emitter 14. The principal optical axis of the first UV emitter 14, the principal optical axis of second UV emitter 74, the optical axes of the one or more lenses 16A, the optical axes of the one or more secondary lenses 76A and central channel axis 30 of at least the longitudinally central portion 22B of fluid flow channel 22 may be co-linear or co-axial. Second solid-state UV emitter 74, second radiation focusing element 76 and secondary lens(es) 76A may comprise any of the features of solid-state emitter 14, radiation focusing element 16 and lens(es) 16. Lens(es) 76A may be positioned in a second radiation path of radiation emitted from second UV emitter 74 for directing radiation from second UV emitter 76 to impinge on the fluid flowing in fluid flow channel 22 and to thereby provide a second radiation fluence rate profile within bore 22A of fluid flow channel 22. Lens(es) 76A may be configured to provide a second radiation fluence rate profile wherein, for secondary cross-sections of bore 22A of fluid flow channel 22 located relatively close to second UV emitter 74 (e.g. high Z values in the illustrated FIG. 7A embodiment), the second radiation fluence rate profile may be relatively high at locations that are relatively far from central channel axis 30 and relatively low at locations nearer to central channel axis 30 and wherein, for secondary cross-sections of bore 22A of fluid flow channel 22 located relatively distal from second UV emitter 74 (e.g. low Z values in the illustrated FIG. 7A embodiment), the second radiation fluence rate profile may be relatively low at locations that are relatively far from central channel axis 30 and relatively high at locations that are nearer to central channel axis 30.

As discussed above, lens(es) 16A may be configured to provide a first radiation fluence rate profile wherein, for cross-sections of bore 22A of fluid flow channel 22 located relatively close to first UV emitter 14 (e.g. low Z values in the illustrated FIG. 7A embodiment), the first radiation fluence rate profile may be relatively high at locations that are relatively far from central channel axis 30 and relatively low at locations nearer to central channel axis 30 and wherein, for cross-sections of bore 22A of fluid flow channel 22 located relatively distal from first UV emitter 14 (e.g. high Z values in the illustrated FIG. 7A embodiment), the first radiation fluence rate profile may be relatively low at locations that are relatively far from central channel axis 30 and relatively high at locations that are nearer to central channel axis 30.

Figure 8A:
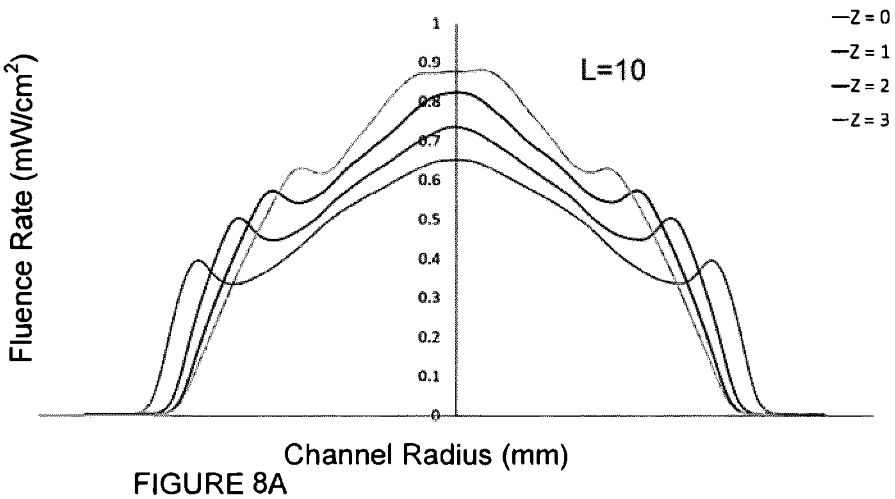
FIGS. 8A-8C show radiation fluence rate profiles for cross-sections of the bore of the fluid flow channel of the FIG. 7A reactor for a particular fluid flow channel of a particular length.
Figure 8B:
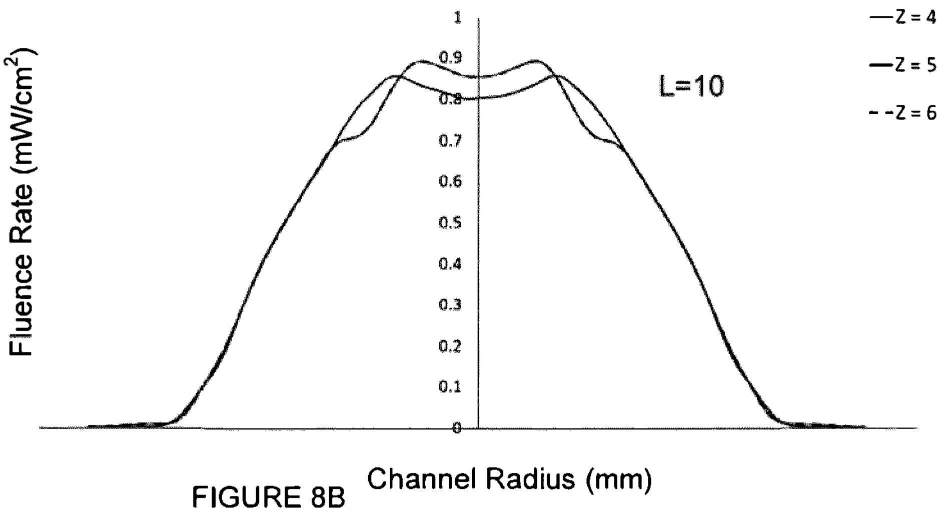
Figure 8C:
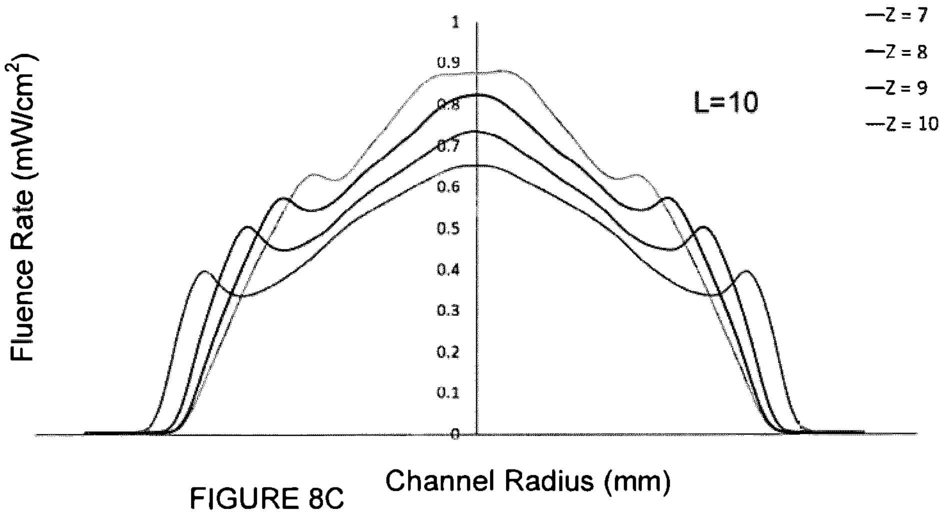

Accordingly, for reactor 70A, the total radiation fluence rate may then be a superposition of the first radiation fluence profile (caused by radiation emitted from first UV emitter 14 and shaped by lens(es) 16A) and the second radiation fluence rate profile (caused by radiation emitted from second UV emitter 74 and shaped by lens(es) 76A). FIGS. 8A-8C illustrate show total radiation fluence rate profiles for various cross-sections of the bore 22A of fluid flow channel 22 of the FIG. 7A reactor 10A at various cross-sectional locations (e.g. at various Z-values) for a reactor 70A with a total longitudinal length (in the Z-direction) of L=10 cm, where the UV transmittance of the fluid is set to be 95%. FIGS. 8A-8C are analogous to the plots of FIGS. 2A-2C discussed above, for reactors 10A, 10B, 10C, 10D and 50A, 50B, 50C, 50D. The Y-axes of the plots of FIGS. 8A-8C represent total radiation fluence rate (in $mW/cm^2$). The X-axes of the plots of FIGS. 8A-8C represent radial distances from central channel axis 30 (e.g. along the X-axis shown in FIG. 7A or along any other suitable radial direction in the case where bore 22A is circular in cross-section). It will be appreciated that the origins of the X-axes of the plots of FIGS. 8A-8C represent locations on central channel axis 30 and larger values of X on the plots of FIGS. 8A-8C represent locations that are relatively far from central channel axis 30.

Figure 9A:
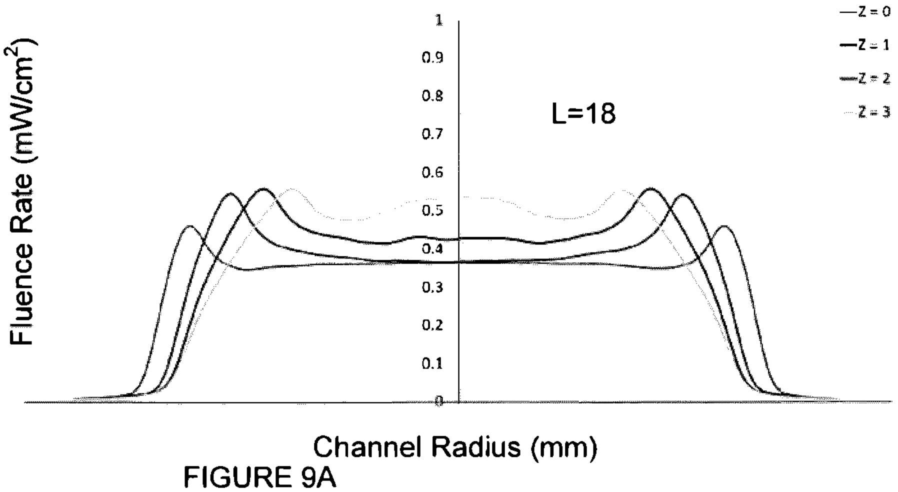
FIGS. 9A-9D show radiation fluence rate profiles for cross-sections of the bore of the fluid flow channel of the FIG. 7A reactor for a particular fluid flow channel of a particular length
Figure 9B:
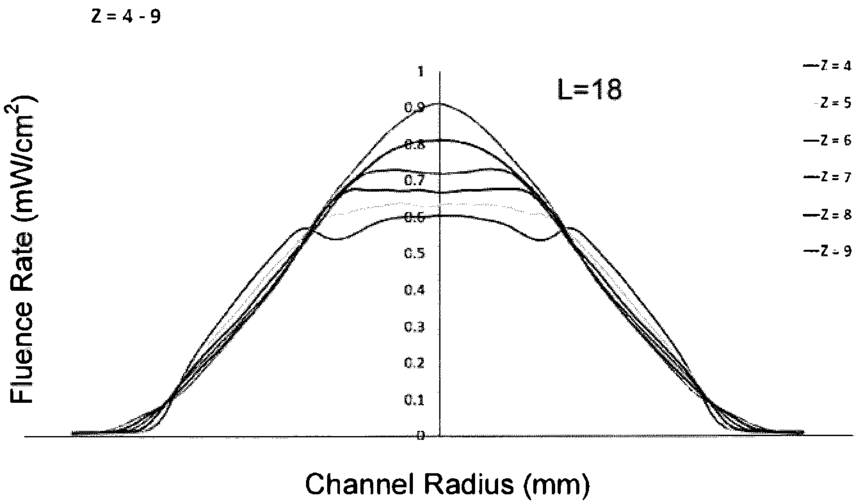
Figure 9C:
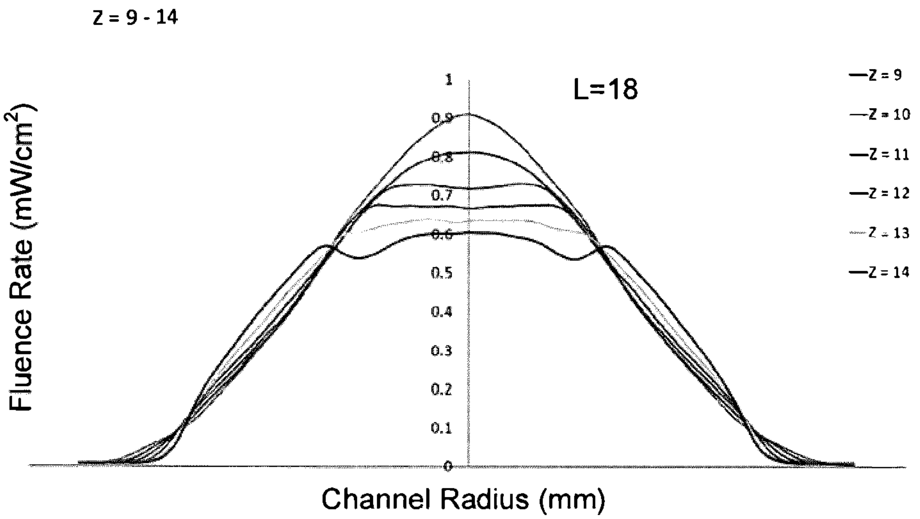
Figure 9D:
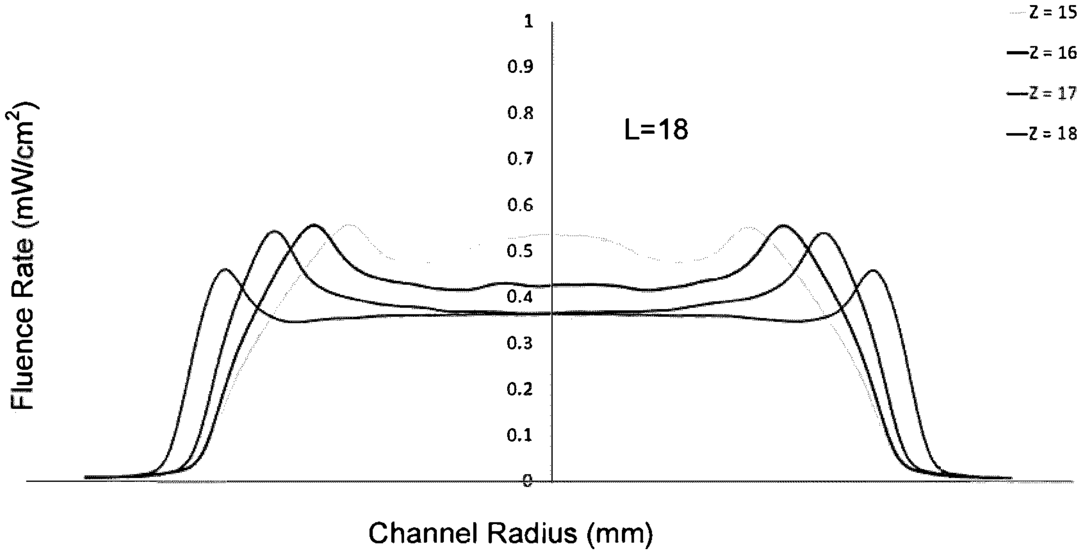

FIGS. 9A-9D illustrate the total radiation fluence rate profiles for various cross-sections of the bore 22A of fluid flow channel 22 of the FIG. 7A reactor 10A at various cross-sectional locations (e.g. at various Z-values) for a reactor 70A with a total longitudinal length (in the Z-direction) of L=18 cm, where the UV transmittance of the fluid is set to be 95%. FIGS. 9A-9D are also analogous to the plots of FIGS. 2A-2C discussed above, for reactors 10A, 10B, 10C, 10D and 50A, 50B, 50C, 50D. Comparing the plots of FIGS. 8A-8C to the plots of FIGS. 9A-9D, it can be seen that for the reactor 70A having a shorter longitudinal length (FIGS. 8A-8C), the total irradiance profiles for cross-sections relatively close to the first and second UV emitters 14, 74 (i.e. the relatively low Z values of FIG. 8A and the relatively high Z values of FIG. 8C) exhibit total fluence rates that may be relatively high at locations relatively close to central channel axis 30 and exhibit total fluence rates that may be relatively low at locations relatively distal from central channel axis 30. In contrast, however, for the reactor 70A having a longer longitudinal length (FIGS. 9A-9D), the total irradiance profiles for cross-sections relatively close to the first and second UV emitters 14, 74 (i.e. the relatively low Z values of FIG. 9A and the relatively high Z values of FIG. 9D) exhibit total fluence rates that may be relatively high at some locations that are transversely spaced apart (distal) from central channel axis 30 and total fluence rates that may be relatively low at locations that are nearer to central channel axis 30. Also, FIGS. 9B and 9C show that for the reactor 70A having a longer longitudinal length, the total irradiance profiles for cross-sections relatively close to the longitudinal center of reactor 70A (e.g. for Z=4 to Z=14 in the illustrated plots of FIGS. 9B and 9C), may exhibit relatively low total fluence rate at locations relatively transversely spaced apart from central channel axis 30 and may exhibit relatively high total fluence rate at locations nearer to central channel axis 30.

Together, FIGS. 8A-8C and 9A-9D show that the radiation fluence rate profile of reactor 70A may be tuned by adjusting the longitudinal length of reactor 70A or at least of bore 22A. Advantageously, for the relatively long reactor 70A shown in FIGS. 9A-9D: (1) the total irradiance profiles for cross-sections relatively close to the first and second UV emitters 14, 74 exhibit total fluence rates that may be relatively high at some locations that are transversely spaced apart (distal) from central channel axis 30 and total fluence rates that may be relatively low at locations that are nearer to central channel axis 30; and (2) the total irradiance profiles for cross-sections relatively close to the longitudinal center of reactor 70A may exhibit relatively low total fluence rate at locations relatively transversely spaced apart from central channel axis 30 and may exhibit relatively high total fluence rate at locations nearer to central channel axis 30. As will be explained in more detail below, because of the fluid velocity profile in reactor 70A, this fluence rate profile can create relatively uniform UV dose distribution in reactor 70A.

Reactor 70A of FIG. 7A also differs from reactor 10A in that reactor 70A comprises a secondary housing 82 optionally supported by brackets 84 that is substantially similar to housing 32 of reactor 10A, except that secondary housing 82 is oriented in an antiparallel to housing 32 and secondary housing 82 houses second UV emitter 74 and secondary lenses 76A. Reactor 70A of FIG. 7A also comprises a fluid inlet 80 (having features similar to those of fluid inlet 60 of reactor 50A, including inlet aperture 80A, connecting aperture 80B and inlet conduit 80C similar to inlet aperture 60A, connecting aperture 60B and inlet conduit 60C). Reactor 70A may comprise a fluid outlet 20 that is substantially similar to fluid outlet 20 of reactor 10A described herein. With this configuration of fluid inlet 80 and fluid outlet 20, the fluid velocities will tend to be larger at transverse locations away from central channel axis 30 for cross-sections of bore 22A that are relatively close to fluid inlet 80 (e.g. high Z values in the illustrated FIG. 7A embodiment) and for cross-sections of bore 22A that are relatively close to fluid outlet 20 (e.g. low Z values in the illustrated FIG. 7 embodiment). Further, with this configuration of fluid inlet 80 and fluid outlet 20, for cross-sections of bore 22A that are relatively central (e.g. spaced apart from both fluid inlet 80 and fluid outlet 20 and relatively mid-range Z values), the fluid velocities will tend to be relatively lower at transverse locations spaced further apart from central channel axis 30 and relatively higher for transverse locations that are relatively nearer to central channel axis 30.

Figure 10A:
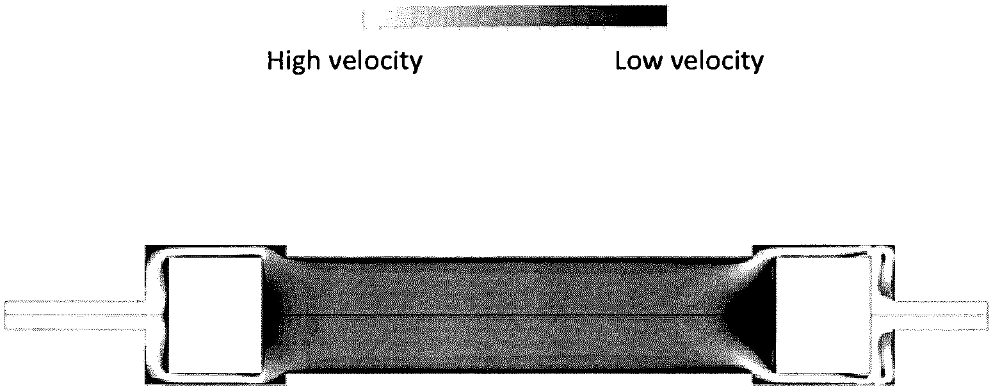
FIGS. 10A-10D show various plots of the fluid velocity distribution for the reactor of FIG. 7A.
Figure 10B:
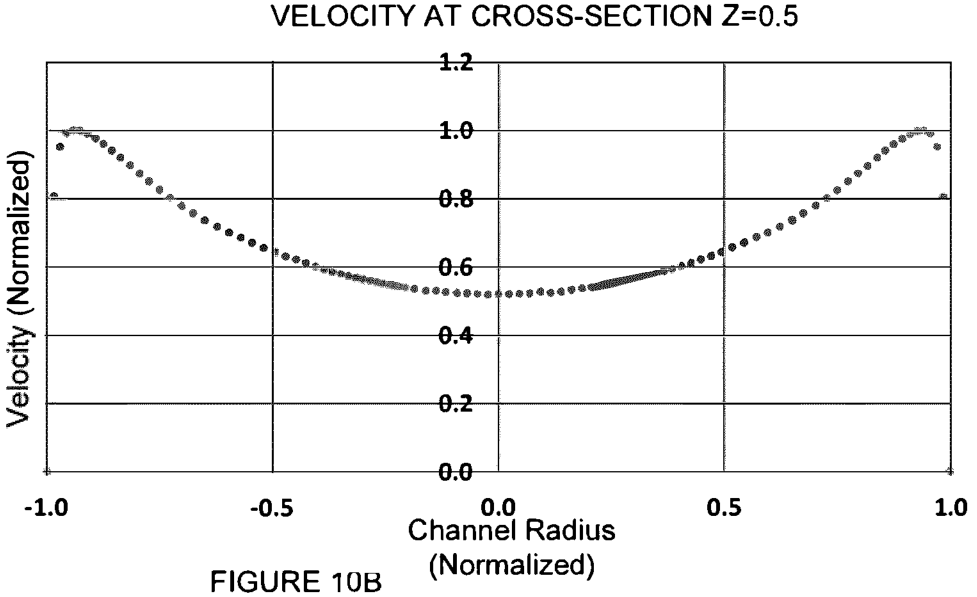
Figure 10C:
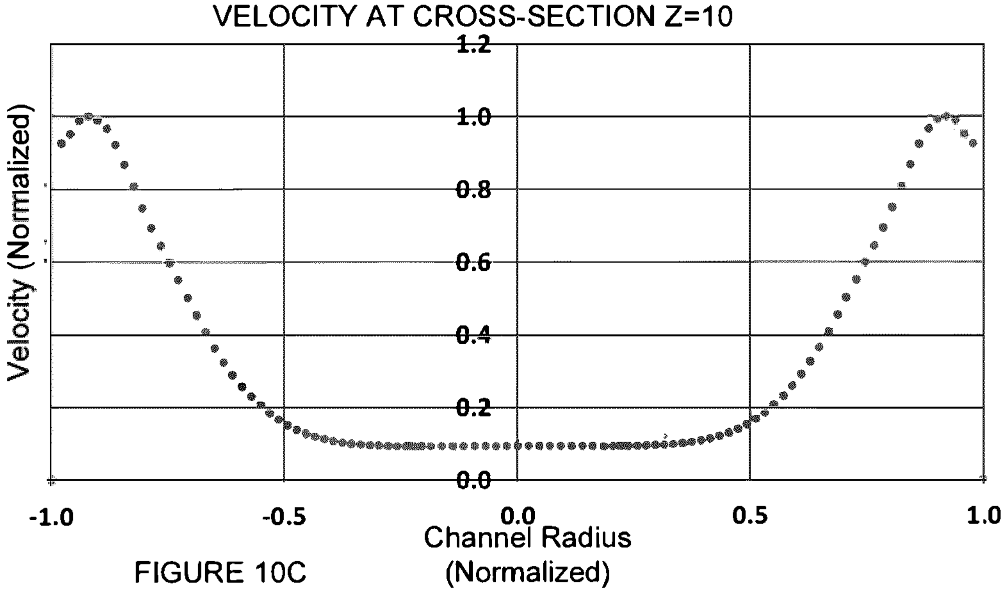
Figure 10D:
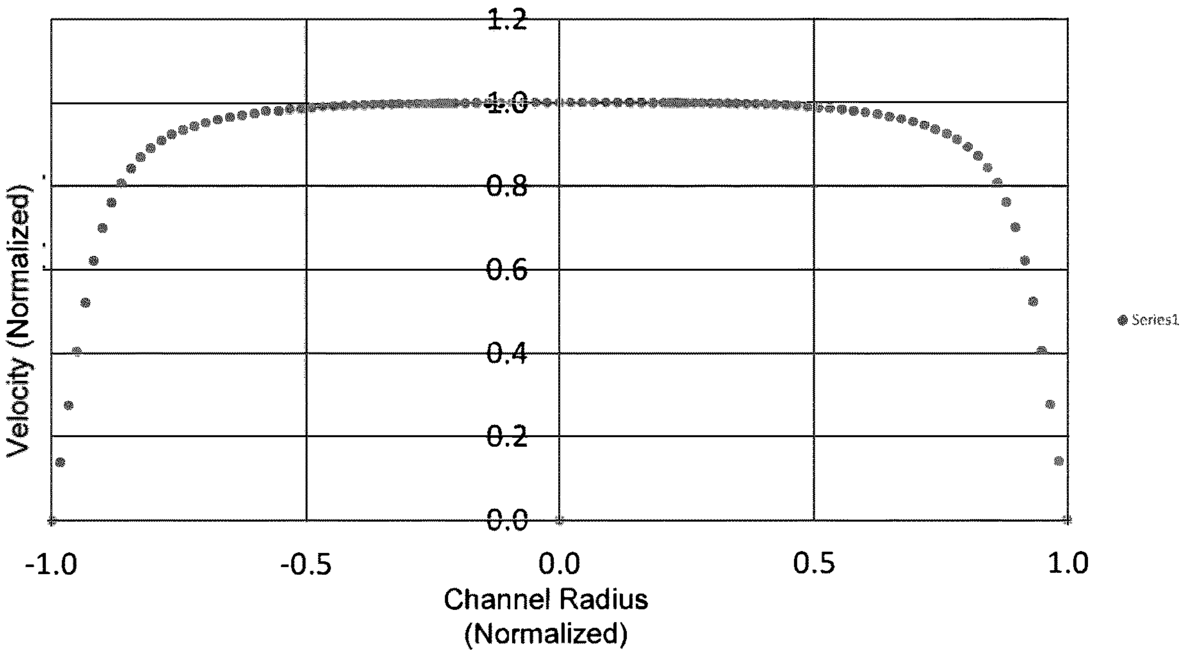

FIGS. 10A-10D show simulation plots similar to those of FIGS. 4A-4C for reactor 70A, where the length is L=10 cm. FIG. 10A is a fluid velocity mapping showing fluid velocities for different regions of reactor 70A with relatively high local fluid velocities having lighter colors and relatively low local fluid velocities having darker colors. FIG. 10B shows a plot of fluid velocity versus distance from central channel axis 30 at the cross-section of reactor 70A corresponding to Z=0.5 (i.e. relatively close to first UV emitter 14) and FIG. 10C shows a plot of fluid velocity versus distance from central channel axis 30 at the cross-section corresponding to Z=10 (i.e. relatively close to second UV emitter 74). FIG. 10D shows a plot of fluid velocity at Z=5 (i.e. at a relatively central longitudinal location that is spaced apart from both first UV emitter 14 and from second UV emitter 74). In the plots of FIGS. 10B-10D, central channel axis 30 corresponds to the origins of the X-axes. FIGS. 10A-10D show that for reactor 70A of the FIG. 7A embodiment, for cross-sections closer to first UV emitter 14 (low Z values in the illustrated embodiment (e.g. FIG. 10B)) and for cross-sections closer to second UV emitter 74 (high Z values in the illustrated embodiment (e.g. FIG. 10C), the fluid velocity may be higher at some locations relatively far from central channel axis 30 and may be lower at locations nearer to central channel axis 30 and that, for longitudinally central cross-sections distal from both first and second UV emitters 14, 74 (mid-range Z values in the illustrated embodiment (e.g. FIG. 10D)), the fluid velocity may be lower at locations spaced transversely apart from central channel axis 30 and may be higher at locations nearer to central channel axis 30. For longer reactors (e.g. reactors having lengths of L>=10 cm, the fluid velocity results are similar to those shown in FIGS. 10A-10D, with fluid velocities being similar to those of FIGS. 10B and 10C for Z less than or equal to approximately 3 and Z greater than or equal to $L_{max}$−3 and fluid velocities being similar to those of FIG. 10D for intervening Z values.

Thus, when shaped with the fluid inlet 80 and fluid outlet 20 shown in FIG. 7A with inlet aperture(s) and outlet aperture(s) located toward the transverse cross-sectional edge(s) of fluid conduit 12, the combined effect for UV reactor 70A is that: (1) for cross-sections of bore 22A of fluid flow channel 22 located relatively close to fluid inlet 80 and relatively close to fluid outlet 20 (e.g. relatively close to first and second emitters 14, 74), the fluid velocity may be relatively high at some locations that are relatively far from central channel axis 30 (e.g. at locations directly upstream from or adjacent to outlet aperture(s) 20A and at locations directly downstream from or adjacent to inlet aperture(s) 80A) and relatively low at locations relatively close to central channel axis 30; and (2) for longitudinally central cross-sections of the bore 22A of fluid flow channel 22 (spaced apart from fluid inlet 80 and from fluid outlet 20 and from first and second emitters 14, 74), the fluid velocity may be relatively low at locations relatively far from central channel axis 30 and relatively high at locations relatively close to central channel axis 30. Further, lens(es) 16A, 76A of UV reactor 70A and the longitudinal dimension of reactor 70A may be configured such that: (1) for cross-sections of the bore 22A of the fluid flow channel 22 located relatively close to first UV emitter 14 and for cross-sections of the bore 22A of the fluid flow channel 22 located relatively close to second UV emitter 74, the radiation fluence rate profile may be relatively high at locations relatively far from central channel axis 30 and relatively low at locations nearer to central channel axis 30 (see FIGS. 9A and 9D); and (2) for longitudinally central cross-sections of the bore 22A of the fluid flow channel 22 (i.e. cross-sections spaced apart from fluid inlet 80, fluid outlet 20 and spaced apart from first and second UV emitters 14, 74), the radiation fluence rate profile may be relatively low at locations relatively far from central channel axis 30 and relatively high at locations nearer to central channel axis 30 (see FIGS. 9B and 9C). Thus, the radiation fluence rate in reactor 70A may be configured to be relatively high in regions where the fluid velocity is relatively high and the radiation fluence rate in reactor 70A may be configured to be relatively low in regions where the fluid velocity is relatively low. Accordingly, the UV fluence (UV dose), which is a function of UV fluence rate and residence time (inverse of velocity), imparted on the fluid as it traverses bore 22A of fluid flow channel 22 of reactor 70A may be relatively uniform.

Figure 7B:
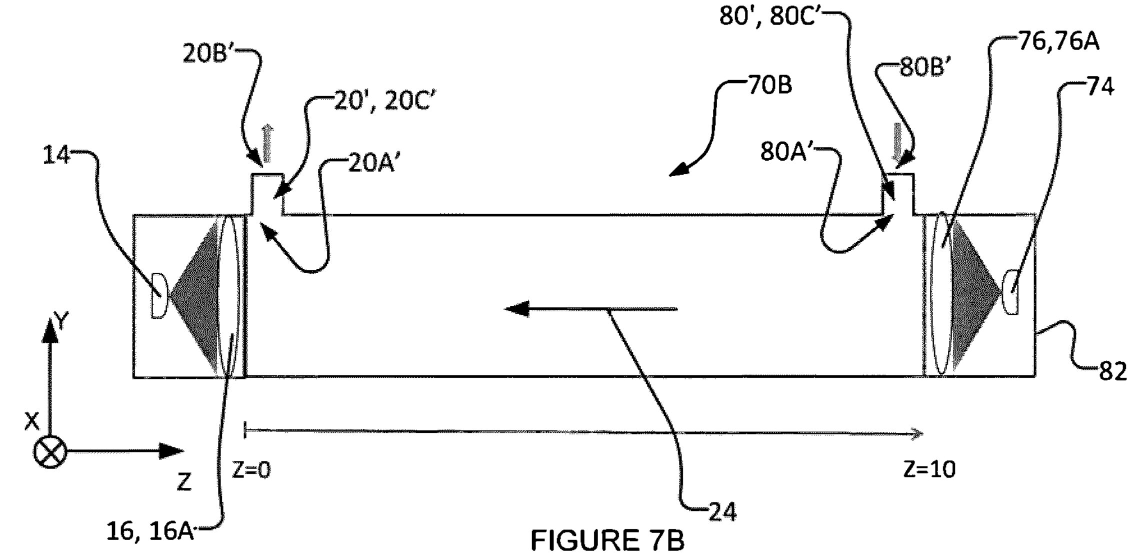

FIG. 7B illustrates a cross-sectional view of a UV reactor 70B according to another particular example embodiment. Reactor 70B is similar to reactor 70A in many respects and similar features of reactor 70B are referred to with similar reference numerals to those of reactor 70A, although not all of these reference numerals are shown in the FIG. 7B illustration. Reactor 70B differs from reactor 70A primarily in that reactor 70B has a fluid outlet 20' that is located and shaped differently from outlet 20 of reactor 70A and a fluid inlet 80' that is located and shaped differently from inlet 80 of reactor 70A. Specifically, outlet 20' of reactor 70B is the same as outlet 20' of reactor 10B (FIG. 1B) described herein and inlet 80' is the same as inlet 60' of reactor 50B (FIG. 3B) described herein except for inlet 80' is oriented antiparallel to inlet 60' of reactor 50B.

As can be seen from FIG. 7B, reactor 70B may include a fluid outlet 20' that extends generally transversely (i.e. orthogonal to the longitudinal fluid flow direction 24) from fluid flow channel 22. Fluid outlet 20' may comprise an outlet aperture 20A' that is located at an outlet end 34 of reactor 70B and is defined either by bore-defining wall 28 of fluid flow conduit 22 or by a combination of bore-defining wall 28 and housing 32. While not shown in the illustrated embodiment, reactor 70B may comprise a plurality of fluid outlets 20', extending from fluid flow channel 22 in different and spaced apart in transverse (e.g. circumferential) directions. Each of these fluid outlets 20' may be similar to fluid outlet 20' shown and described herein. As is the case, with fluid outlet 20 of reactor 10A, fluid outlet 20' and/or outlet aperture 20A' may be spaced transversely apart from central channel axis 30 (i.e. toward the cross-sectional edge(s) of fluid conduit 12). In some embodiments, these locations of outlet aperture(s) 20A' and/or fluid outlet 20' may be as transversely far away from central channel axis 30 as may be permitted by bore 22A of fluid flow channel 22 or by fluid conduit 12 generally.

As can be seen from FIG. 7B, reactor 70B may include a fluid inlet 80' that extends generally transversely (i.e. orthogonal to the longitudinal fluid flow direction 24) from fluid flow channel 22. Fluid inlet 80' may comprise an inlet aperture 80A' that is located at an inlet end 38 of reactor 70B and is defined either by bore-defining wall 28 of fluid flow conduit 22 or by a combination of bore-defining wall 28 and housing 82. While not shown in the illustrated embodiment, reactor 70B may comprise a plurality of fluid inlets 80', extending from fluid flow channel 22 in different and spaced apart in transverse (e.g. circumferential) directions. Each of these fluid inlets 80' may be similar to fluid inlet 80' shown and described herein. As is the case, with fluid inlet 60 of reactor 50B, fluid inlet 80' and/or inlet aperture 80A' may be spaced transversely apart from central channel axis 30 (i.e. toward the cross-sectional edge(s) of fluid conduit 12). In some embodiments, these locations of inlet aperture(s) 80A' and/or fluid inlet 80' may be as transversely far away from central channel axis 30 as may be permitted by bore 22A of fluid flow channel 22 or by fluid conduit 12 generally.

With outlet aperture(s) 20A' and/or fluid outlet 20' and inlet aperture 80A' and/or fluid inlet 80' exhibiting these properties, reactor 70B may exhibit the same properties of reactor 70A that for cross-sections of the bore 22A of fluid flow channel 22 located relatively close to outlet 20' (and first UV emitter 14) and for cross-sections of the bore 22A of fluid flow channel 22 located relatively close to inlet 80' (and second UV emitter 74), the fluid velocity may be relatively high at some locations relatively far from central channel axis 30 (e.g. at locations directly upstream from or adjacent to outlet apertures 20A' and/or at locations directly downstream from or adjacent to inlet apertures 80A') and relatively low at locations relatively close to central channel axis 30. For longitudinally central cross-sections of the bore 22A of fluid flow channel 22 (i.e. for cross-sections spaced apart from inlet 80' and outlet 20'), the fluid velocity may be relatively low at locations relatively far from central channel axis 30 and relatively high at locations relatively close to central channel axis 30. In other respects, reactor 70B may have features similar to those of reactor 70A described herein.

Figure 11A:
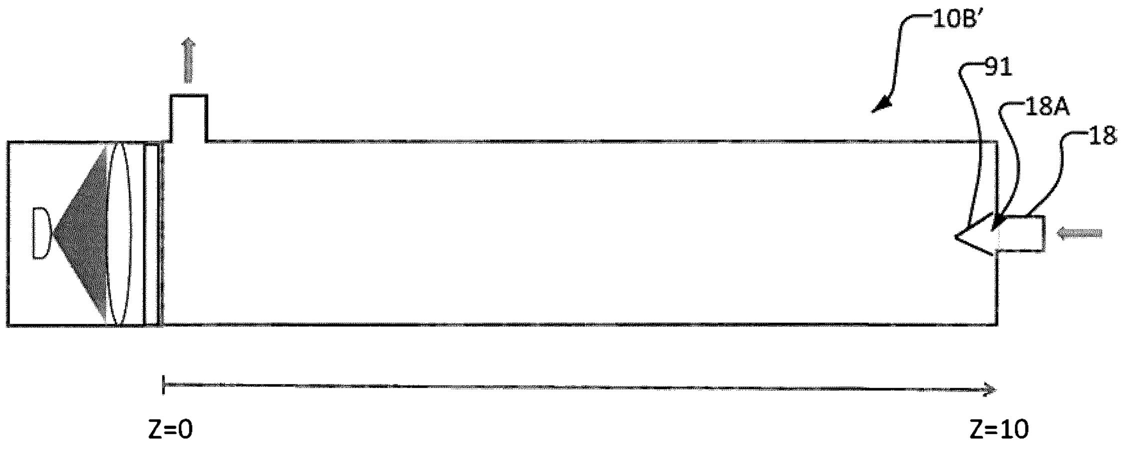
FIGS. 11A-11C show a number of exemplary reactors incorporating flow modifiers according to particular embodiments.
Figure 11B:
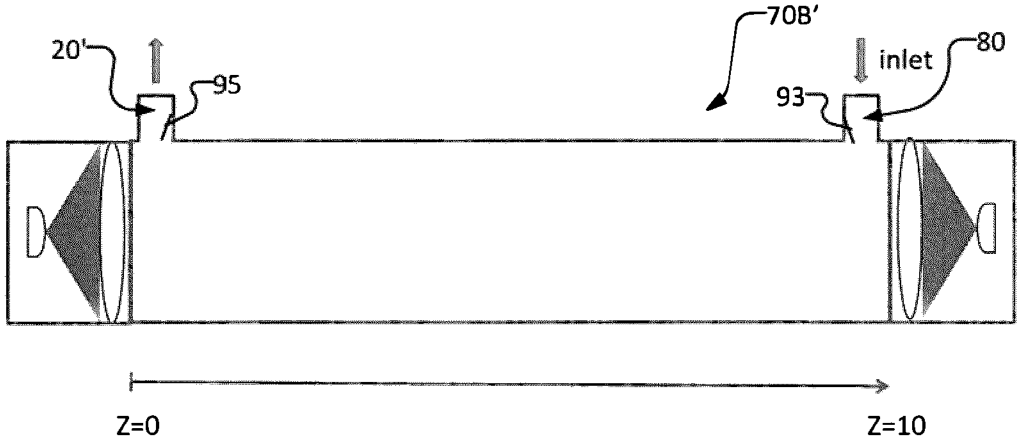
Figure 11C:
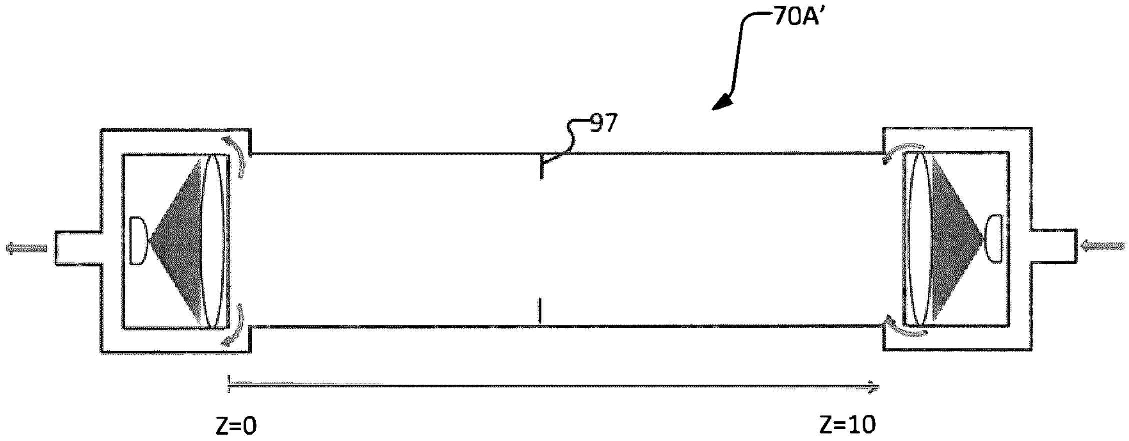

FIGS. 11A-11C show a number of exemplary reactors incorporating flow modifiers according to particular embodiments. FIG. 11A shows a reactor 10B' which is substantially similar to reactor 10B (FIG. 1B) except that reactor 10B' of FIG. 11A comprises a flow modifier 91 in a vicinity of fluid inlet 18. Specifically, flow modifier 91 is located just downstream of inlet aperture 18A, although flow modifier 91 could be located in inlet conduit 18C of fluid inlet 18. Flow modifier 91 may be a baffle, which may be shaped and/or positioned on the path of part of the flow going towards the areas of low fluence rates, to direct the flow (at least partially) away from the areas of low fluence rate. Further, flow modifier 91 may be shaped and/or positioned to provide mixing to the fluid between the areas of low and high fluence rates to prevent the flow going through the reactor while receiving low doses of UV. For example, flow modifier 91 may comprise a delta wing shaped mixer, a twisted tape shaped mixer and/or another form of vortex generator to create vortices in the flow and help with flow mixing. Flow modifier 91 may be suitably modified for use in a vicinity of the fluid inlets (e.g. just downstream from their inlet apertures) of any of the reactors described herein. FIG. 11B shows a reactor 70B' which is substantially similar to reactor 70B (FIG. 7B) except that reactor 70B' of FIG. 11B comprises a flow modifier 93 in a vicinity of fluid inlet 80 and a flow modifier 95 in a vicinity of fluid outlet 20'. Specifically, flow modifier 93 may be located just upstream of inlet aperture 80A, although flow modifier 93 could be located at other locations in a vicinity of fluid inlet 80. Flow modifier 93 can help with enhancing mixing of fluid in flow channel 22. Flow modifier 93 may additionally or alternatively redirect the flow to thereby help with preventing the fluid flow being channeled toward the bottom of the reactor where there may be relatively low fluence rates at the transverse locations in the middle of the reactor (at the bottom). Further, any significant flow channeling may effectively minimize the residence time of part of the fluid in the reactor and result in non-uniformity of the UV dose to the fluid. Similarly, flow modifier 95 may be located just downstream of outlet aperture 20A', although flow modifier 95 may be located at other locations in a vicinity of fluid outlet 20'. Flow modifier 95 may provide some resistance to fluid flow exiting the reactor, thereby help with mixing of the flow near the outlet. Flow modifier 93 may be suitably modified for use in a vicinity of the fluid inlets of any of the reactors described herein. Flow modifier 95 may be suitably modified for use in a vicinity of the fluid outlets of any of the reactors described herein. FIG. 11C shows a reactor 70A' which is substantially similar to reactor 70A (FIG. 7A) except that reactor 70A' of FIG. 11C comprises a flow modifier 97 which extends inwardly (e.g. toward central channel axis 30) from its bore-defining wall 28. Flow modifier 97 may be provided in the form of a ring and may redirect the fluid flow toward central channel axis 30, where there is more fluence rate than near the reactor wall, and to enhance mixing. Flow modifiers like flow modifier 97 may be placed at regions of the fluid flow channel 22 where there are low radiation fluence rates, for example near the conduit-defining wall 13 to minimize the impact of the flow modifier on blocking UV radiation. Flow modifier 97 may be used in the fluid flow channels 22 any of the reactors described herein. Any of flow modifiers 91, 93, 95, 97 may be made of UV reflective or UV transparent materials.

The body or housing for embodiments of any of the UV-LED reactors described herein may be made of aluminum, stainless steel, or of any other sufficiently rigid and strong material such as metal, alloy, high-strength plastic, and the like. In some embodiments, for example, a single channel reactor similar to a pipe, it may also be made of flexible material such as UV-resistance PVC and the like. Also, the various components of the UV-LED reactor may be made of different materials. Further, photocatalyst structures may be used in the any of the UV reactors described herein, for UV-activated photocatalytic reactions. The photocatalyst may be incorporated in the reactor either by being immobilized on porous substrate, where fluid passes through, and/or by being immobilized on a solid substrate, where fluid passes over. Further, photocatalysts may be combined with static mixers to provide multi-function components for any of the UV reactors described herein.

Further, the UV-LED reactor may incorporate UV-LEDs of different peak wavelengths to cause synergistic effects to enhance the photoreaction efficiency.

The flow channels and UV-LED arrays of various reactor embodiments may be arranged in a way that the flow is exposed to the desired number of LEDs. The design may be a single flow channel, plurality of flow channels arranged serially or in parallel, or a stack of multiple flow channels. The total UV dose delivered to a fluid may be controlled by adjusting the flow rate and/or regulating UV-LED power, and/or turning on/off the number of UV-LEDs. This design enables the manufacture of thin planar UV-LED reactors. For example, in some embodiments the UV-LED reactor may be approximately the size of a felt-tip marker, in terms of geometry and dimensions, with inlet and outlet connection apertures for receiving a fluid from an external system and outputting treated fluid to an external system.

The internal wall of the channels may be made of or be coated with material with high UV reflectivity for facilitating radiation transfer to the fluid and for helping to achieve the dose uniformity described herein. Suitable reflective materials may include, by way of example, aluminum, Polytetrafluoroethylene (PTFE), quartz and/or the like. Two adjacent fluid flow channels may be connected at one end, for the fluid to go from one channel to another channel (fluid experiences multi-pass through the reactor).

In some embodiments portions of the reactor, where there is little or no radiation fluence rate may be blocked (e.g. filled) so that the fluid does not flow in these regions. This (effectively shaping the fluid flow channels) may help to prevent part of the fluid to receive low dose as a result of spending portions of its residence time in such regions.

FIGS. 13 to 18 and 20 illustrate views of an exemplary UV reactor 100, an exemplary UV reactor 200, and an exemplary UV reactor 300 according to other particular embodiments. Some embodiments of UV reactors 100, 200, and 300 may be similar to embodiments of UV reactors 10A, 10B, 10B', 10C, 70A, and/or 70B described above. For ease of description, some embodiments of reactors 100 and 200 may be described similarly to counterpart embodiments of any of reactors 10A, 10B, 10B', 10C, 70A, and 70B. Any combinations of these embodiments are part of this disclosure, making embodiments of reactors 100, 200, and/or 300 interchangeable with embodiments of reactors 10A, 10B, 10B', 10C, 70A, and/or 70B and vice versa.

Embodiments of UV reactor 100 are now described with reference to FIGS. 13 and 14. As shown, reactor 100 may comprise hydrodynamic and optical embodiments operable to deliver a dose of disinfecting radiation (e.g., UV radiation) to a fluid F moving through reactor 100. Numerous exemplary hydrodynamic and optical embodiments are described. In some embodiments, reactor 100 may comprise: a body 110; and an optical unit 170 mounted in body 110. For example, optical unit 170 may direct a disinfecting radiation into one or more flow channels in a first direction extending through body 110 and/or be cooled by fluid F when flowing in a second direction through said channels, in which the first direction may be antiparallel and/or opposite of the second direction. Numerous exemplary embodiments of body 110 and optical unit 170 are contemplated and now described.

Figure 13:
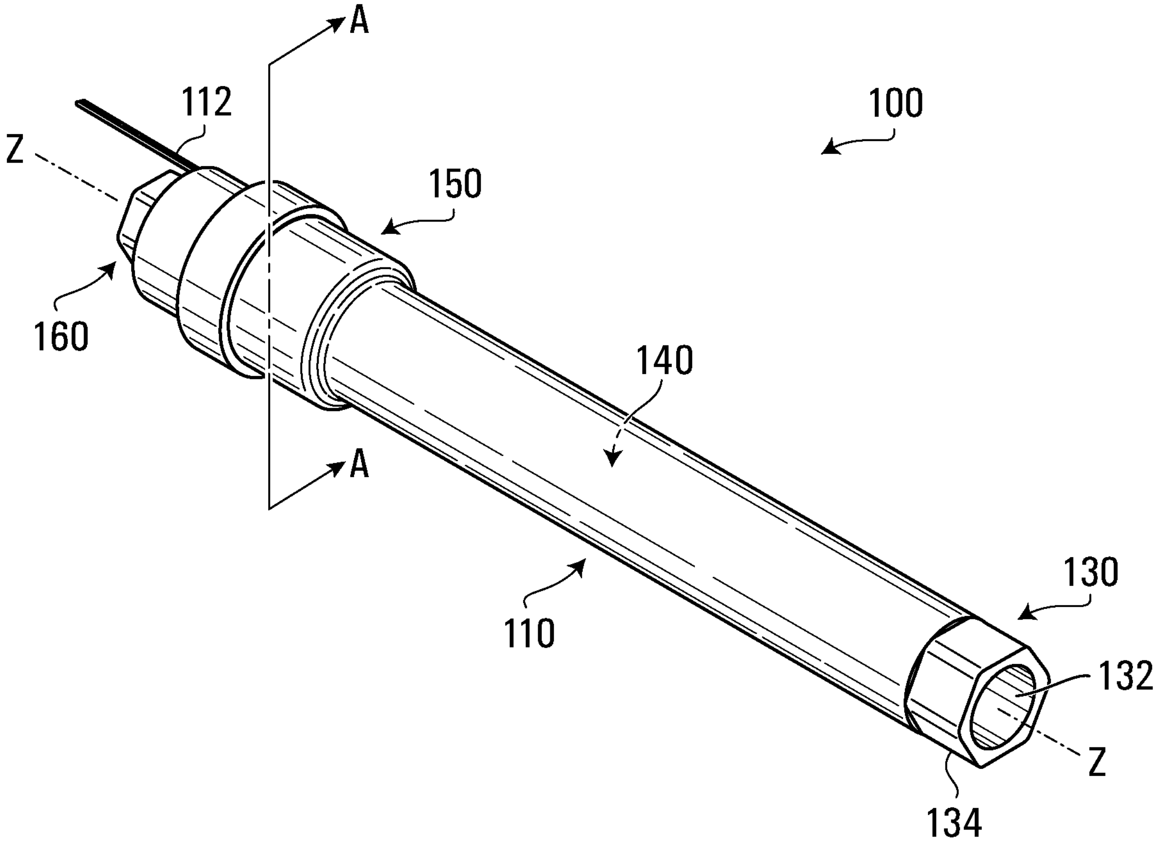
FIG. 13 shows an exemplary embodiment of a UV reactor.
Figure 14:
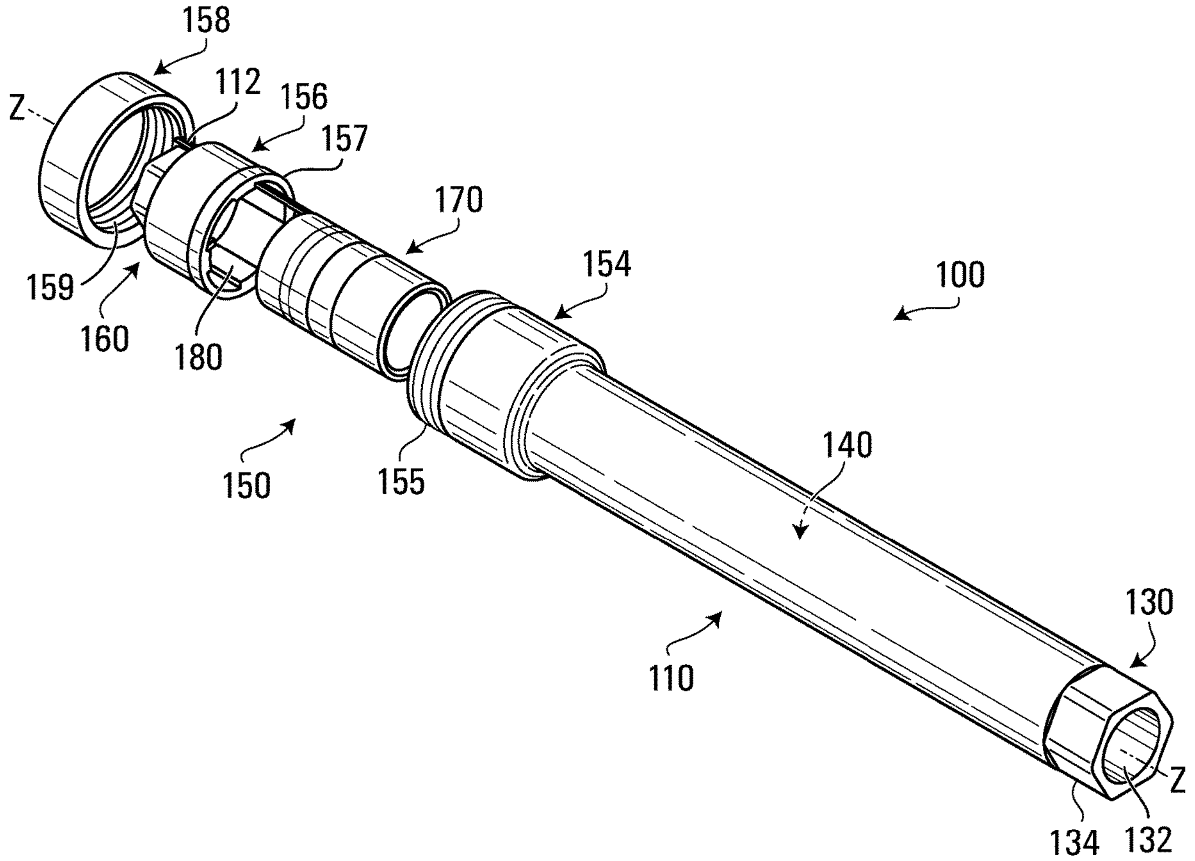
FIG. 14 shows an exploded view of the UV reactor of FIG. 13.

As shown in FIGS. 13 and 14, body 110 may comprise: an inlet 130; a flow channel 140; a socket 150; and an outlet 160. Examples of each element of body 110 are now described. Body 110 may include a plurality of connected portions, and all or at least some of the plurality of connected portions may be made of thermally or non-thermally conductive material. For example, each connected portion of body 110 may be made of a polymeric material that is UV and thermally resistant, including any known PVC materials. As shown in the exploded view of FIG. 14 and the cross-sectional view of FIG. 15, reactor 100 may be manufactured by assembling the plurality of connected portions together.

Inlet 130 may comprise: an opening 132 at one end of body 110; and an engagement structure 134 adjacent opening 132. As shown in FIGS. 13 and 14, opening 132 may extend into the one end of body 110 along the Z-axis to direct fluid F from a fluid input to flow channel 140. Opening 132 may be coaxial with flow channel 140 and/or an input flow channel of the fluid input. Engagement structure 134 may be configured to place opening 132 in communication with the input flow channel, allowing the fluid to flow into flow channel 140. For example, fluid F may be input to flow channel 140 from the input flow channel by engaging engagement structure 134 with a corresponding engagement structure of the fluid input. As shown in FIGS. 13 and 14, the fluid input may be the input pipe; and engagement structure 134 may be include a shape (e.g., a polygonal shape) that is receivable in a correspondingly shaped engagement structure of the input pipe (e.g., a corresponding polygonal shape).

Figure 15:
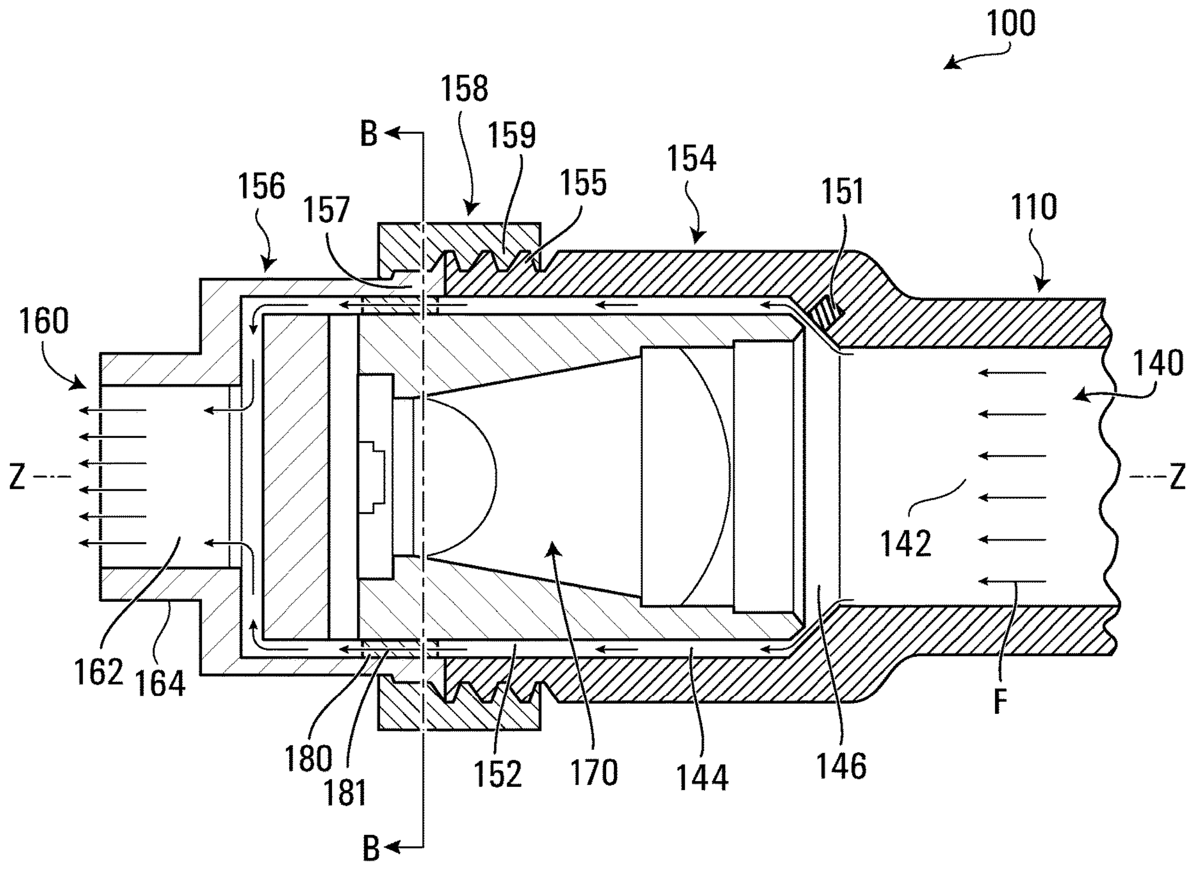
FIG. 15 shows a detailed cross-section of the UV reactor of FIG. 13 taken along the section line A-A shown in FIG. 13.

Flow channel 140 may include one or more portions that direct fluid F through body 110 along the Z-axis. As shown in FIG. 15, flow channel 140 may comprise a first portion 142 having a first cross-sectional area extending along the Z-axis between inlet 130 and socket 150; and a second portion 144 having a second cross-sectional area extending along the Z-axis between socket 150 and outlet 160. The first cross-sectional area of first portion 142 may be different from the second cross-sectional area of second portion 144 so as to define an interior cavity 152 and/or hydrodynamically modify fluid F moving through channel 140 in a direction along the Z-axis. In FIG. 15, for example, the first cross-sectional area of first portion 142 is circular, the second cross-sectional area of second portion 144 is annular, and channel 140 comprises a transition zone 146 extending therebetween. As shown, transition zone 146 may include a frustoconical shape, second portion 142 may include a cylindrical shape, and both shapes may be coaxial with the Z-axis. Any suitable circular or non-circular shapes also may be used.

The plurality of connected portions of body 110 may define interior cavity 152 and removably mount optical unit 170 in cavity 152. For example, as part of body 110, socket 150 also may include a plurality of connected portions that may be assembled together and taken apart. As shown in FIGS. 14 and 15, socket 150 may comprise: a first end portion 154; a second end portion 156; and a coupler 158. First and second end portions 154 and 156 may be engageable with coupler 158 to define interior cavity 152 within the second portion 144 of flow channel 140; and removably mount optical unit 170 in cavity 152. For example, first end portion 154 may include a first set of threads 155, second end portion 156 may include a second set of threads 157, and coupler 158 may include a third set of threads 159 engageable with first and second threads 155 and 157. Any configuration of threads may be used at any location. As shown in FIGS. 14 and 15, first set of threads 155 may be located on an exterior surface of first end portion 154; second of threads 157 may be located on an exterior surface of second end portion 156; and third set of threads 159 may be located on an interior surface of coupler 158 and engageable with threads 155 and 157 to assemble the plurality of connection portions of socket 150.

Figure 16:
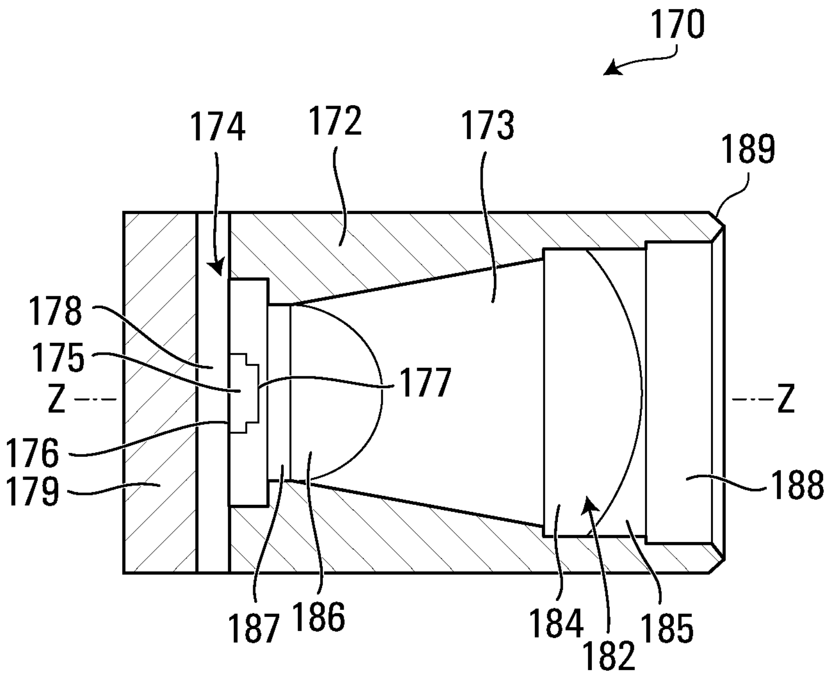
FIG. 16 shows a detailed cross-section of an exemplary optical unit.

Interior cavity 152 of socket 150 may comprise a mounting structure 180 configured to mount optical unit 170 by maintaining a position of unit 170 in cavity 152. As shown in FIGS. 14 and 16, mounting structure 180 may include a plurality of brackets 181 extending outwardly from interior surfaces of interior cavity 152 and toward the Z-axis to engage exterior surfaces of optical unit 170. Structure 180 may prevent optical unit 170 from moving laterally or axially along the Z-axis when fluid F is flowing through flow channel 140. For example, optical unit 170 may comprise an end face that is oriented perpendicularly to the Z-axis; fluid F may apply a movement force to unit 170 when flowing from first portion 142 of flow channel 140 into second portion 144 of channel 140; and mounting structure 180 may resist the movement forces.

One or more sensors 151 may be located in interior cavity 152 and configured to measure characteristics of fluid F and/or optical unit 170. For example, one or more sensors 151 may comprise a UV sensor; and the UV sensor may be positioned adjacent one end of optical unit 170 to measure an amount of the disinfecting radiation emitted by unit 170. Any type of sensor 151 may be used. For example, one or more sensors 151 may comprise any combination of: a contamination sensor; a disinfection level sensor; a fluid velocity sensor; a temperature sensor; and/or any other known measurement technologies. Sensors 121 may be electrically powered by any means, including any number of wires 112 extending through and/or are embedded within a portion socket 150.

As shown in FIG. 15, an end face of first end portion 154 may be butted against an end face of second end portion 156 so that first threads 155 are adjacent second threads 157 along the Z-axis, forming a row of threads. In this configuration, coupler 158 may be rotated relative to first end portion 154 and second end portion 156 of socket 150 so that third threads 159 may be engaged with the row of threads to define interior cavity 152, seal optical unit 170 and sensors 151 in cavity 152 and prevent fluid F from leaking out of cavity 152. For example, threads 159 may be engageable with threads 155 and 157 to apply maintaining forces in a direction along the Z-axis to form a seal between the respective end faces of portions 154 and 156. Adhesives, tapes, and/or other sealants may be used to reinforce the seal.

Much like inlet 130, outlet 160 may comprise: an opening 162 that is coaxial with flow channel 140 and/or an output flow channel of the fluid output. Engagement structure 164 may place outlet 160 in communication with the output flow channel. For example, fluid F may be output to the output flow channel from interior cavity 152 by engaging engagement structure 164 with a corresponding engagement structure of the fluid output. As shown in FIGS. 13 and 14, the fluid output may be a pipe; and engagement structure 164 may comprise a shape (e.g., a polygonal shape) that is receivable in a correspondingly shaped engagement structure of the pipe.

Figure 17:
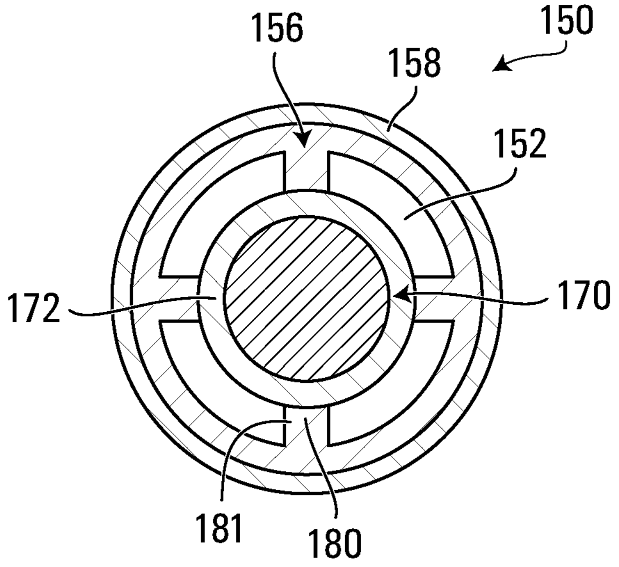
FIG. 17 shows a cross section of the UV reactor of FIG. 13 taken along the section line B-B shown in FIG. 15.

As shown in FIG. 16, optical unit 170 may comprise: a housing 172; an emitter assembly 174; a one or more lenses 182; and a UV transparent window 188. As shown in FIG. 16, optical unit 170 may be a standalone device that is removably mounted within interior cavity 152 of socket 150. For example, as shown in FIG. 17, one or more interior surfaces of cavity 152 may be attached to one or more exterior surfaces of housing 172, allowing optical unit 170 to be removed and/or replaced independently from reactor 100 by taking apart the plurality of connection portions of socket 150.

Housing 172 of optical unit 170 may comprise an interior chamber 173. As shown in FIG. 16, interior surfaces of interior chamber 173 may taper outwardly from the Z-axes between two or more of the plurality lenses 182. The interior surfaces of chamber 173 may maintain a spatial arrangement between two or more of the one or more lenses 182; and/or between at least one of the lenses 182 and emitter assembly 174. For example, one or more lenses 182 may comprise a first lens 184 spaced apart from a second lens 186; and the interior surfaces of chamber 173 may comprise a first mounting structure 185 for first lens 184 and a second mounting structure 187 for second lens 186. In this example, first mounting structure 185 may maintain a position of first lens 184 and second mounting structure 187 may maintain a position of second lens 186. The interior surfaces of chamber 173 also may direct the disinfecting radiation. For example, the interior surfaces of chamber 173 may comprise a frustoconical shape tapering outwardly from the Z-axis between first structure 185 and second structure 187 and/or a reflective surface or coating configured to direct the radiation from lens 184 to lens 186.

As shown in FIG. 16, emitter assembly 174 may comprise: an emitter 175; a printed circuit board or PCB 178; and a heat sink 179. Emitter 175 may comprise a solid-state UV emitter according to this disclosure, including any number of UV-LEDs according to any examples provided herein. In FIG. 16, emitter 175 comprises a heat-generating face 176 attached to PCB 178 and a radiation-emitting face 177 oriented toward one or more lenses 182. PCB 178 may seal one end of chamber 173. For example, as shown in FIG. 16, an end face of PCB 178 may be attached to one end of housing 172 by an adhesive or other attachment means for sealing chamber 173.

At least a portion PCB 178 may be thermally conductive. For example, PCB 178 may include a thermally conductive portion, and heat-generating face 176 of emitter 175 may be attached to the thermally conductive portion, providing a direct means of heat transfer between face 176 and PCB 178. As shown in FIG. 16, heat sink 179 may be made of a thermally conductive material (e.g., metal) that is thermally coupled to the thermally conductive portion of PCB 178. Heat sink 179 may define a thermally-conducting exterior surface of optical unit 170 that is configured for contact with fluid F, allowing emitter 175 to be thermally coupled with at least PCT 178, heat sink 179, and fluid F. In this configuration, mounting structure 180 may prevent heat transfer between heat sink 179 and body 110. As shown in FIG. 15, each bracket 181 of mounting structure 180 may made of non-thermally conductive material and extend between non-thermally conductive surfaces of interior cavity 152 and optical unit 170 so that heat sink 179 is thermally isolated from body 110 and yet surrounded by fluid F in cavity 152.

One or more lenses 182 may include different lenses spaced apart along the Z-axes to modify the disinfecting radiation. As shown in FIG. 16, first lens 184 may be a converging lens; and a second lens 186 may be a collimating lens. Converging lens 184 may be adjacent to the radiation-emitting face 176 of emitter 175 and positioned to receive and refract a radiation emitted therefrom. Collimating lens 186 may be spaced apart from converging lens and positioned to receive and further refract the radiation emitted from face 176. For example, collimating lens 186 may have a focal length f1 and may be positioned at a distance f', less than focal length f1, from a focal point of the radiation refracted by converging lens 184. In this example, a differential distance (Δ=f−f') between focal length f1 and distance f' of collimating lens 186 relative to the focal point of the radiation refracted by converging lens 184 may be in a range of 10%-35% of focal length f1.

As noted above, optical unit 170 may comprise an end face that is oriented perpendicularly to the Z-axis. UV transparent window 188 may define the end face. For example, window 188 may be made of any UV transparent material configured to resist the forces applied by fluid F when flowing through flow channel 140, including quartz and like materials. As shown in FIG. 16, UV transparent window 188 may define the end face of optical unit 170 and seal the other end of chamber 173. For example, window 188 may have a cylindrical shape and interior surfaces of chamber 173 may include a mounting structure configured to receive the cylindrical shape of window 188. The end face of unit 170 may be defined by a fluid-facing surface of window 188. As also shown in FIG. 16, for example, window 188 may be operable with an outer rim 189 of housing 172 to direct fluid F from transition zone 146 of flow channel 140 into second portion 144 of channel 140.

When reactor 100 is in operation, fluid F may flow: from the input source (e.g., a pipe attached to inlet 130); through opening 132 of inlet 30; and into the first portion 142 of flow channel 140 in a direction along the Z-axis, in which flow characteristics of fluid F at opening 132 may be similar to characteristics of fluid F in first portion 142. In first portion 142 of channel 140, fluid F may be exposed to a dosage of disinfecting radiation output from emitter 174 and one or more lenses 182. Fluid F may then flow: from first portion 142; through transition zone 146 of flow channel 140; and into second portion 144 of channel 140, which flow characteristics of fluid F at opening 132 may be different to characteristics of fluid F in second portion 144. As shown in FIG. 16, fluid F may be directed off the Z-axis and into second portion 144 by window 188 and/or rim 189 within transition zone 146.

Second portion 144 may direct fluid F around the exterior surfaces of optical unit 170. For example, the above-described second cross-sectional area of second portion 144 may be defined by interior surfaces of cavity 152 and exterior surfaces of optical unit 170 to direct fluid F around the heat conductive portions of optical unit 170, such as heat sink 179 and/or PCB 178. This configuration allows heat from emitter 175 to be transferred: from heat-conducting face 176; into the heat conductive portion of PCB 178; into heat sink 179; and finally, into fluid F, which may be flowing fast enough to dissipate the heat without also heating portions of body 110. Fluid F may then flow out of outlet 160 along the Z-axis and into the fluid output (e.g., a pipe attached to outlet 160).

Optical unit 170 may output the disinfecting radiation into flow channel 140 and/or onto any fluid F flowing through channel 140. For example, the radiation may be emitted by emitter 175 and modified further by one or more lenses 182 before passing into channel 140 through UV transparent window 189. When operating, heat from emitter assembly 174 may be discharged from: emitter 175; to the heat conductive portion of PCB 178; to heat sink 179; and then to fluid F. Accordingly, emitter 175 may be cooled during operation of reactor 100 by using the flow of fluid F as heat is carried away from optical unit 170 by the fluid F when flowing through outlet 160.

Additional embodiments are now described with reference to a UV reactor apparatus 200, shown conceptually in FIG. 18; and a UV reactor apparatus 300, shown conceptually in FIG. 20. Each variation of UV reactor apparatus 100, such as apparatus 200 and 300, may include elements similar to those of apparatus 100, but within the respective 200 or 300 series of numbers, whether or not those elements are shown.

Figure 18:
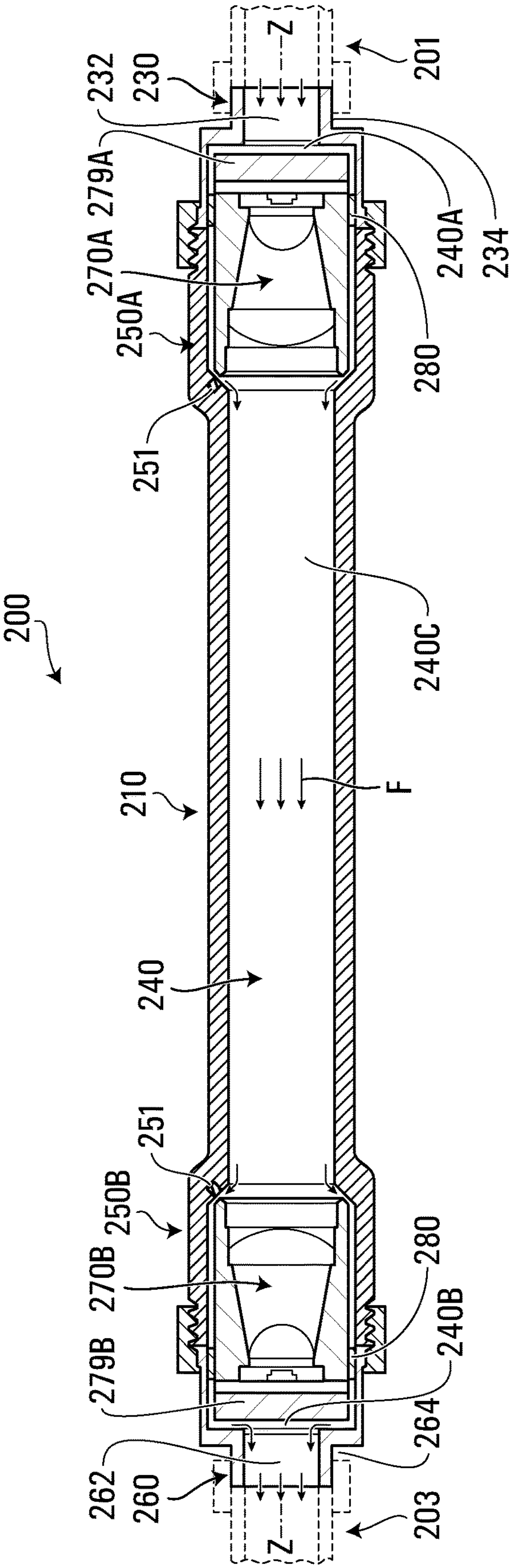
FIG. 18 shows an exemplary embodiment of another UV reactor.

As shown in FIG. 18, exemplary UV reactor apparatus 200 may comprise: a body 210; and a plurality of optical units 270 mounted in body 210. Similar to above, each optical unit 270 may direct a disinfecting radiation into one or more flow channels extending through body 210; and be cooled by fluid F when flowing through said channels. Numerous exemplary configurations of body 210 and optical unit 270 are contemplated.

As shown in FIG. 18, body 210 may comprise: an inlet 230; a flow channel 240; a first socket 250A; a second socket 250B; and outlet 260. Inlet 230 and outlet 260 of reactor 200 may be similar to inlet 130 and outlet 160 of reactor 100. For example, inlet 230 may similarly comprise an opening 232 extending into one end of body 210 along the Z-axis to direct fluid F from an input pipe 201 to flow channel 240, and an engagement structure 234 engageable with input pipe 201. And outlet 260 may similarly comprise an opening 262 extending the other end of body 210 along the Z-axis to direct fluid F into an output pipe 203, and an engagement structure 264 engageable with output pipe 203. As shown in FIG. 18, embodiments of reactor 200 may be installed in-line with input pipe 201 and outline pipe 203 and/or be arranged coaxially with the Z-axis.

Flow channel 240 may be similar flow channel 140. In some embodiments, flow channel 240 may likewise comprise a plurality portions configured to direct fluid F through body 110 along the Z-axis. As shown in FIG. 18, flow channel 240 may comprise: a first portion 240A having a first cross-sectional area extending along the Z-axis between inlet 230 and socket 250A; a second portion 240B having a second cross-sectional area extending along the Z-axis between socket 250B and outlet 260; and a third portion 240C having a third cross-sectional area extending along the Z-axis between socket 250A and socket 250B. According to this disclosure, the arrangement and dimensions of each portion 240A, 240B, and 240C of flow channel 240 may modify characteristics of fluid F when flowing through channel 240, including the residence time of fluid F in each portion 240A, 240B, and 240C.

Reactor 200 may comprise a plurality of optical units 270. As shown in FIG. 18, a first optical unit 270A may be removably mounted in first socket 250A; and a second optical unit 270B may be removably mounted in second socket 250B. Optical units 270A, 270B and sockets 250A, 250B of reactor 200 may be similar or even identical to each other as well as optical unit 170 and socket 150 of reactor 100. For example, socket 250A may be a mirror opposite of socket 250B and optical unit 270A may be identical to optical unit 270B, either being interchangeably mountable in one of sockets 250A or 250B, allowing fluid F to flow in either direction along the Z-axis.

In operation, fluid F may be directed: into opening 232 of inlet 230 from input pipe 201; around first optical unit 270A in first portion 240A of flow channel 240, cooling unit 270A with fluid F according to any embodiment described herein; into third portion 240C of channel 240, exposing fluid F to disinfecting radiation from one or both of optical units 270A and 270B; around second optical unit 250B in second portion 240B of channel 240, cooling unit 270B with fluid F according to any embodiment described herein; and into opening 262 of outlet 260 for delivery to output pipe 203. For example, the disinfecting radiation may be simultaneously emitted by both first and second optical units 270A and 270B into portion 240C of channel 240 in opposing directions along the Z-axis.

As shown in FIG. 18, heat from optical units 270A and 270B may be transferred to fluid F via a heat sink 279A or 279B attached thereto. Heat sinks 279A and 279B may be thermally isolated from body 210. For example, as above, optical units 270A and 270B may be mounted in their respective portions 240A and 240B of flow channel 240 by mounting structures 280 extending between non-thermally conducting portions of body 210 and optical units 270A and 270B, preventing heat transfer to body 210. If addition cooling is required, then body 210 may be used as an additional heat sink. For example, the mounting structures 280 may be thermally conductive and extend between thermally-conductive portions of body 210 and units 270A and 270B, permitting heat transfer to body 210.

As also shown in FIG. 18, one or more sensors 251 may be located each portion 240A and 240B of flow channel 240 and configured to measure characteristics of fluid F and/or optical unit 170. For example, one or more sensors 251 may similarly comprise a UV sensor; and the UV sensor may be positioned adjacent one end of optical unit 170 to measure an amount of the disinfecting radiation emitted by unit 270A and/or 270B. Any type of sensor 251 may be used and powered by any means. For reactor 200, the respective sensors 251 in each of portions 240A and 240B may measure the disinfecting radiation from one or both of optical units 270A and 270B and be operable with one or more processors to responsively modify a performance of unit 270A or 270B.

Figure 20:
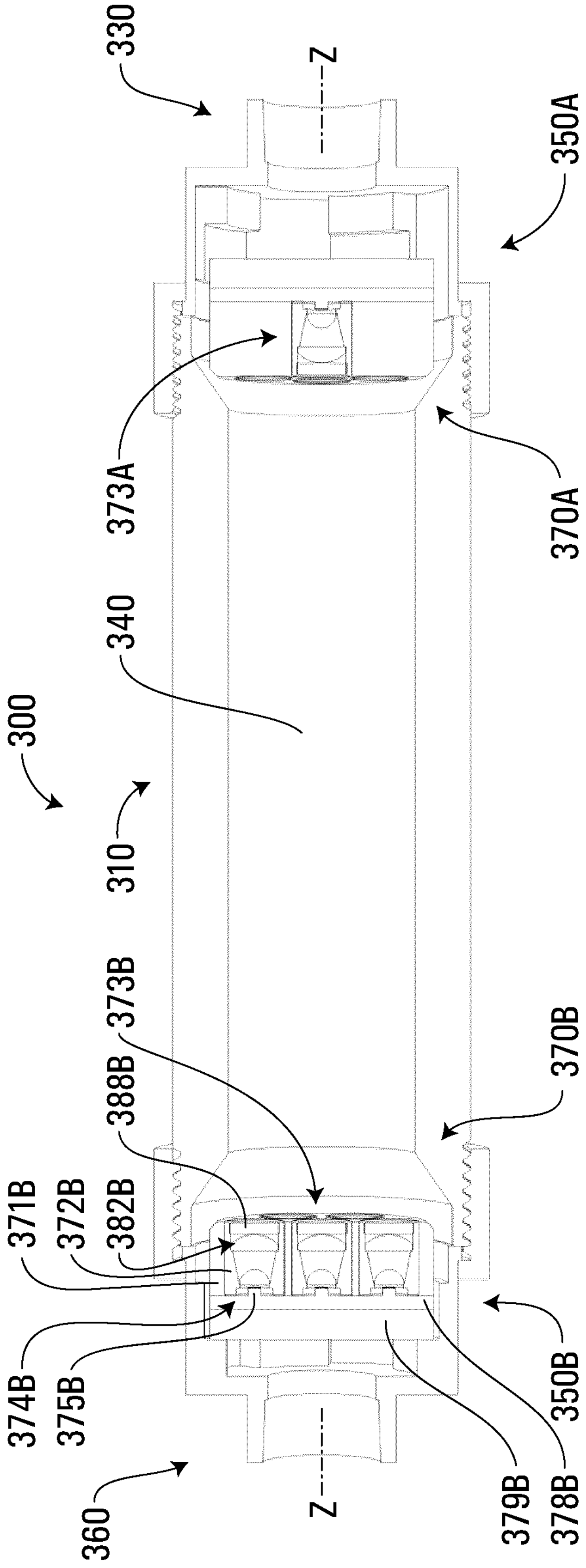
FIG. 20 shows another exemplary embodiment of a UV reactor.

As shown in FIG. 20, exemplary UV reactor apparatus 300 may comprise: a body 310; and a plurality of optical units 370 mounted in body 310. Similar to above, each optical unit 370 may direct a disinfecting radiation into one or more flow channels extending through body 310; and be cooled by fluid F when flowing through said channels. Numerous exemplary configurations of body 310 and optical unit 370 are contemplated.

As shown in FIG. 20, body 310 may comprise: an inlet 330; a flow channel 340; a first socket 350A; a second socket 350B; and outlet 360. Inlet 330, flow channel 340, and outlet 360 of reactor 300 may be similar to inlet 230, flow channel 240, and outlet 260 of reactor 200. For example, flow channel 340 may likewise comprise a plurality portions configured to direct fluid F through body 110 along the Z-axis.

Reactor 300 may comprise a plurality of optical units, and each optical unit may comprise at least one radiation source. As shown in FIG. 20, a first optical unit 370A may be removably mounted in first socket 350A; and a second optical unit 370B may be removably mounted in second socket 350B. Optical units 370A, 370B and sockets 350A, 350B of reactor 300 may be different or similar. For example, socket 350A may be a mirror opposite of socket 350B and optical unit 370A may be different from optical unit 370B, either being interchangeably mountable in one of sockets 350A or 350B, allowing fluid F to flow in either direction along the Z-axis.

First optical unit 370A may comprise at least one solid-state radiation source 373A, similar to optical unit 170. In contrast, second optical unit 370B may comprise a frame 371B containing a plurality of solid-state radiation sources 373B. As shown in FIG. 20 with reference to one of sources 373B, each source 373B may comprise: a housing 372B; an emitter assembly 374B; a one or more lenses 382B; and a UV transparent window 388B. Frame 371B may be assembled together or formed integral with each housing 372B. For example, each source 373B may be a stand-alone device similar to that of FIG. 16. Each emitter assembly 374B may be mounted to a thermally conductive portion of reactor 300. For example, similar to above, each emitter assembly 374B of FIG. 20 may comprise an emitter 375B mounted to a thermally conductive portion of a common PCB 378B, which may in turn be attached to heat sink 379B similar to heat sink 179 of reactor 100. As a further example, each emitter 375B may be operable with its own set of lenses 382B and window 388B according to this disclosure. Alternatively still, each emitter 375B may comprise an individual PCB board 378B attached to common heat sink 379.

Figure 19:
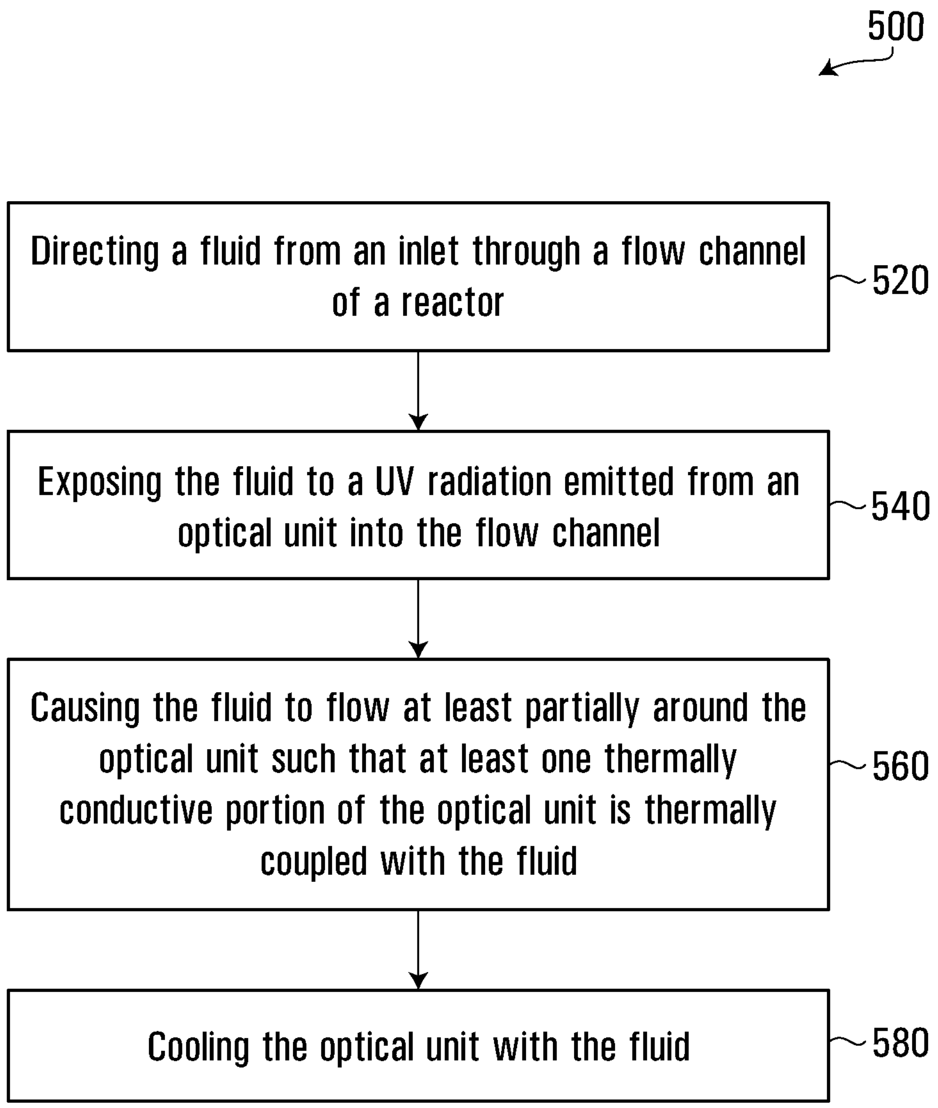
FIG. 19 shows an exemplary disinfection method.

Additional embodiments are now described with reference to an exemplary disinfection method 500. For ease of description, embodiments of method 500 are described with reference to UV reactor apparatus 100, though similar embodiments may likewise be described with reference to any apparatus described herein. As shown in FIG. 19, method 500 may comprise: directing fluid F from inlet 130 through flow channel 140 reactor 100 (a "directing step 520"); exposing fluid F to UV radiation emitted from optical unit 170 into flow channel 140, optical unit 170 being mounted in cavity 152 of flow channel 140 and including: a solid-state radiation source for emitting UV radiation, and at least one thermally conductive portion thermally coupled to the solid-state radiation source (an "exposing step" 540); causing fluid F to flow at least partially around optical unit 170 to outlet 160 so that the at least one thermally conductive portion of optical unit 170 is thermally coupled with fluid F (a "diverting step" 560); and cooling optical unit 170 with fluid F (a "cooling step" 580). Exemplary embodiments of steps 520, 540, 560 and 580 are now described.

Directing step 520 may comprise intermediate steps for receiving and/or directing fluid F. As described above, the arrangement and dimensions of each portion of flow channel 140, the position of optical unit 140 in cavity 152, and the shape of mounting structure 180 and/or brackets 181 may be configured individually or together to modify fluid F during step 520. Accordingly, step 520 may further comprise causing fluid F to flow with a velocity that is positively correlated with an intensity of UV radiation emitted from the optical unit 170.

Exposing step 540 may comprise intermediate steps for exposing fluid F to the dosage of the disinfecting radiation. For example, the solid-state radiation source may comprise a solid-state UV emitter (e.g., emitter 175), and step 540 may comprise causing the solid-state UV emitter to emit UV radiation. Step 540 also may comprise outputting radiation through one or more of the one or more lenses 182, such as converging lens 184 and/or collimating lens 186. For example, step 540 may comprise refracting the emitted UV radiation with the one or more lenses 182. As a further example, exposing step 540 also may comprise outputting UV radiation through UV transparent window 188 and/or matching an intensity of the radiation at a location in the flow channel 140 with a velocity of the fluid F at the location channel 140. For example, one or more lenses 182 may be configured to match the intensity with the velocity in channel 140.

Diverting step 560 may comprise intermediate steps for causing fluid F to flow around optical unit 170 and/or out of outlet 160. For example, step 560 may comprise mounting optical unit 170 in cavity 152 and/or modifying characteristics of fluid F when flowing through portions of channel 140, such as velocity or temperature.

Cooling step 580 may comprise intermediate steps for removing heat from optical unit 170. For example, step 580 may comprise transferring heat from optical unit 170 to fluid F through the thermally conductive portion of optical unit 170. In some embodiments, step 580 may comprise transferring a portion of the heat from optical unit 170 to body 110 through a thermally conducting mounting structure (e.g., similar to structure 180) extending between the thermally conductive portion of optical unit 170 and a thermally conductive portion of body 110.

Method 500 also may comprise additional steps. For example, optical unit 170 may be removably mounting in cavity 152, and method 500 may further comprise: causing the fluid F to flow at least partially around the mounted unit 170; removing and replacing unit 170 from cavity 152; and related intermediate steps.

According to the embodiments described herein, fluid F may be disinfected using any combination of apparatus 10A, 10B, 10B', 10C, 70A, 70B, 100, 200, or 300; and any iteration of method 500 appropriate thereto. Some embodiments have been described with reference to particular radiation sources and fluids. For example, the radiation source may include a solid-state radiation source such as a UV-LED and the fluid may include water. As noted above, these examples are provided for convenience and not intended to limit the present disclosure. For example, the radiation source may alternatively comprise any alternative source of UV radiation, such as a fiber optical cable comprising a UV transparent material configured to transmit the UV radiation from a source, such as UV laser generator. Similar modifications may be made for any type of fluid. For example, the disinfecting radiation may comprise any combination of UV and/or non-UV radiation appropriate for use with a particular fluid, or to remove a particular contaminant.

A number of additional apparatus and method embodiments are now described. In some embodiments, there is provided an ultraviolet (UV) reactor for irradiating a flow of fluid with UV radiation. The reactor may comprise: a fluid conduit defined at least in part by an outer conduit-defining wall for permitting a fluid flow therethrough; a solid-state UV emitter (e.g. ultraviolet light emitting diode or UV-LED); and a radiation-focusing element comprising one or more lenses; wherein the fluid conduit comprises a fluid inlet, a fluid outlet and a longitudinally extending fluid flow channel located between the inlet and the outlet, the fluid flow channel extending in a longitudinal direction for permitting the fluid flow in a longitudinal direction through a bore of the fluid flow channel and the fluid flow channel having a central channel axis that extends in the longitudinal direction through centroids of transverse cross-sections of the bore in at least a longitudinally central portion of the bore; wherein the one or more lenses are positioned in a radiation path of radiation emitted from the solid-state UV emitter for directing radiation from the solid-state UV emitter to impinge on the fluid flowing in the fluid flow channel and to thereby provide a radiation fluence rate profile within a bore of the fluid flow channel; and wherein the one or more lenses may be configured to provide the radiation fluence rate profile wherein: for cross-sections of the bore of the fluid flow channel located relatively close to the solid-state UV emitter (e.g. for a first cross-section), the radiation fluence rate profile may be relatively high at locations that are relatively far from the central channel axis and relatively low at locations nearer to the central channel axis; and for cross-sections of the bore of the fluid flow channel located relatively distal from the solid-state UV emitter (e.g. for a second cross-section located more distal from the solid-state UV emitter than the first cross-section), the radiation fluence rate profile may be relatively low at locations that are relatively far from the central channel axis and relatively high at locations nearer to the central channel axis.

In some embodiments, there is provided a UV reactor wherein the one or more lenses may be configured to provide the radiation fluence profile by one or more of: selection of the one or more lenses from among a variety of lens types, shape of the one or more lenses, position of the one or more lenses and indices of refraction of the one or more lenses.

In some embodiments, there is provided a UV reactor wherein the one or more lenses may comprise a converging lens located to receive radiation from the UV emitter and a collimating lens located to receive radiation emitted from the converging lens and wherein the collimating lens is positioned at a distance f', which is less than its focal length f1 from a focal point of radiation emitted from the converging lens.

In some embodiments, there is provided a UV reactor wherein a differential distance (Δ=f−f') between the position f' of the collimating lens relative to the focal point and the focal length f1 of the collimating lens relative to the focal point may be in a range of 10%-35% of the focal length f1.

In some embodiments, there is provided a UV reactor wherein the one or more lenses may comprise a half-ball lens positioned to receive radiation from the UV emitter and a plano-convex lens positioned to receive radiation from the half-ball lens, with both the half-ball lens and plano-convex lens having their planar sides facing the UV emitter and with the solid state UV emitter, the half-ball lens and the plano-convex lens having their optical axes co-axial with the central channel axis.

The UV reactor may comprise an air space on a side of the plano-convex lens that is opposite from a side of the solid-state UV emitter and a UV transparent window separating the air space from the fluid flow in the fluid flow channel.

In some embodiments, there is provided a UV reactor wherein the plano-convex lens may be positioned at a distance f', which is less than its inherent focal length f1, from a focal point of radiation emitted from the half-ball lens.

In some embodiments, there is provided a UV reactor wherein a spacing f' of the plano-convex lens relative to the focal point of the half-ball lens may be less than the inherent focal length f1 of the plano-convex lens by a differential distance Δ and the differential distance Δ is in a range of 10%-35% of the focal length f1 of the plano-convex lens.

In some embodiments, there is provided a UV reactor wherein the one or more lenses may comprise a first lens positioned relatively close to the UV emitter to receive radiation from the UV emitter and a second lens positioned relatively far from the UV emitter to receive radiation from the first lens, with the solid state UV emitter, the first lens and the second lens having their optical axes co-axial with the central channel axis.

In some embodiments, the second lens may be positioned at a distance f', which is less than its inherent focal length f1, from a focal point of radiation emitted from the first lens.

In some embodiments, there is provided a UV reactor wherein a spacing f' of the second lens relative to the focal point of the first lens may be less than the inherent focal length f1 of the second lens by a differential distance Δ and the differential distance Δ is in a range of 10%-35% of the focal length f1 of the second lens.

In some embodiments, there is provided a UV reactor wherein the bore of the fluid flow channel may have circularly shaped cross-sections in at least the longitudinally central portion thereof and wherein the principal optical axis of the solid-state UV emitter, the optical axes of the one or more lenses and the central channel axis are co-linear.

In some embodiments, there is provided a UV reactor wherein: the fluid inlet may comprise: one or more inlet apertures, where the fluid inlet opens into the bore of the fluid flow channel; one or more connecting apertures, through which the UV reactor is connectable an external fluid system for providing fluid to the reactor; and one or more inlet conduits which extend between the one or more inlet apertures and the one or more connecting apertures; and the fluid outlet may comprise: one or more outlet apertures, where the fluid outlet opens into the bore of the fluid flow channel, one or more connecting apertures, through which the UV reactor is connectable to an external output fluid system to which fluid flows from the reactor; and one or more outlet conduits which extend between the one or more outlet apertures and the one or more connecting apertures.

In some embodiments, the UV reactor may comprise a housing for supporting the solid-state UV emitter and the radiation focusing element such that the principal optical axis of the solid-state UV emitter is at least generally aligned with the central channel axis, the housing comprising a UV-transparent window for separating the solid-state UV emitter and the radiation focusing element from the fluid flow in the fluid flow channel. In some embodiments, there is provided a UV reactor wherein: the solid-state UV emitter may be located relatively proximate to the fluid outlet and relatively distal from the fluid inlet, with the principal optical axis of the solid state emitter oriented generally antiparallel to the longitudinal fluid flow direction; and the fluid conduit may comprise a cross-sectional wall at one end thereof, the cross-sectional wall defining the one or more inlet apertures for the fluid inlet, the one or more inlet apertures centrally located in the cross-sectional wall such that the central channel axis passes through a center of the one or more inlet apertures.

In some embodiments, there is provided a UV reactor wherein: the solid-state UV emitter may be located relatively proximate to the fluid outlet and relatively distal from the fluid inlet, with the principal optical axis of the solid state emitter oriented generally antiparallel to the longitudinal fluid flow direction; and the fluid conduit may comprise a cross-sectional wall at one end thereof, the cross-sectional wall supporting the fluid inlet, the one or more inlet apertures of the fluid inlet centrally located in a cross-section of the bore such that the central channel axis passes through a center of the one or more inlet apertures.

In some embodiments, the one or more inlet apertures may be centrally located in the cross-sectional wall such that the central channel axis passes through a center of the one or more inlet apertures. For example, the one or more inlet apertures may be centrally located in the cross-sectional wall such that the one or more inlet apertures are circularly symmetric about a point that is located on the central channel axis.

In some embodiments, there is provided a UV reactor wherein an outlet aperture of the fluid outlet may be defined by a combination of the outer conduit-defining wall and the housing such that the outlet aperture is located at a location spaced transversely apart from the central channel axis. For example, the fluid outlet may be supported by a combination of the outer conduit-defining wall and the housing, such that an outlet aperture of the fluid outlet is located at a location spaced transversely apart from the central channel axis.

In some embodiments, the outlet aperture of the fluid outlet may be located as far away from the central channel axis as is permitted by the bore of the fluid flow channel; the housing may be supported by one or more brackets that extend from the outer conduit-defining wall of the fluid conduit to the housing; and/or the one or more brackets may extend across the outlet conduit of the fluid outlet. In some embodiments, the outlet conduit of the fluid outlet may have generally annular cross-sections at locations between the outlet aperture and the one or more connecting apertures wherein these cross-sections are defined by the outer conduit-defining wall and the housing.

In some embodiments, there is provided a UV reactor wherein: for cross-sections of the bore of the fluid flow channel located relatively close to the one or more inlet apertures, the fluid velocity may be relatively low at locations that are relatively far from the central channel axis and relatively high at locations relatively close to the central channel axis; and for cross-sections of the bore of the fluid flow channel located relatively close to the outlet aperture, the fluid velocity may be relatively high at some locations relatively far from the central channel axis and relatively low at locations relatively close to the central channel axis. For example, the at least some locations relatively far from the central channel axis may comprise locations directly upstream from or adjacent to the outlet aperture.

In some embodiments, there is provided a UV reactor wherein the fluid outlet conduit of the fluid outlet may be defined in part by, or is otherwise in thermal contact with, the housing and wherein the housing, in turn, is in direct or indirect (e.g. via a printed circuit board on which the solid-state UV emitter is mounted) thermal contact with the solid-state UV emitter for removing heat from the solid-state UV emitter and transferring such heat to the fluid. For example, a printed circuit board (PCB) on which the UV emitter is mounted may provide at least a portion of a wall of the housing or the outlet conduit so that the fluid is in thermal contact with the PCB on which the UV emitter is mounted.

In some embodiments, there is provided a UV reactor wherein: the solid-state UV emitter may be located relatively proximate to the fluid inlet and relatively distal from the fluid outlet, with the principal optical axis of the solid-state UV emitter oriented generally parallel to and in the same direction as the longitudinal flow direction; and the fluid conduit may comprise a cross-sectional wall at one end thereof, the cross-sectional wall defining the one or more outlet apertures for the fluid outlet, the one or more outlet apertures centrally located in the cross-sectional wall such that the central channel axis passes through a center of the one or more outlet apertures.

In some embodiments, there is provided a UV reactor wherein: the solid-state UV emitter may be located relatively proximate to the fluid inlet and relatively distal from the fluid outlet, with the principal optical axis of the solid-state UV emitter oriented generally parallel to and in the same direction as the longitudinal flow direction; and the fluid conduit may comprise a cross-sectional wall at one end thereof, the cross-sectional wall supporting the fluid outlet, the one or more outlet apertures of the fluid outlet centrally located in a cross-section of the bore such that the central channel axis passes through a center of the one or more outlet apertures. For example, the one or more outlet apertures may be centrally located in the cross-sectional wall such that the central channel axis passes through a center of the one or more outlet apertures.

As further examples, the one or more outlet apertures may be centrally located in the cross-sectional wall such that the one or more outlet apertures are circularly symmetric about a point that is located on the central channel axis; an inlet aperture of the fluid inlet may be defined by a combination of the outer conduit-defining wall and the housing such that the inlet aperture is located at a location spaced transversely apart from the central channel axis; the fluid inlet may be supported by a combination of the outer conduit-defining wall and the housing, such that an inlet aperture of the fluid inlet is located at a location spaced transversely apart from the central channel axis; the inlet aperture of the fluid inlet may be located as far away from the central channel axis as is permitted by the bore of the fluid flow channel; the housing may be supported by one or more brackets that extend from the outer conduit-defining wall of the fluid conduit to the housing; and/or the one or more brackets may extend across the inlet conduit of the fluid outlet.

In some embodiments, the inlet conduit of the fluid inlet may have generally annular cross-sections at locations between the inlet aperture and the one or more connecting apertures wherein these cross-sections are defined by the outer conduit-defining wall and the housing. In some embodiments, there is provided a UV reactor wherein: for cross-sections of the bore of the fluid flow channel located relatively close to the one or more outlet apertures, the fluid velocity may be relatively low at locations that are relatively far from the central channel axis and relatively high at locations relatively close to the central channel axis; and for cross-sections of the bore of the fluid flow channel located relatively close to the inlet aperture, the fluid velocity may be relatively high at some locations relatively far from the central channel axis and relatively low at locations relatively close to the central channel axis.

In some embodiments, at least some locations relatively far from the central channel axis may comprise locations directly downstream from or adjacent to the inlet aperture. For example, the fluid inlet conduit of the fluid inlet may be defined in part by or is otherwise in direct or indirect (e.g. via a printed circuit board on which the solid-state UV emitter is mounted) thermal contact with, the housing and wherein the housing, in turn, is in thermal contact with the solid-state UV emitter for removing heat from the solid-state UV emitter and transferring such heat to the fluid.

In some embodiments, there is provided a UV reactor wherein a printed circuit board (PCB) on which the UV emitter is mounted may provide at least a portion of a wall of the housing or the inlet conduit so that the fluid is in thermal contact with the PCB on which the UV emitter is mounted. In some embodiments, there is provided a UV reactor which may comprise one or more flow modifiers located in the fluid flow channel, the one or more flow modifiers shaped and/or located for altering local velocity characteristics of the fluid flow in regions of the fluid flow channel adjacent the one or more flow modifiers. For example, the one or more flow modifiers may comprise: a ring or baffle that extends from the bore defining wall of the fluid flow channel; a ring or baffle located directly downstream from an inlet aperture; a ring or baffle located in an outlet conduit of the fluid outlet; and/or a ring or baffle located in an inlet conduit of the fluid inlet. In some embodiments, the one or more flow modifiers may comprise one or more of a delta wing shaped mixer and a twisted tape shaped mixer to create vortices in the fluid flow.

In some embodiments, there is provided a UV reactor which may comprise: a second solid-state UV emitter having a secondary principal optical axis that is oriented anti-parallel to the principal optical axis of the solid-state UV emitter; and a second radiation-focusing element comprising one or more secondary lenses positioned in a second radiation path of radiation emitted from the second solid-state UV emitter for directing radiation from the second solid-state UV emitter to impinge on the fluid flowing in the fluid flow channel and to thereby provide a second radiation fluence rate profile within the bore of the fluid flow channel; wherein the one or more secondary lenses are configured to provide the radiation fluence rate profile wherein: for secondary cross-sections of the bore of the fluid flow channel located relatively close to the second solid-state UV emitter, the second radiation fluence rate profile is relatively high at locations that are relatively far from the central channel axis and relatively low at locations nearer to the central channel axis; and for secondary cross-sections of the bore of the fluid flow channel located relatively distal from the second solid-state UV emitter, the second radiation fluence rate profile is relatively low at locations that are relatively far from the central channel axis and relatively high at locations that are nearer to the central channel axis. For example, the principal optical axis of the solid-state UV emitter, the principal optical axis of the second solid-state UV emitter, the optical axes of the one or more lenses, the optical axes of the one or more secondary lenses and the central channel axis may be co-axial.

In some embodiments, there is provided a method for using an ultraviolet (UV) reactor for irradiating a fluid travelling through the reactor with UV radiation to thereby treat the fluid. The method may comprise: providing a UV reactor comprising a fluid conduit defined at least in part by an outer conduit-defining wall for permitting a fluid flow therethrough, a solid-state UV emitter (e.g. ultraviolet light emitting diode or UV-LED), and a radiation-focusing element comprising one or more lenses; introducing the fluid into a bore of a longitudinally extending fluid flow channel via a fluid inlet, allowing the fluid to flow through the longitudinally extending fluid flow channel in a longitudinal direction and removing the fluid from the fluid flow channel via a fluid outlet, the fluid outlet located at a longitudinally opposite end of the fluid flow channel from the inlet, wherein the fluid flow channel has a central channel axis that extends in the longitudinal direction through centroids of transverse cross-sections of the bore in at least a longitudinally central portion of the bore; directing radiation from the solid-state UV emitter through the one or more lenses and thereby causing the radiation to impinge on the fluid flowing in the fluid flow channel and to thereby provide a radiation fluence rate profile within the bore of the fluid flow channel; wherein the one or more lenses may be configured to provide the radiation fluence rate profile wherein: for cross-sections of the bore of the fluid flow channel located relatively close to the solid-state UV emitter (e.g. for a first cross-section), the radiation fluence rate profile is relatively high at locations that are relatively far from the central channel axis and relatively low at locations that are relatively close to the central channel axis; and for cross-sections of the bore of the fluid flow channel located relatively distal from the solid-state UV emitter (e.g. for a second cross-section located more distal from the solid-state UV emitter than the first cross-section), the radiation fluence rate profile is relatively low at locations that are relatively far from the central channel axis and relatively high at locations that are nearer to the central channel axis.

In some embodiments, there is provided an ultraviolet (UV) reactor for irradiating a flow of fluid with UV radiation. The UV reactor may comprise: a fluid conduit defined at least in part by an outer conduit-defining wall for permitting a fluid flow therethrough; a first solid-state UV emitter (e.g. ultraviolet light emitting diode or UV-LED); a first radiation-focusing element comprising one or more first lenses; a second solid-state UV emitter;

and a second radiation-focusing element comprising one or more second lenses; wherein the fluid conduit comprises a fluid inlet, a fluid outlet and a longitudinally extending fluid flow channel located between the inlet and the outlet, the fluid flow channel extending in a longitudinal direction for permitting the fluid flow in a longitudinal direction through a bore of the fluid flow channel and the fluid flow channel having a central channel axis that extends in the longitudinal direction through centroids of transverse cross-sections of the bore in at least a longitudinally central portion of the bore; wherein the one or more first lenses are positioned in a radiation path of first radiation emitted from the first solid-state UV emitter for directing the first radiation from the first solid-state UV emitter to impinge on the fluid flowing in the fluid flow channel from an outlet end of the fluid flow channel in a direction generally opposed to the longitudinal direction of fluid flow; wherein the one or more second lenses are positioned in a radiation path of second radiation emitted from the second solid-state UV emitter for directing the second radiation from the second solid-state UV emitter to impinge on the fluid flowing in the fluid flow channel from an inlet end of the fluid flow channel in a direction generally aligned with and in the same direction as the longitudinal direction of fluid flow; a first housing for supporting the first solid-state UV emitter such that a principal optical axis of the first solid-state UV emitter is at least generally co-axial with the central channel axis and wherein an outlet aperture for the fluid outlet, where the fluid outlet opens into the bore of the fluid flow channel, is defined by a combination of the outer conduit-defining wall and the first housing; and a second housing for supporting the second solid-state UV emitter such that a principal optical axis of the second solid-state UV emitter is at least generally co-axial with the central channel axis and wherein an inlet aperture for the fluid inlet, where the fluid inlet opens into the bore of the fluid flow channel, is defined by a combination of the outer conduit-defining wall and the second housing. For example, the cross-sections of the outlet conduit of the fluid outlet and the inlet conduit of the fluid inlet may be annularly shaped.

In some embodiments, the inlet aperture of the fluid inlet and the outlet aperture of the fluid outlet may be located toward a transverse cross-section edge of the fluid conduit and: for cross-sections of the bore of the fluid flow channel located relatively close to the fluid inlet and relatively close to the fluid outlet, the fluid velocity may be relatively high at some locations that are relatively far from the central channel axis (e.g. at locations directly upstream from or adjacent to the outlet aperture and at locations directly downstream from or adjacent to the inlet aperture) and relatively low at locations relatively close to the central channel axis; and for longitudinally central cross-sections of the bore of the fluid flow channel, the fluid velocity may be relatively low at locations relatively far from the central channel axis and relatively high at locations relatively close to the central channel axis.

In some embodiments, the one or more first lenses, the one or more second lenses and a longitudinal dimension of the fluid flow channel may be configured such that: for cross-sections of the bore of the fluid flow channel located relatively close to the first UV emitter and for cross-sections of the bore of the fluid flow channel located relatively close to the second UV emitter, the radiation fluence rate profile may be relatively high at locations relatively far from the central channel axis and relatively low at locations nearer to the central channel axis; and for longitudinally central cross-sections of the bore of the fluid flow channel, the radiation fluence rate profile may be relatively low at locations relatively far from the central channel axis and relatively high at locations nearer to the central channel axis.

In some embodiments, there is provided a method for using an ultraviolet (UV) reactor for irradiating a fluid travelling through the reactor with UV radiation to thereby treat the fluid. The method may comprise: providing a UV reactor comprising a fluid conduit defined at least in part by an outer conduit-defining wall for permitting a fluid flow therethrough; a first solid-state UV emitter (e.g. ultraviolet light emitting diode or UV-LED); a first radiation-focusing element comprising one or more first lenses; a second solid-state UV emitter; and a second radiation-focusing element comprising one or more second lenses; introducing the fluid into a bore of a longitudinally extending fluid flow channel via a fluid inlet, allowing the fluid to flow through the longitudinally extending fluid flow channel in a longitudinal direction and removing the fluid from the fluid flow channel via a fluid outlet, the fluid outlet located at a longitudinally opposite end of the fluid flow channel from the inlet, wherein the fluid flow channel has a central channel axis that extends in the longitudinal direction through centroids of transverse cross-sections of the bore in at least a longitudinally central portion of the bore; directing first radiation from the first solid-state UV emitter through the one or more first lenses and thereby causing the first radiation to impinge on the fluid flowing in the fluid flow channel from an outlet end of the fluid flow channel in a direction generally opposed to the longitudinal direction of fluid flow; directing second radiation from the second solid-state UV emitter through the one or more secondary lenses and thereby causing the second radiation to impinge on the fluid flowing in the fluid flow channel from an inlet end of the fluid flow channel in a direction generally aligned with and in the same direction as the longitudinal direction of fluid flow; supporting the first solid-state UV emitter in a first housing such that a principal optical axis of the first solid-state UV emitter is at least generally co-axial with the central channel axis and wherein an outlet aperture for the fluid outlet, where the fluid outlet opens into the bore of the fluid flow channel, is defined by a combination of the outer conduit-defining wall and the first housing; and supporting the second solid-state UV emitter in a second housing such that a principal optical axis of the second solid-state UV emitter is at least generally co-axial with the central channel axis and wherein an inlet aperture for the fluid inlet, where the fluid inlet opens into the bore of the fluid flow channel, is defined by a combination of the outer conduit-defining wall and the second housing.

In some embodiments, there is provided an ultraviolet (UV) reactor for irradiating a flow of fluid with UV radiation. The reactor may comprise: a fluid conduit defined at least in part by an outer conduit-defining wall for permitting a fluid flow therethrough; a solid-state UV emitter (e.g. ultraviolet light emitting diode or UV-LED); and a radiation-focusing element comprising one or more lenses; wherein the fluid conduit comprises a fluid inlet, a fluid outlet and a longitudinally extending fluid flow channel located between the inlet and the outlet, the fluid flow channel extending in a longitudinal direction for permitting the fluid flow in a longitudinal direction through a bore of the fluid flow channel and the fluid flow channel having a central channel axis that extends in the longitudinal direction through centroids of transverse cross-sections of the bore in at least a longitudinally central portion of the bore; wherein the one or more lenses are positioned in a radiation path of radiation emitted from the solid-state UV emitter for directing radiation from the solid-state UV emitter to impinge on the fluid flowing in the fluid flow channel and to thereby provide a radiation fluence rate profile within the bore of the fluid flow channel; and wherein the one or more lenses comprise a half-ball lens positioned to receive radiation from the UV emitter and a plano-convex lens positioned to receive radiation from the half-ball lens, with both the half-ball lens and plano-convex lens having their planar sides facing the UV emitter and with the solid state UV emitter, the half-ball lens and the plano-convex lens having their optical axes parallel with, and in some cases co-axial with, the central channel axis.

In some embodiments, the plano-convex lens may be positioned at a distance f', which is less than its inherent focal length f1, from a focal point of radiation emitted from the half-ball lens. In some embodiments, there is provided a UV reactor wherein a spacing f' of the plano-convex lens relative to the focal point of the half-ball lens may be less than the inherent focal length f1 of the plano-convex lens by a differential distance Δ and the differential distance Δ is in a range of 10%-35% of the focal length f1 of the plano-convex lens. In some embodiments, there is provided a UV reactor which may comprise: a second solid-state UV emitter having a secondary principal optical axis that may be oriented anti-parallel to the principal optical axis of the solid-state UV emitter; and a second radiation-focusing element comprising one or more secondary lenses positioned in a second radiation path of radiation emitted from the second solid-state UV emitter for directing radiation from the second solid-state UV emitter to impinge on the fluid flowing in the fluid flow channel and to thereby provide a second radiation fluence rate profile within the bore of the fluid flow channel; wherein the one or more secondary lenses may comprise a secondary half-ball lens positioned to receive radiation from the second UV emitter and a secondary plano-convex lens positioned to receive radiation from the secondary half-ball lens, with both the secondary half-ball lens and secondary plano-convex lens having their planar sides facing the second UV emitter and with the second solid state UV emitter, the secondary half-ball lens and the secondary plano-convex lens having their optical axes parallel with, and in some cases co-axial with, the central channel axis. For example, the secondary plano-convex lens may be positioned at a second distance $f_2'$, which is less than its inherent focal length f2, from a focal point of radiation emitted from the secondary half-ball lens; and a second spacing $f_2'$ of the secondary plano-convex lens relative to the focal point of the secondary half-ball lens may be less than the inherent focal length f2 of the second plano-convex lens by a second differential distance $\Delta_2$ and the second differential distance $\Delta_2$ is in a range of 10%-35% of the focal length f2 of the secondary plano-convex lens.

In some embodiments, there is provided a method for using an ultraviolet (UV) reactor for irradiating a fluid travelling through the reactor with UV radiation to thereby treat the fluid. The method may comprise: providing a UV reactor comprising a fluid conduit defined at least in part by an outer conduit-defining wall for permitting a fluid flow therethrough, a solid-state UV emitter (e.g. ultraviolet light emitting diode or UV-LED), and a radiation-focusing element comprising one or more lenses; introducing the fluid into a bore of a longitudinally extending fluid flow channel via a fluid inlet, allowing the fluid to flow through the longitudinally extending fluid flow channel in a longitudinal direction and removing the fluid from the fluid flow channel via a fluid outlet, the fluid outlet located at a longitudinally opposite end of the fluid flow channel from the inlet, wherein the fluid flow channel has a central channel axis that extends in the longitudinal direction through centroids of transverse cross-sections of the bore in at least a longitudinally central portion of the bore; directing radiation from the solid-state UV emitter through the one or more lenses and thereby causing the radiation to impinge on the fluid flowing in the fluid flow channel and to thereby provide a radiation fluence rate profile within the bore of the fluid flow channel; wherein the one or more lenses comprise a half-ball lens and a plano-convex lens and the method comprises: positioning the half-ball lens to receive radiation from the UV emitter, positioning the plano-convex lens to receive radiation from the half-ball lens, orienting both the half-ball lens and plano-convex lens to have their planar sides facing the UV emitter and aligning the solid state UV emitter, the half-ball lens and the plano-convex lens to have their optical axes parallel with, and in some cases co-axial with, the central channel axis.

For example, positioning the plano-convex lens may comprise positioning the plano-convex lens at a distance f', which is less than its inherent focal length f1, from a focal point of radiation emitted from the half-ball lens. In some embodiments, a spacing f' of the plano-convex lens relative to the focal point of the half-ball lens may be less than the inherent focal length f1 of the plano-convex lens by a differential distance Δ and the differential distance Δ may be in a range of 10%-35% of the focal length f1 of the plano-convex lens.

In some embodiments, the method may comprise: a second solid-state UV emitter having a secondary principal optical axis that is oriented anti-parallel to the principal optical axis of the solid-state UV emitter; and providing a second solid state emitter (e.g. ultraviolet light emitting diode or UV-LED) that is oriented anti-parallel to the principal optical axis of the solid-state UV emitter; and a second radiation-focusing element comprising one or more secondary lenses; directing second radiation from the second solid-state UV emitter through the one or more secondary lenses and thereby causing the second radiation to impinge on the fluid flowing in the fluid flow channel and to thereby provide a second radiation fluence rate profile within the bore of the fluid flow channel; wherein the one or more secondary lenses comprise a secondary half-ball lens and a secondary plano-convex lens and the method comprises: positioning the secondary half-ball lens to receive second radiation from the second UV emitter, positioning the secondary plano-convex lens to receive second radiation from the secondary half-ball lens, orienting both the secondary half-ball lens and secondary plano-convex lens to have their planar sides facing the second UV emitter and aligning the second solid state UV emitter, the secondary half-ball lens and the secondary plano-convex lens to have their optical axes co-axial with the central channel axis.

For example, positioning the secondary plano-convex lens may comprise positioning the secondary plano-convex lens at a second distance $f_2'$, which is less than its inherent focal length f2, from the focal point of radiation emitted from the secondary half-ball lens. In some embodiments, the method may comprise a second spacing $f_2'$ of the secondary plano-convex lens relative to the focal point of the secondary half-ball lens which may be less than the inherent focal length f2 of the second plano-convex lens by a second differential distance $\Delta_2$ and the second differential distance $\Delta_2$ may be in a range of 10%-35% of the focal length f2 of the secondary plano-convex lens.

In some embodiments, there is provided a method for using the UV reactor comprising installing the UV reactor in an existing fluid flow conduit that extends in a first direction, wherein installing the UV reactor in the existing fluid flow conduit may comprise: removing a section of the existing conduit from the existing conduit to expose an upstream portion of the existing conduit and a downstream portion of the existing conduit, the upstream portion and downstream portion generally aligned with one another in the first direction; connecting the fluid inlet of the UV reactor to an end of the upstream portion of the existing conduit; and connecting the fluid outlet of the UV reactor to an end of the downstream portion of the existing conduit; wherein connecting the fluid inlet of the UV reactor to the end of the upstream portion of the existing conduit and connecting the fluid outlet of the UV reactor to the end of the downstream portion of the existing conduit together comprise aligning the longitudinal direction of fluid flow with the first direction.

While the embodiments described herein are presented with particular features and fluid flow channel configurations or lens configurations and the like, it is to be understood that any other suitable combination of the features or configurations described herein may be present in a UV-LED reactor and in methods for use and/or fabrication of same. While a number of exemplary embodiments have been described, those of skill in the art will recognize certain modifications, permutations, additions and sub-combinations thereof. It is therefore intended that the scope of the following appended claims and claims hereafter introduced should not be limited by the embodiments set forth in the examples, but should be given the broadest interpretation consistent with the description as a whole.

What is claimed is:

1. An apparatus, comprising:

a body extending along a flow path between a first end and a second end opposite of the first end along the flow path, the first end comprising an inlet along the flow path, the second end comprising an outlet along the flow path;

a flow channel extending inside the body along the flow path to direct a fluid from the inlet to the outlet; and a radiation source removably mountable in a cavity in the flow channel, the radiation source comprising a housing and a solid-state UV emitter housed in the housing and capable of emitting radiation in the flow channel along the flow path, the radiation source further comprising a thermally conductive material thermally coupled to the solid-state UV emitter and positioned to be in direct or indirect thermal contact with the fluid when the fluid is in the flow channel between the inlet and the outlet and when the radiation source is mounted in the cavity, wherein the flow channel comprises a first portion and a second portion, the first portion having a first cross-sectional area, the second portion having a second cross-sectional area, the second cross-sectional area greater than the first cross-sectional area, the radiation source is in the second portion, the solid-state UV emitter is configured to emit the radiation into the first portion, the cavity is defined by interior surfaces of the flow channel, and the apparatus further comprises a mounting structure extending between the interior surfaces of the cavity and exterior surfaces of the radiation source when the radiation source is mounted in the cavity to maintain a position of the radiation source relative to the flow channel when the fluid is flowing from the inlet to the outlet and the radiation source is mounted in the cavity.

2. The apparatus of claim 1, wherein the radiation source has a cross-sectional area greater than the first cross-sectional area.

3. The apparatus of claim 1,
wherein the interior surfaces of the flow channel are configured to cause the fluid to flow in contact with the thermally conductive material when the fluid is flowing from the inlet to the outlet and the radiation source is mounted in the cavity.

4. An apparatus, comprising:
a body extending along a flow path between a first end and a second end opposite of the first end along the flow path, the first end comprising an inlet along the flow path, the second end comprising an outlet along the flow path;
a flow channel extending inside the body along the flow path to direct a fluid from the inlet to the outlet; and
a radiation source removably mountable in a cavity in the flow channel, the radiation source comprising a housing and a solid-state UV emitter housed in the housing and capable of emitting radiation in the flow channel along the flow path, the radiation source further comprising a thermally conductive material thermally coupled to the solid-state UV emitter and positioned to be in direct or indirect thermal contact with the fluid when the fluid is in the flow channel between the inlet and the outlet and when the radiation source is mounted in the cavity,
wherein the cavity is defined by interior surfaces of the flow channel,
the apparatus further comprises a mounting structure extending between the interior surfaces of the cavity and exterior surfaces of the radiation source when the radiation source is mounted in the cavity to maintain a position of the radiation source relative to the flow channel when the fluid is flowing from the inlet to the outlet and the radiation source is mounted in the cavity, and
the mounting structure does not extend to the thermally conductive material of the radiation source, when the radiation source is mounted in the cavity, to prevent heat transfer between the thermally conductive material of the radiation source, the body, and the fluid when the fluid is in the flow channel between the inlet and the outlet.

5. The apparatus of claim 4, further comprising:
one or more lenses positionable to refract the radiation from the solid-state UV emitter.

6. The apparatus of claim 5,
wherein the one or more lenses are configured to cause fluence rates of the radiation at a location in the flow channel to be correlated with velocities of the fluid at the location in the flow channel when the fluid is flowing from the inlet to the outlet, the radiation source is mounted in the cavity, and the solid-state UV emitter emits the radiation in the flow channel.

7. The apparatus of claim 5,
wherein the one or more lenses comprise one or more of a lens with at least a partially convex face lens, a dome lens, a plano-convex lens, or a Fresnel lens.

8. The apparatus of claim 4,
wherein the radiation source is an optical unit having the exterior surfaces of the radiation source,
the optical unit is removably mountable within the cavity, and
the interior surfaces of the flow channel are configured to cause the fluid to flow around the optical unit and in contact with the thermally conductive material when the fluid is flowing from the inlet to the outlet and the radiation source is mounted in the cavity.

9. The apparatus of claim 8,
wherein the optical unit further comprises one or more lenses positionable to refract the radiation from the solid-state UV emitter.

10. The apparatus of claim 4,
wherein the radiation source is an optical unit having the exterior surfaces of the radiation source,
the optical unit is removably mountable within the cavity, and
the interior surfaces of the flow channel are configured to cause the fluid to flow in contact with the thermally conductive material when the fluid is flowing from the inlet to the outlet and the radiation source is mounted in the cavity.

11. The apparatus of claim 10,
wherein the mounting structure comprises perforated material.

12. The apparatus of claim 4,
wherein the interior surfaces of the flow channel are configured to cause the fluid to flow around the radiation source and in contact with the thermally conductive material when the fluid is flowing from the inlet to the outlet and the radiation source is mounted in the cavity.

13. The apparatus of claim 12, further comprising:
an optical unit comprising the radiation source,
wherein the interior surfaces of the cavity are engageable with exterior surfaces of the optical unit to maintain a position of the radiation source relative to the flow channel when the fluid is flowing from the inlet to the outlet and the radiation source is mounted in the cavity.

14. The apparatus of claim 4,
wherein the cavity is at the second end of the flow path.

15. The apparatus of claim 4,
wherein the inlet and the outlet are mountable in-line with a pipe.

16. The apparatus of claim 4,
wherein the cavity is a first cavity, the radiation source is a first radiation source, the housing is a first housing, the solid-state UV emitter is a first solid-state UV emitter, the radiation is a first radiation, the thermally conductive material is a first thermally conductive material, the flow channel defines a second cavity, and the apparatus further comprises:
a second radiation source mountable in the second cavity, the second radiation source comprising a second housing and a second solid-state UV emitter housed in the housing to emit a second radiation in the flow channel along the flow path, the second radiation source further comprising a second thermally conductive material thermally coupled to the second solid-state UV emitter and positioned to be contacted by the fluid when the fluid is flowing from the inlet to the outlet and the second radiation source is mounted in the second cavity.

17. The apparatus of claim 16,
wherein, when the first radiation source is mounted in the first cavity and the second radiation source is mounted in the second cavity:
the first solid-state UV emitter is positioned to emit the first radiation along the flow path in a first direction,
the second solid-state UV emitter is positioned to emit the second radiation along the flow path in a second direction, and
the first direction is different from the second direction.

18. The apparatus of claim 4,
wherein the radiation source comprises a plurality of solid-state UV emitters and the thermally conductive material is either common to or individualized for the plurality of solid- state UV emitters.

19. The apparatus of claim 4,
wherein the flow channel has a central channel axis that extends along the flow path through centroids of transverse cross-sections of the flow channel; and
when the radiation source is mounted in the cavity and the solid-state UV emitter emits the radiation in the flow channel, the radiation emitted in the flow channel has a principal optical axis generally aligned with the central channel axis of the flow channel.

20. The apparatus of claim 4, further comprising:
a printed circuit board,
wherein the solid-state UV emitter is mounted on the printed circuit board.

21. The apparatus of claim 4,
wherein the radiation source is contained in an optical unit having exterior surfaces and comprising the thermally conductive material, and
the optical unit is removably mountable within the cavity.

22. The apparatus of claim 21,
wherein the optical unit comprises a heat sink,
the thermally conductive material comprises the heat sink, and
the heat sink defines a thermally-conducting exterior surface of the optical unit.

23. The apparatus of claim 21,
wherein the thermally conductive material defines a thermally-conducting exterior surface of the optical unit.

24. The apparatus of claim 4,
wherein the thermally conductive material is on a side of the solid-state UV emitter opposing a principal optical axis of the solid-state UV emitter or portion thereof.

25. The apparatus of claim 4,
wherein the housing, on the side of the solid-state UV emitter opposing the principal optical axis of the solid-state UV emitter or portion thereof, is in direct or indirect thermal contact with the solid-state UV emitter via a printed circuit board.

26. The apparatus of claim 4, further comprising:
a printed circuit board including the thermally conductive material, wherein the solid-state UV emitter is mounted on the printed circuit board and thermally coupled to the thermally conductive material.

27. The apparatus of claim 4, wherein the mounting structure comprises perforated material.

28. The apparatus of claim 4,
wherein the thermally conductive material is spaced apart from the interior surfaces of the flow channel when the radiation source is mounted in the cavity.

29. The apparatus of claim 4,
wherein the interior surfaces of the flow channel are configured to cause the fluid to flow from a front side of the radiation source to a rear side of the radiation source opposite the front side of the radiation source, and
the solid-state UV emitter is configured to emit the radiation from at least the front side of the radiation source.

30. The apparatus of claim 4,
wherein the interior surfaces of the flow channel are configured to cause the fluid to flow from a rear side of the radiation source to a front side of the radiation source opposite the rear side of the radiation source, and
the solid-state UV emitter is configured to emit the radiation from at least the front side of the radiation source.

31. The apparatus of claim 4,
wherein at least a portion of the thermally conductive material is spaced apart from the interior surfaces of the flow channel when the radiation source is mounted in the cavity.

32. The apparatus of claim 4,
wherein the thermally conductive material comprises a metallic material.

33. The apparatus of claim 4,
wherein the interior surfaces of the flow channel are configured to cause the fluid to flow in contact with the thermally conductive material when the fluid is flowing from the inlet to the outlet and the radiation source is mounted in the cavity.

34. An apparatus, comprising:
a body extending along a flow path between a first end and a second end opposite of the first end along the flow path, the first end comprising an inlet along the flow path, the second end comprising an outlet along the flow path;
a flow channel extending inside the body along the flow path to direct a fluid from the inlet to the outlet; and
a radiation source removably mountable in a cavity in the flow channel, the radiation source comprising a housing and a solid-state UV emitter housed in the housing and capable of emitting radiation in the flow channel along the flow path, the radiation source further comprising a thermally conductive material thermally coupled to the solid-state UV emitter and positioned to be in direct or indirect thermal contact with the fluid when the fluid is in the flow channel between the inlet and the outlet and when the radiation source is mounted in the cavity,
wherein the flow channel comprises a first portion and a second portion, the first portion having a first cross-sectional area, the second portion having a second cross-sectional area, the second cross-sectional area greater than the first cross-sectional area,
the radiation source is in the second portion,
the solid-state UV emitter is configured to emit the radiation into the first portion, and
the first and second portions are coaxial.

35. The apparatus of claim 34,
wherein the radiation source has a cross-sectional area greater than the first cross-sectional area.

36. The apparatus of claim 34,
wherein the cavity is defined by interior surfaces of the flow channel, and
the apparatus further comprises a mounting structure extending between the interior surfaces of the cavity and exterior surfaces of the radiation source when the radiation source is mounted in the cavity to maintain a position of the radiation source relative to the flow channel when the fluid is flowing from the inlet to the outlet and the radiation source is mounted in the cavity.

* * * * *